United States Patent [19]

Feder et al.

[11] Patent Number: 4,851,517

[45] Date of Patent: Jul. 25, 1989

[54] TISSUE PLASMINOGEN ACTIVATOR OLIGOSACCHARIDE FROM NORMAL HUMAN COLON CELLS

[75] Inventors: Joseph Feder, University City; William R. Tolbert, Manchester, both of Mo.; Thomas W. Rademacher, Oxford, United Kingdom; Raj B. Parekh, Oxford, United Kingdom; Raymond A. Dwek, Oxford, United Kingdom

[73] Assignee: Monsanto Company, St. Louis, Mo.

[21] Appl. No.: 159,992

[22] Filed: Feb. 24, 1988

Related U.S. Application Data

[60] Division of Ser. No. 929,950, Nov. 12, 1986, Pat. No. 4,751,084, Continuation-in-part of Ser. No. 834,080, Feb. 26, 1986, abandoned.

[51] Int. Cl.$^4$ ............................................. C07H 3/06
[52] U.S. Cl. ........................................ 536/1.1; 536/123; 536/53
[58] Field of Search ............................. 536/1.1, 123, 53

[56] References Cited

U.S. PATENT DOCUMENTS

| | | | |
|---|---|---|---|
| 3,904,480 | 9/1975 | Hull et al. | 435/215 |
| 4,190,708 | 2/1980 | Kuo et al. | 435/215 |
| 4,335,215 | 6/1982 | Tolbert et al. | 435/241 |
| 4,505,893 | 3/1985 | Mori et al. | 424/94 |
| 4,537,860 | 8/1985 | Tolbert et al. | 435/240 |
| 4,550,080 | 10/1985 | Hasegawa et al. | 435/212 |

FOREIGN PATENT DOCUMENTS

| | | |
|---|---|---|
| 41766 | 12/1981 | European Pat. Off. |
| 117059 | 8/1984 | European Pat. Off. |
| 238304 | 3/1987 | European Pat. Off. |
| 2119804 | 11/1983 | United Kingdom |

OTHER PUBLICATIONS

Rijkin and Collen, J. Biol. Chem., 256 (13), 7035-41, (1981).
Kluft et al., Adv. Biotech. Proc. 2, Alan R. Liss, Inc., 1983, pp. 97-110.
Ranby et al., FEBS Lett. 146(2), 289-92, (1982).
Wallen et al., Eur. J. Biochem., 132, 681-6, (1983).
Pohl et al., Biochemistry, 23, 3701-07, (1984).
Pohl et al., EMBO Workshop on Plasminogen Activators, Amalfi, Italy, Oct. 14-18, 1985.
Pennica et al., Nature, 301, 214-21, (1983).
Vehar et al., Biotech., 2(12), 1051-57, (1984).
Collen et al., Circulation 70(16), 1012-17, (1984).
Little et al., Biochemistry, 23, 6191-95, (1984).
Opdenakker et al., EMBO Workshop, supra.
Brouty-Boye et al., Biotech., 2(12), 1058-62, (1984).
Pohl et al., FEBS Lett., 168(1), 29-32, (1984).
Kaufman et al., Mol. Cell. Biol., 5, 1750-59, (1985).
Browne et al., Gene, 33, 279-84, (1985).
Zamarron et al., J. Biol. Chem., 259(4), 2080-83, (1984).
Collen et al., J. Pharmacol. Expertl. Therap., 231(1), 146-52, (1984).
Rijken et al., Biochem. Biophys. Acta, 580, 140-153, (1979).
Husain et al., Proc. Natl. Acad. Sci., U.S.A., 78(7), 4265-69, (1981).
Schleef et al., Thromb. Haemos., 53(1), 170-175, (1985).
Corasanti et al., J. Natl. Cancer Inst., 65(2), 345-351, (1980).
Tissot and Bachman, Prog. Fibrinolysis, 6, 133-135, (1983).
Tissot et al., Int. J. Cancer, 34, 295-302, (1984).
Pohl et al., Eur. J. Biochem., 170(1/2), 69-75, (1987).

*Primary Examiner*—Johnnie R. Brown
*Assistant Examiner*—Jacqueline M. Stone
*Attorney, Agent, or Firm*—Scott J. Meyer; James W. Williams, Jr.

[57] ABSTRACT

Glycosylated plasminogen activator (t-PA) having a glycosylation pattern significantly different than exhibited by t-PA from Bowes melanoma cells is obtained from cultured normal human colon fibroblast cells (CCD-18Co).

1 Claim, 11 Drawing Sheets

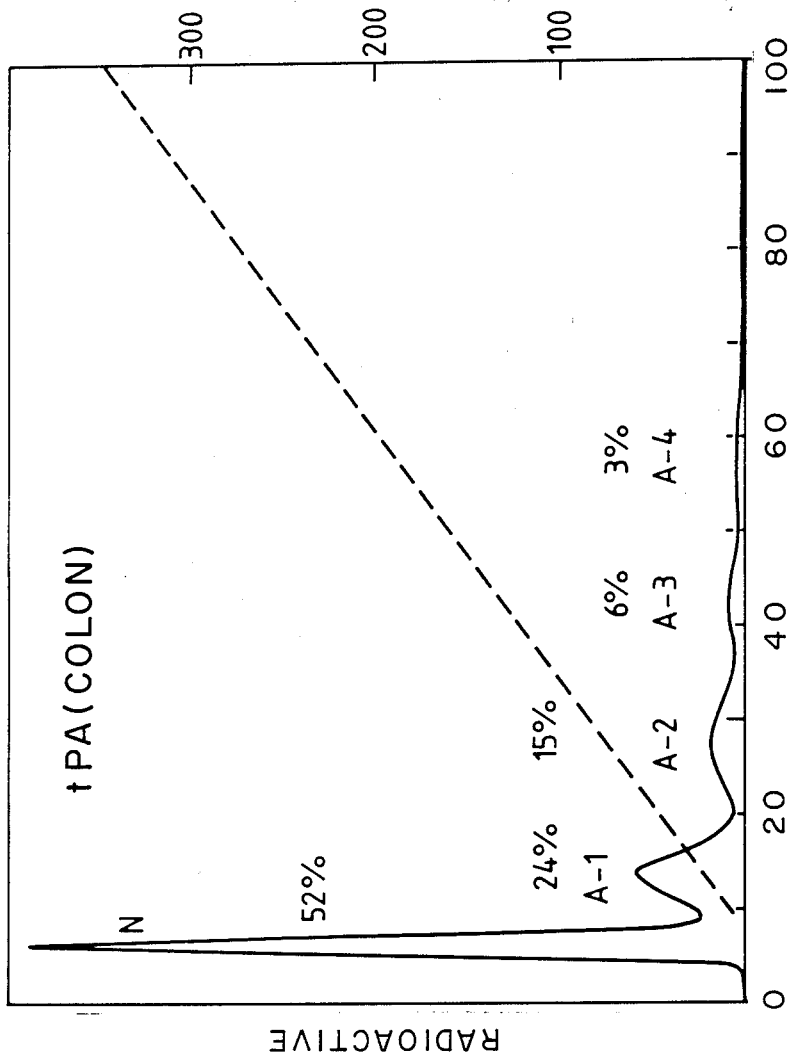

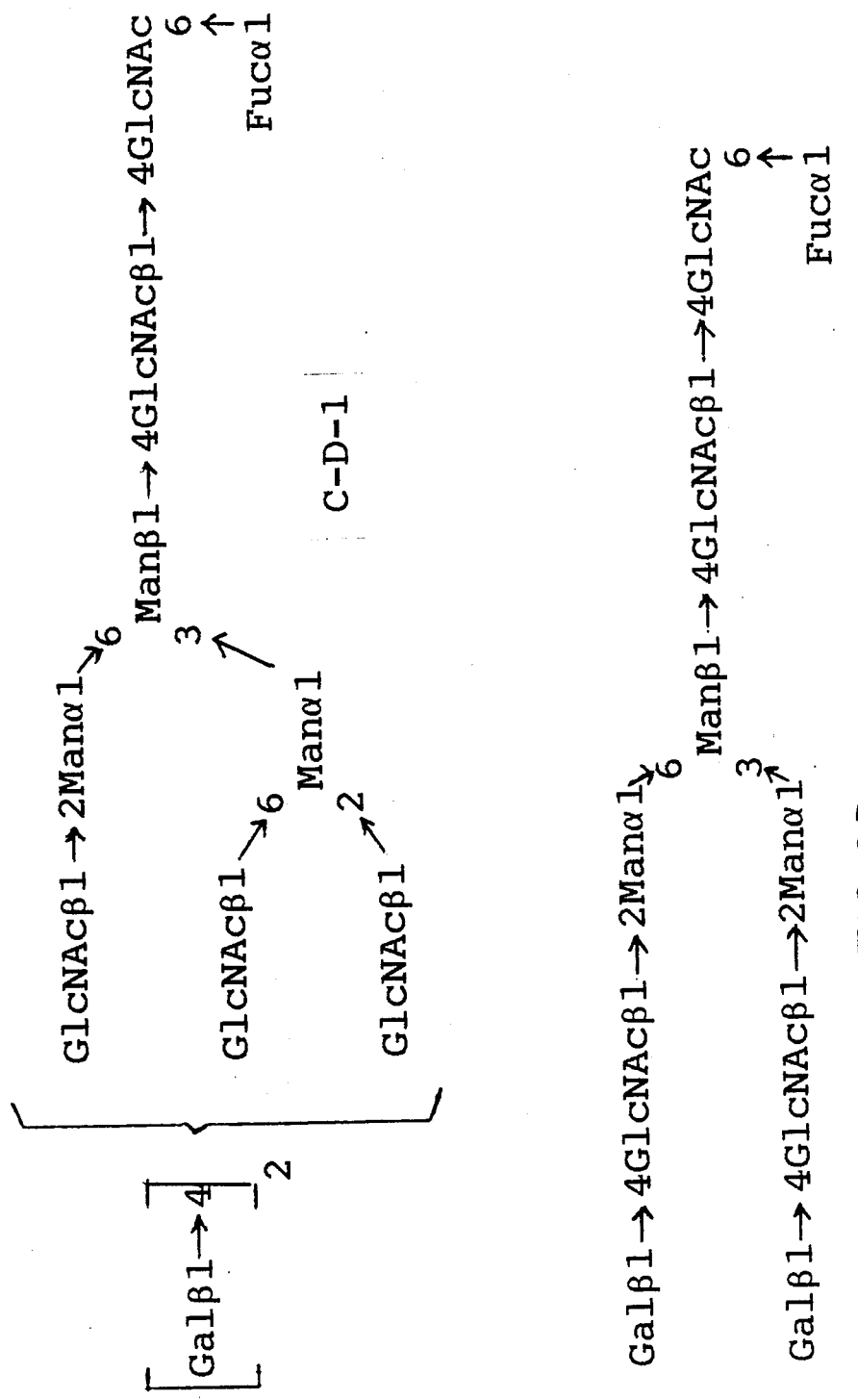

TISSUE PLASMINOGEN ACTIVATOR OLIGOSACCHARIDE FROM NORMAL HUMAN COLON CELLS

CROSS-REFERENCE TO RELATED APPLICATION

This is a division of application Ser. No. 929,950, filed Nov. 12, 1986, now U.S. Pat. No. 4,751,084 which is a continuation-in-part of copending application Ser. No. 834,080, filed Feb. 26, 1986.

BACKGROUND OF THE INVENTION

This invention relates to plasminogen activators which are useful thrombolytic agents. More particularly, this invention relates to glycosylated tissue plasminogen activator from cultured normal human colon cells.

It is known that various plasminogen activators (PA) are widely distributed throughout the body and can be purified from tissue extracts. Typical examples of tissue sources are kidney and lung tissues. The best characterized of these plasminogen activators fall into two major groups, urokinase plasminogen activator (u-PA) and tissue plasminogen activator (t-PA). u-PA and t-PA are present in ng/ml concentrations in human plasma but are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application No. 41,766, published Dec. 16, 1981; Rijken and Collen, *J. Biol. Chem.* 256(13), 7035–7041 (1981); and Kluft et al., *Adv. Biotech. Proc.* 2, Alan R. Liss, Inc., 1983, pp. 97–110. The Bowes melanoma t-PA is a glycoprotein which has a molecular weight of about 68,000–70,000 daltons and a 527 amino acid structure with serine as the N-terminal. The melanoma t-PA exists as two chains, an A-chain and a B-chain. It also separates into two variants in the A-chain, known as types I and II, which differ by about $M_r$ 2000–3000. See Ramby et al., *FEBS Lett.* 146 (2), 289–292 (1982), and Wallen et al., *Eur. J. Biochem.* 132, 681–686 (1983). Type I is glycosylated at Asn-117, Asn-184 and Asn-448 whereas Type II is glycosylated only at Asn-117 and Asn-448 according to Pohl et al., *Biochemistry* 23, 3701–3707 (1984). A high mannose structure has been assigned to Asn-117 whereas two complex carbohydrate structures are assigned to Asn-184 and Asn-448 by Pohl et al., "EMBO Workshop on Plasminogen Activators," Amalfi, Italy, Oct. 14–18, 1985.

Genetic information from the Bowes melanoma cell line also has been embodied in *E. coli* by conventional recombinant DNA gene splicing methods to permit the production of the t-PA protein moiety by that microorganism. See, for example, UK Patent Application No. 2,119,804, published Nov. 23, 1983; Pennica et al., *Nature* 301, 214–221 (1983); and Vehar et al., *Biotech.* 2 (12), 1051–1057 (1984). Recombinant t-PA produced by the expression of Bowes melanoma genetic material in cultured mammalian cells has been administered to humans with some measure of effectiveness. See Collen et. al., *Circulation* 70(16), 1012–1017 (1984).

Notwithstanding the apparent utility of the t-PA derived from Bowes melanoma, the use of cancer cells or genetic information derived from cancer cells can raise uncertain drug regulatory problems in the therapeutic use of such materials. Thus, it is known that cancer cells (transformed cells) can produce human transforming growth factors. See, for example, Delarco and todaro, *Proc. Natl. Acad. Sci. USA* 75, 4001–4005 (1978), and Todaro et al., *Ibid.*, 77, 5258–5261 (1980). Even the smallest amount of residual DNA from the cancer cells can be integrated into and expressed in the *E. coli* or genetically engineered mammalian cells, thereby raising the possibility of harmful effects if t-PA from such source is administered to the patient. Although the risks may be small by the judicious use of various purification techniques and appropriate monitoring of patients, it still would be preferable to use a t-PA that was not derived from cancer cells either directly or indirectly. The possible presence of viral genetic material or oncogene product can raise significant objections to the use of clinical material thus derived from transformed cells.

Moreover, the recombinant-derived t-PA produced in *E. coli* is non-glycosylated and contains only the protein moiety of t-PA. Althuogh the specific function of the carbohydrate moiety on t-PA has not been determined, it is known, in general, that glycosylation can cause certain differences in the protein of which the following are of biological interest: antigenicity, stability, solubility and tertiary structure. The carbohydrate side-chains also can affect the protein's half life and target it to receptors on the appropriate cells. See, for example, Delente, *Trends in Biotech.* 3 (9), 218 (1985), and Van Brunt, *Biotechnol.* 4, 835–839 (1986). The functional properties of carbohydrate-depleted t-PA are further discussed by Little, et al., *Biochemistry* 23, 6191–6195 (1984), and by Opdenakker et al., "EMBO workshop on Plasminogen Activators," Amalfi, Italy, Oct. 14–18, 1985. The latter scientists report that enzymatic cleavage of carbohydrate side-chains from the melanoma (Bowes) derived t-PA by treatment with α-mannosidase causes an increase in the biologic activity of the modified t-PA.

Accordingly, the production of glycosylated t-PA from normal human cells on a large scale would be highly desirable. Cultured normal human cells have been used as a source of t-PA as can be seen from U.S. Pat. Nos. 4,335,215, 4,505,893, 4,537,860, and 4,550,080. Although various cell sources are mentioned in said patents, apparently only primary embryonic (or fetal) kidney, lung, foreskin, skin and small intestines (Flow Laboratories) or the AG1523 cell line were actually cultured for the production of t-PA according to the disclosures. Brouty-Boye et al., *Biotech* 2 (12), 1058–1062 (1984), also disclose the use of normal human embryonic lung cells for the production of t-PA. Rijken and Collen, *J. Biol. Chem.* 256 (13), 7035–7041 (1981), and Pohl et al., *FEBS Lett.* 168(1), 29–32 (1984), disclose the use of human uterine tissue as a t-PA source material. However, none of the foregoing disclosures on normal human cell-derived t-PA define the carbohydrate structures on the t-PA protein.

Production of glycosylated t-PA in non-human mammalian cells also is known. Thus, Kaufman et al., *Mol. Cell. Biol.* 5, 1750–1759 (1985), and European Patent Application No. 117,059, published Aug. 29, 1984, describe the use of Chinese hamster ovary cells and Browne et al., *Gene* 33, 279–284 (1985), describe the use of mouse L cells for such production. Kaufman et al., state that the Chinese hamster ovary t-PA is glycosylated in a similar but not identical manner as native t-PA. Glycosylated forms of t-PA obtained by recombinant DNA are further described by Zamarron et al., *J. Biol. Chem.* 259 (4), 2080–2083 (1984), and Collen et al., *J. Pharmacol. Expertl. Therap.* 231 (1), 146–152 (1984).

Production of glycosylated t-PA by recombinant DNA yeast cells also has been reported. Thus, European Patent Application No. 143,081, published May 29, 1985, describes a recombinant yeast plasmid vector which encodes human t-PA from Hela cells. The latter cells are known to be tumor derived. European Patent Application No. 174,835, published Mar. 19, 1986, describes a t-PA with selected glycosylation expressed in yeast. However, the cDNA encoding for the t-PA is derived from Bowes melanoma which also is tumor derived. European Patent Application No. 178,015, published Apr. 16, 1986, discloses a glycosylated uterine t-PA expressed in yeast cells or mouse cells. In the latter case, a bovine papilloma virus is used as the vector. Papilloma viruses have been implicated in natural cancers.

Although glycosylation is suggested in various of the foregoing European Patent Application disclosures, the glycosylation patterns are not described and sugar molecules are not identified.

It is apparent that differences in the glycosylation pattern on similar proteins can have profound effects on antigenicity, metabolism and other physiological properties. See, for example, the association of rheumatoid arthritis and osteoarthritis with changes in the glycocosylation pattern of total serum IgG by Parekh et al., *Nature* 316, 452–457 (1985).

Another example of a glycoprotein in which biological activity resides in the oligosaccharide moieties (i.e., particular structure at a specific site) is that of human chorionic gonadotropin (hCG). Thus, it is known that hCG without carbohydrate is a competitive inhibitor of native hCG; that oligo-saccharides isolated from hCG inhibit action of native hCG; and that tumor-produced hCG having the same amino acid sequence as native hCG but different sugars has almost no biological activity. See Calvo et al., *Biochemistry* 24, 1953–1959 (1985); Chen et al., *J. Biol. Chem.* 257 14446–14452 (1982).

BRIEF DESCRIPTION OF THE INVENTION

In accordance with the present invention, plycosylated t-PA is obtained from cultured normal human colon cells which are adaptable to large scale production. A purified color t-PA is provided which has a unique, heterogeneous glycosylation pattern that differs significantly from the t-PA of Bowes melanoma although the protein moieties are substantially similar.

The glycosylated colon t-PA of this invention has been isolated in a highly purified form which did not exist in the human colon cells from which it was obtained. That is, it has been prepared in a form which is essentially free of other glycoproteins, and free from other cellular components and tissue matter.

In a preferred embodiment of the invention, the glycosylated colon t-PA of this invention is isolated from the normal human colon fibroblast cell line CCD-18Co. Both u-PA and t-PA are obtainable from the culture fluids of this cell line in large scale production lots. The colon u-PA has a molecular weight of about 54,000 daltons whereas the colon t-PA has a molecular weight of about 67,000 daltons.

The CCD-18Co cell line is on deposit without restriction in the permanent collection of the American Type Culture Collection. Rockville, Md., under accession number ATCC CRL-1459. Samples of the cell line can be obtained by the public upon request to that depository.

Determination of the structure of the protein moiety of the colon t-PA can be carried out by well-known methods described for melanoma t-PA by Pennica et al., *Nature* 301, 214–221 (1983), and UK Patent Application No. 2,119,804, published Nov. 23, 1983. Thus, recent advances in biochemistry and recombinant DNA technology can be utilized to synthesize specific proteins under controlled conditions independent of the organism from which they are normally isolated. These biochemical synthetic methods employ enzymes and subcellular components of the protein synthesizing systems of living cells, either in vitro in cell-free systems, or in vivo in microorganisms. In either case, the principal element is provision of a deoxyribonucleic acid (DNA) of specific sequence which contains the information required to specify the desired amino acid sequence. Such a specific DNA sequence is termed a gene. The coding relationships whereby a DNA sequence is used to specify the amino acid sequence of a protein is well-known and operates according to a fundamental set of principles. See, for example, Watson, *Molecular Biology of the Gene* 3d ed., Benjamin-Cummings, Menlo Park, Calif., 1976.

A cloned gene may be used to specify the amino acid sequence of proteins synthesized by in vitro systems. DNA-directed protein synthesizing systems are well established in the art. Single-stranded DNA can be induced to act as messenger RNA (mRNA) in vitro, thereby resulting in high fidelity translation of the DNA sequence.

It is now possible to isolate specific genes or portions thereof from higher organisms, such as man and animals, and to transfer the genes or fragments to microorganisms such as bacteria or yeasts. The transferred gene is replicated and propagated as the transformed microorganism replicates. Consequently, the transformed microorganism is endowed with the capacity to make the desired protein or gene which it encodes, and then passes on this capability to its progeny. See, for example, Cohen and Boyer, U.S. Pat. Nos. 4,237,224 and 4,468,464.

According to these recombinant DNA methods it was determined that the mature t-PA protein from human melanoma cells has a 527 amino acid sequence as disclosed by Pennica and in UK Pat. Appln. No. 2,119,804, supra. It has also been determined that the t-PA protein molecule from human melanoma cells is glycosylated at asparagine positions 117, 184 and 448. See Vehar et al., *Biotech.*, December 1984, pp. 1051–1057. Said disclosures on amino acid sequence and glycosylation positions are incorporated herein by reference.

Although the amino acid sequence of the colon t-PA of this invention is substantially similar to the corresponding protein from melanoma t-PA and also is glycosylated at asparagine positions 117, 184 and 448, the glycosylation pattern differs significantly as described hereinbelow.

Determination of the structure of the oligosaccharides from the colon t-PA employs adaptation of the method used for Immunoglobulin G-derived asparagine-linked oligosaccharides as described by Rademacher and Dwek, *Prog. Immunol.* 5, 95–112 (1983) and Parekh et al., *Nature* 316, 452–457 (1985). According to this method, the glycoprotein sample is subjected to controlled hydrazinolysis to release intact its associated oligosaccharide moieties as described by Takahasi et al., *Meth. Enzymol.* 83, 263–268 (1982). Reduction of the reducing terminal N-acetylglucosamine residues using $NaB^3H_4$ is then performed to label radioactively each carbohydrate chain. Each labeled oligosaccharide mixture is then subjected to exhaustive neuraminidase digestion in order to analyze the distribution of neutral structures. The resulting 'asialo' oligosaccharide mixtures are then fractionated by Bio-Gel TM P-4 (~400 mesh) gel filtration chromatography, which separates neutral oligosaccharides on the basis of the effective hydrodynamic volumes as described by Yamashita et al., *Meth. Enzymol.* 83, 105–126 (1982). Bio-Gel P-4 is a gel filtration material of choice for analysis of reduced oligosaccharides by high voltage gel permeation chromatography due to the polyacrylamide structure. Bio-Gel P is prepared by copolymerization of acrylamide with N,N'-methylene bis-acrylamide. P-4 has an exclusive limit and fractionation range of about 800–4000 daltons. This well-known gel filtration material is commercially available from Bio-Rad Laboratories, Richmond, Calif.

The oligosaccharides also can be initially isolated from the t-PA glycoprotein by the method described by Rademacher and Dwek in co-pending application Ser. No. 772,988, filed Sept. 6, 1985, and assigned to a common assignee. Said method employs hydrazinolysis of the glycoprotein under reaction conditions to cause cleavage at the N-linked sites, producing a mixture having as a major component a de-N-acetylated hydrazone derivative of the oligosaccharides, followed by N-acylation of the hydrazone derivative, acid-catalysis of the hydrazone derivative to produce unreduced oligosaccharides, and subjecting the resulting unreduced oligosaccharides to cellulose column chromatography to remove contaminants and to recover the unreduced oligosaccharides. The latter materials, being essentially pure, can be used for attachment to various peptide or protein chains for further study.

Determination and characterization of the unique glycosylation pattern of t-PA derived from cultured normal human colon cells, including the structure, monosaccharide sequence and site location of the individual oligosaccharides on the polypeptide backbone, provides an important advance to medical science and technology. It facilitates the further study and use of oligosaccharide structural variations and alterations by deletion and/or attachment of specific sugar moieties on the t-PA protein molecule. It enables the preparation of homogeneous glycosylated t-PA from the protein backbone and any of these oligosaccharides. Modified t-PA glycoproteins can thus be prepared with varying stability, solubility, activity and other such properties. The serum half-life of the t-PA also can be extended by attaching certain terminal moieties to the oligosaccharide chain, for example, sialic acid which is a charged sugar molecule that prevents rapid filtration through the kidneys.

Antibodies to the individual oligosaccharides of the colon t-PA can be prepared and used in diagnostic assays. Biotin- and fluorescent-labeled probes can be prepared from the individual oligosaccharides of the colon t-PA and then used to identify the oligosaccharide receptors.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which:

Figure 3:
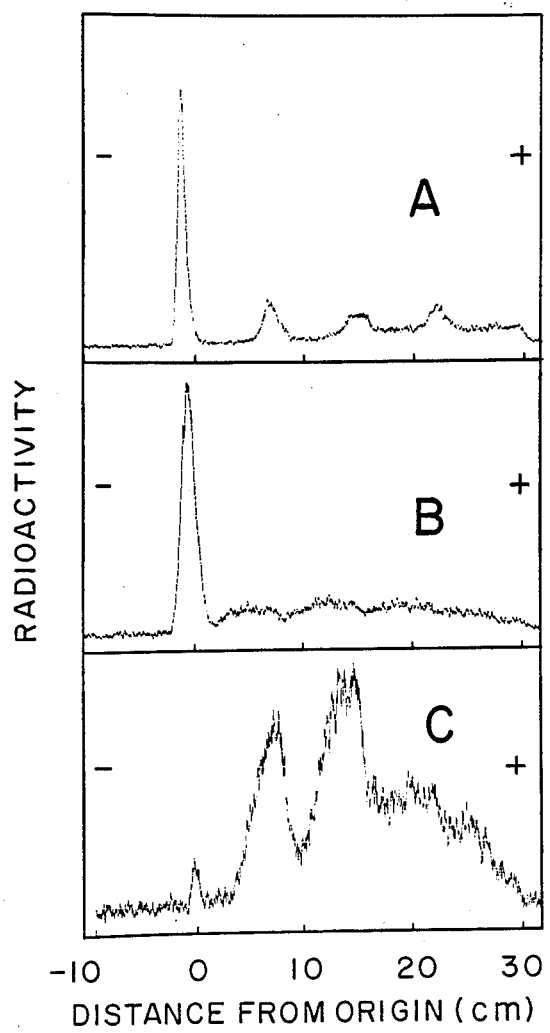

FIG. 3 is a graphical representation which shows the high-voltage paper electrophoresis of the radioactive oligosaccharides obtained by hydrazinolysis of melanoma-derived t-PA (A) before neuraminidase digestion (upper panel), (B) after incubation with *Arthrobacter ureafaciens* neuraminidase (middle panel), and (C) after repeat incubation with *Arthrobacter ureafaciens* neuraminidase of resistant acidic components (lower panel).

Figure 4B:
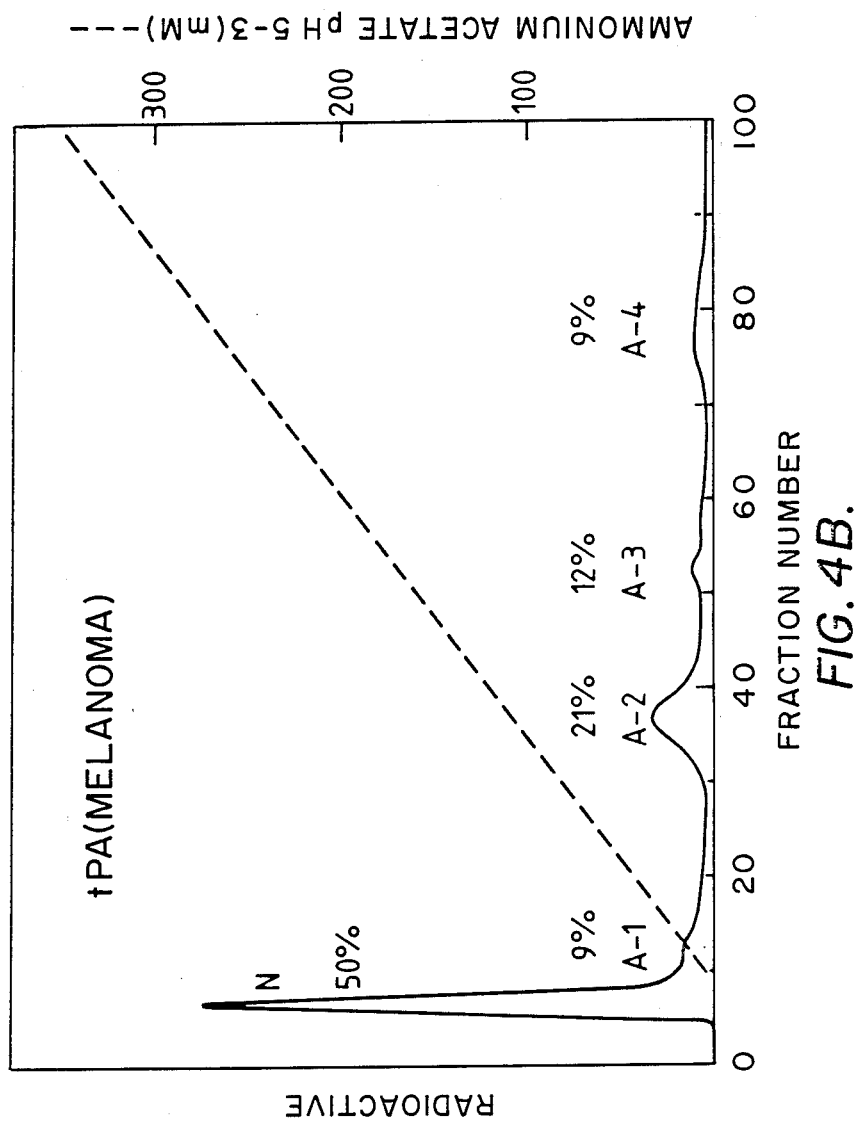

FIG. 4 is a graphical representation which shows the QAE-A25 Sephadex column charomatography profile of the radioactive oligosaccharides obtained by hydrazinolysis of (A) colon-derived t-PA (Upper panel) and (B) melanoma-derived t-PA (lower panel).

FIG. 5 is a graphical representation which shows the Bio-Gel P-4 column chromatography profile of the oligosaccharides from (A) colon-derived t-PA (upper panel) and (B) melanoma-derived t-PA (lower panel) after neuraminidase digestion. The arrows at the top indicate the elution positions of glucose oligomers; the numbers at the top indicate glucose units (g.u.); the letters at the bottom indicate oligosaccharide fractios.

FIG. 6 (A) and (B) shows the structures of the sixteen oligosaccharides liberated from colon-derived t-PA and their per cent molar ratio calculated on the basis of radioactivity incorporated in each oligosaccharide. For convenience, the oligosaccharides are also designated by shorthand notation C-A to C-J shown at the right side of the structures in FIG. 6.

Figure 7:
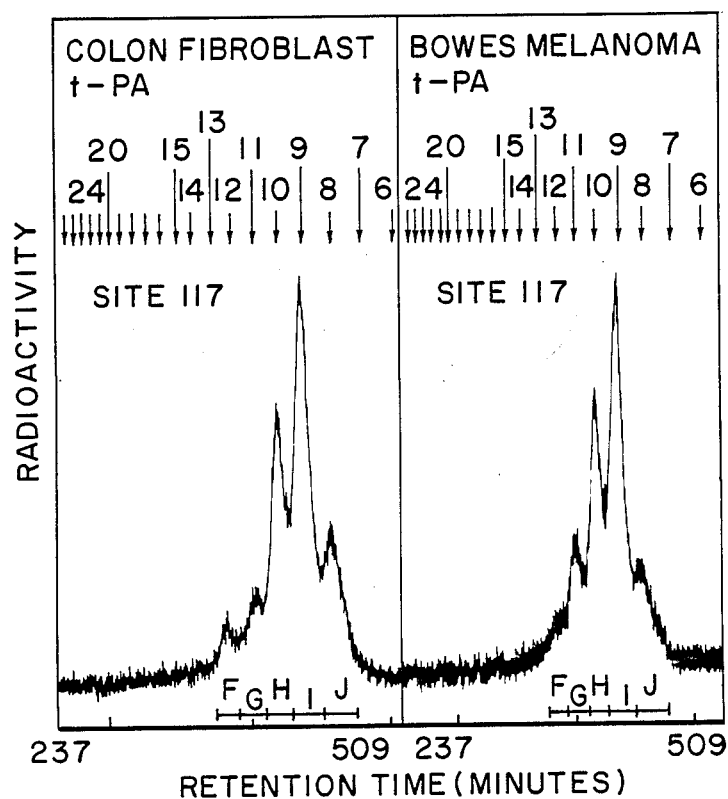
Figure 8:
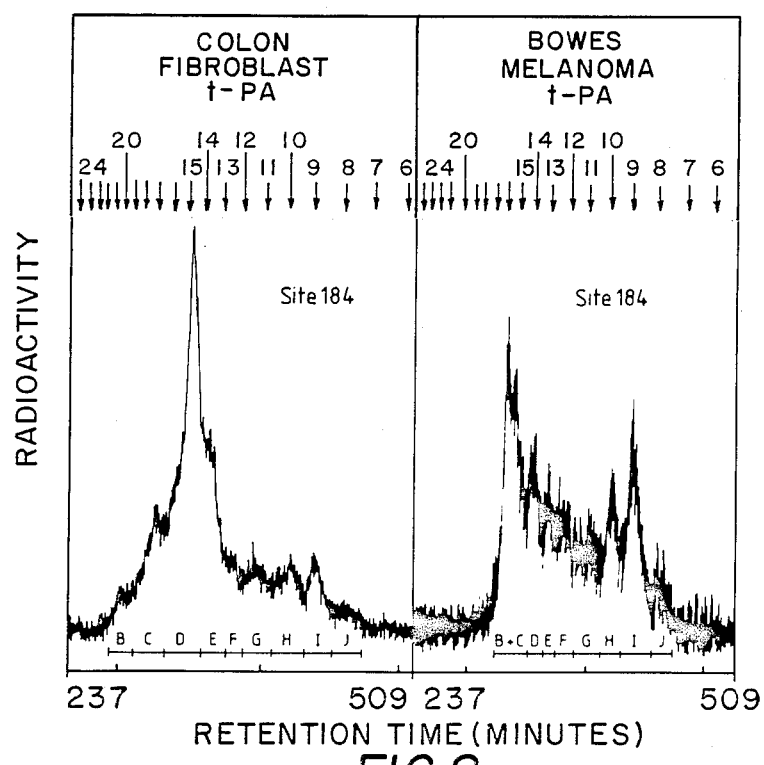
Figure 9:
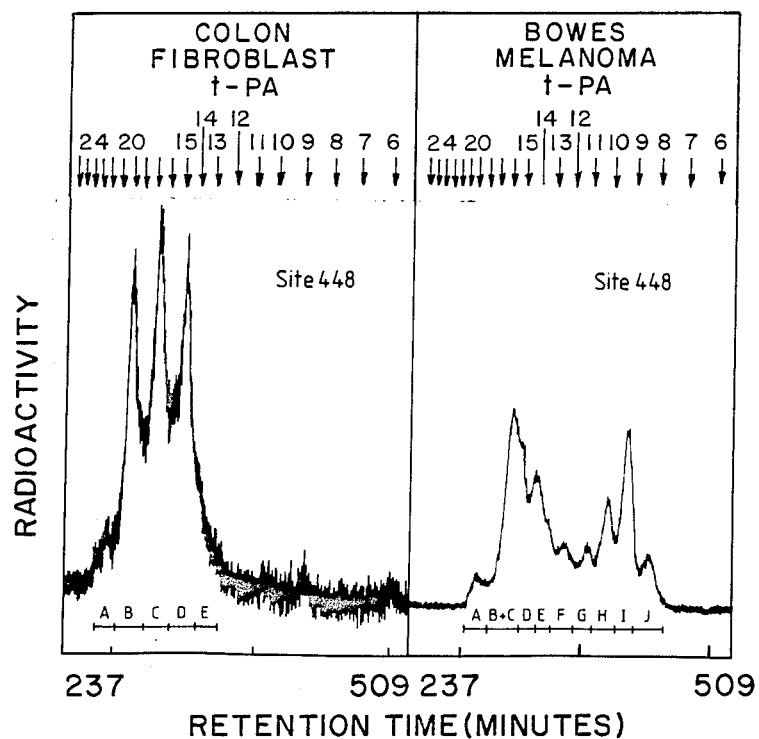

FIGS. 7 to 9 are graphical representations which show the Bio-Gel P-4 column chromatographic profiles of the oligosaccharides from tryptic peptides incorporating the glycosylation sites Asn-117 (FIG. 7), Asn-184 (FIG. 8) and Asn-448 (FIG. 9) for (A) colon-derived t-PA (left panels) and (B) melanoma-derived t-PA (right panels) after neuromannidase digestion. The arrows at the top indicate the elution positions of glucose oligomers; the numbers at the top indicate glucose units (g.u.); the letters at the bottom indicate oligosaccharide fractions.

Figure 10:
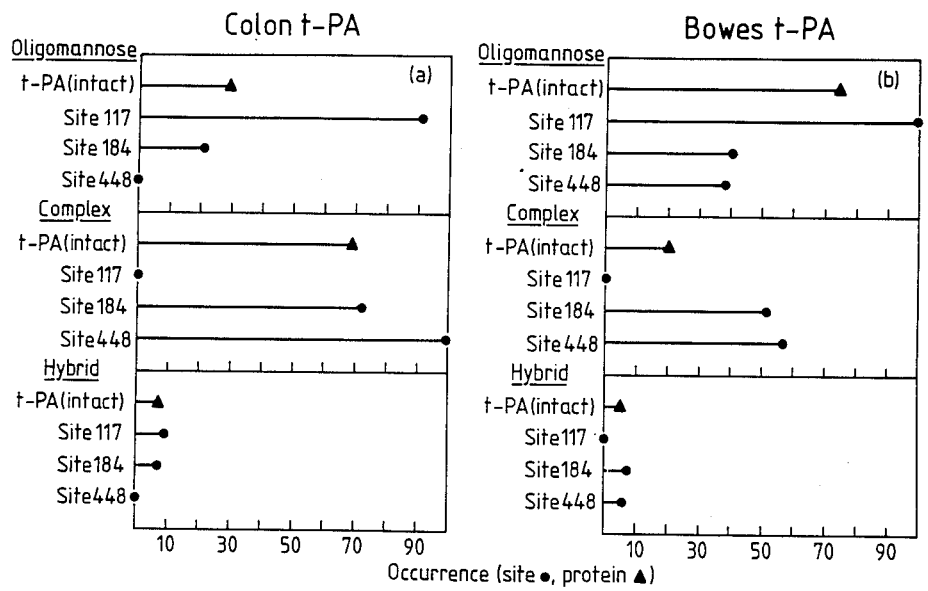

FIG. 10 is a bar chart which graphically shows for each of the individual glycosylation sites of FIGS. 7 to 9 and the intact t-PA glycoprotein the percentages of the oligosaccharides from (A) colon-derived t-PA (left panel) and from (B) melanoma-derived t-PA (right panel) which are complex, hybrid or oligomannose.

In these Figures and elsewhere herein, conventional carbohydrate abbreviations and nomenclature are used. Thus, the following symbols are used to indicate monosaccharide units and their residues in oligosaccharides:

| Glucose | Glc |
| Galactose | Gal |
| Mannose | Man |
| Fucose | Fuc |

Glyconic acids, glycuronic acids, 2-amino-2-deoxysaccharides, and their N-acetyl derivatives are designated by modified symbols. For example:

| N—Acetylglucosamine | GlcNAc |
| N—Acetylneuraminic acid | NeuNAc |

The position and nature of links between units are shown by numerals and the anomeric symbols $\alpha$ and $\beta$. Arrows are used to indicate the direction of the glycoside link with the arrow pointing away from the hemiacetal carbon of the link. For example, a common branched core in oligosaccharides with N-glycosidic protein links can be represented as follows:

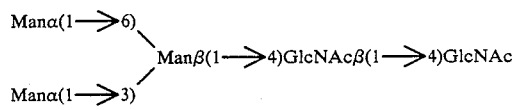

Amino acids also are shown by their conventional symbols. For example:

| L—Asparagine | Asn |
| L—Serine | Ser |
| L—Threonine | Thr |

The CCD-18Co cell line used in a preferred embodiment of this invention was originally cultured in CRCM medium with 20% fetal bovine serum and antibiotics. CRCM is a nutrient medium devloped by the American Type Culture Collection. During passage, the medium was changed to minimum essential medium (Eagle) with non-essential amino acids in Earle's BSS (balanced salt solution) supplemented with 10% fetal bovine serum. These cells also can be cultured in other well-known cell culture media such as basal medium Eagle's (BME), Dulbecco's modified Eagle medium (DMEM), medium 199, RPMI 1640 medium, and the like cell culture media such as described in detail by H. J. Morton, In Vitro 6, 89–108 (1970). These conventional culture media contain known amino acids, mineral salts, vitamins, hormones and carbohydrates. They are also frequently fortified with mammalian sera such as fetal bovine serum. Other components which are desirably used in the media are protein hydrolysates such as lactalbumin hydrolysate, tryptone, tryptose, peptone and the like materials.

Various other normal human colon fibroblast cell lines also can be used in accordance with the invention. Thus, another suitable normal human colon fibroblast cell line is the cell line designated CCD-112CoN which is available without restriction from the American Type Culture Collection under accession number ATCC CRL-1541.

Methods for the large scale growth of mammalian cells are well-known and these methods can be used for the culture of the colon cells defined herein. Such methods are described, for example, by Tolbert et al., *Biotech. Bioeng.* XXIV, 1671-1679 (1982); Tolbert and Feder, *Ann. Rept. Ferm. Proc.*, Vol. 6, Ch. 3, pp. 35–74 (1983); Harakas, *Ibid.*, Vol. 7, Ch. 7, pp. 159–211 (1984); and references cited in said publications. U.S. Pat. Nos. 4,166,768; 4,289,854; 4,335,215; and 4,537,860 disclose particularly useful methods and apparatus for the large scale growth and maintenance of cells for the production of plasminogen activators. The disclosures in said patents are incorporate herein by reference. The methods and apparatus disclosed therein can be used for the culture of the colon cells defined herein.

The cells are preferably cultured in nutrient medium at 37° C. in agitated microcarrier suspension culture as described in U.S. Pat. No. 4,335,215 and, after a suitable growth period, are maintained in the static maintenance reactor described in U.S. Pat. No. 4,537,860 in which the medium is supplemented with 0.5% lactalbumin hydrolysate.

Various modifications to the cell culture medium or the cells can be made to increase the yield of t-PA or extend the life of the colon cells used in the production of t-PA. Thus, conventional methods can be employed to minimize the effects of negative feedback on the biosynthesis of t-PA by adjustments to cell culture medium components and the t-PA product concentration as described, for example, by Kadouri and Bohak, *Adv. Biotechnol. Proc.* 5, 275–279, Eds. Mizraki and van Wezel, Alan R. Liss, Inc., Publ., 1985. Methods can be employed to maintain the cell line whereby it will grow indefinitely, for example, such as by frequent sub-culturing. So also, the genetic information from the colon cells can be inserted into another cell line for expression of the colon-derived t-PA by recombinant DNA methods.

Purification of the t-PA from the spent culture media can employ various known procedures for the separation of proteins such as, for example, salt and solvent fractionation, adsorption with colloidal materials, gel filtration, ion exchange chromatography, affinity chromatography, ion exchange chromatography, affinity chromatography, immunoaffinity chromatography, electrophoresis and high performance liquid chromatography (HPLC).

Procedures found to be particularly useful are affinity chromatography with zinc chelate-agarose, p-aminobenzamidine-agarose, concanavalin A-agarose (Con A-Sepharose TM), fibrin-Celite TM and fibrin-agarose (fibrin-Sepharose); HPLC with a TSK 3000 SW size exclusion column; and immunoaffinity chromatography with monoclonal antibodies.

Combinations of the above purification methods for isolation of t-PA are well-known. Thus, Rijken and Collen, *J. Biol. Chem.* 256 (13), 7035–7041 (1981), describe the use of affinity chromatography with zinc chelate-agarose and Con A-agarose, and gel filtration chromatography with Sephadex G-150. Rijken et al., *Biochim. Biophys. Acta* 580, 140–153 (1979), further describe use of the same chromatographic materials together with n-butyl-agarose chromatography. Husain et al., *Proc. Natl. Acad. Sci.* 78 (7), 4265–4369 (1981) teach the use of fibrin-Celite affinity chromatography to t-PA. Brouty-Boye et al., *Biotech.* December 1984, pp. 1058–1062, further disclose the use of affinity chromatography with Ultrogel AcA44 (LKB, Bromma, Sweden) and fibrin-Celite. The use of monoclonal antibodies to t-PA for the immunoadsorption chromatography of t-PA is described, for example, in UK Patent Application No. 2,122,219.

The zinc chelate-agarose can be prepared essentially as described by Rijken and Collen, *J. Biol. Chem.* 256 (13), 7035–7041 (1981) by coupling iminodiacetic acid to Sepharose ™ 4B and saturating this material with zinc chloride (7.3 mM), regenerating with 0.05M EDTA, pH 8.0, 0.05M $NH_4HCO_3$, pH 10.5, and water, and resaturating with zinc chloride. Sepharose 6B, an agarose gel in bead form, 60–140$\mu$ wet bead diameter, available from Pharmacia Fine Chemicals, Inc., Piscataway, N.J. can be used in place of the Sepharose 4B.

Con A-Sepharose is similarly available from Pharmacia Fine Chemicals, Inc., and is prepared by coupling concanavalin A to Sepharose 4B by the cyanogen bromide method.

Para-aminobenzamidine-agarose is commercially available from Pierce Chemical Co., Rockford, Ill. and Sigma Chemical Co., St. Louis, Mo.

The TSK 3000 SW size exclusion HPLC employs a column of hydrophilic, spherical silica. It is commercially available from Toyo Soda Manufacturing Co., Ltd., Yamaguchi, Japan, and Beckman Laboratories, Fullerton, Calif. A preferred TSK 3000 SW column is Spherogel-TSK 3000 SWG which has a pore size of 250 Å$\pm$5%, a particle size of 13$\pm$2$\mu$ and a molecular weight cutoff of 15,000–150,000.

The fibrin-Celite is a fibrin affinity matrix prepared from Celite filter-aid which is a diatomaceous earth (diatomite) commercially available from Manville Filtration & Minerals, Denver, Colo. This matrix can be prepared as described by Husain et al., *Proc. Natl. Acad. Sci. USA* 78, 4265–4269 (1981). According to this procedure, the Celite matrix surface is exposed to excess fibrinogen in a buffer and then to thrombin in a buffer to convert the fibrinogen to fibrin whereby the adsorptive surface is fully occupied by fibrin. Affinity chromatography on fibrin-Celite is used to remove non-fibrin binding proteins such as the urokinase plasminogen activator.

In the fibrin-Sepharose affinity chromatography, a matrix of fibrin is formed on Sepharose (agrose) instead of the Celite (diatomite).

In the immunoaffinity chromatography, monoclonal antibodies having an affinity for plasminogen activator are attached to polysaccharide beads which are then used as the chromatographic column. Monoclonal antibodies of Bowes t-PA and colon t-PA immobilized on Sepharose 4B have been found useful in this chromatographic procedure. Monoclonal antibodies can be made by adaptation of conventional procedures such as originally described by Köhler and Milstein, *Nature* 256, 495–497 (1975); *Eur. J. Immunol.* 6, 511–519 (1976). According to this method, tissue-culture adapted mouse myeloma cells are fused to spleen cells from immunized mice to obtain the hybrid cells that produce large amounts of a single antibody molecule. Further background information and detailed procedures for preparing monoclonal antibodies and their application in affinity chromatography can be had by reference to general texts in the field, for example, Goding, *Monoclonal Antibodies: Principles and Practices,* Academic Press, N.Y., 1983. Bowes t-PA monoclonal antibodies also are commercially available from American Diagnostica Inc., Greenwich, Conn.

Further methods of preparing the purified colon t-PA of this invention are described in copending application Ser. No. 849,933, filed Apr. 9, 1986, assigned to the common assignee and incorporated herein by reference.

The following examples will further illustrate the invention in greater detail although it will be appreciated that the invention is not limited to these specific examples.

The first example (Example 1) illustrates the production of t-PA from cultured normal human colon fibroblast cells on a large scale in sufficient quantities for initial animal testing.

The second and third examples (Examples 2 and 3) illustrate the significant differences between the colon t-PA of this invention and the Bowes melanoma t-PA of the prior art in their respective glycosylation patterns.

EXAMPLE 1

CCD-18Co cells obtained from the American Type Culture Collection (ATCC CRL-1459) were grown at 37° C. in attached culture in 75 cm$^2$ T-flasks using Dulbecco's MEM high glucose medium supplemented with 10% fetal bovine serum. The resulting cells were then cultured at 37° C. in the same medium in large scale microcarrier suspension culture by the method of U.S. Pat. No. 4,335,215 using Corning Geli-Bead microcarriers. The cells, after a suitable growth period to provide $1.5 \times 10^{11}$ cells attached to microcarriers, were then maintained at 37° C. in serum-free conditioned media supplemented with 0.25–0.5% lactalbumin hydrolysate (LAH) in the static maintenance reactor (SMR) system of U.S. Pat. No. 4,537,860. About 1673 liters of crude serum-free conditioned media was recovered for product purification during a 4 month run of the SMR system.

t-PA was recovered from the above conditioned media by successive purification steps consisting of: (1) affinity chromatography with zinc chelate-agarose by adsorption to and elution from zinc chelate-Sepharose, (2) affinity chromatography with Con A-agarose by adsorption to and gradient elution from Con A-Sepharose, (3) TSK 3000 SW size exclusion HPLC and (4) affinity chromatography with p-aminobenzamidine-agarose by adsorption to and elution from p-aminobenzamidine-agarose. A series of purification runs was made both with and without the latter affinity chromatography step.

The t-PA produced from normal human colon fibroblast cells (CCD-18Co) and recovered as described above was used in canine thrombolysis tests with two dogs. Prior to administration, the t-PA samples eluted from TSK 3000 SW size exclusion HPLC or the p-aminobenzamidine agarose affinity chromatography columns were dialyzed to prepare physiologically isotonic solutions. Sterile, pyrogen-free injectable grade water and saline (0.9% NaCl) was used for the preparation of all dialysis solutions and diluents. Isotonic solutions were obtained in two steps: first, dialysis was made against 0.3M NaCl, 0.01% Tween ™ 80, and second, the sample was diluted with an equal volume of 0.01% Tween 80 (polysorbate 80).

In the first dog trial, the t-PA sample was administered to a 20 Kg dog over a 60 minute period with an infusion rate of 1980 t-PA IU/min/kg with a total infusion of $2.38 \times 10^6$ t-PA IU. In the second dog trial, 3 t-PA samples were administered consecutively to a 25 kg dog over a 58 minute period with infusion rates of 1770, 1700 and 2380 t-PA IU/min/kg, respectively, with a total infusion of $2.91 \times 10^6$ t-PA IU. In 2 of the latter samples the p-aminobenzamidine agarose affinity chromatography step was omitted. In both trials, there were no significant decreases in fibrinogen levels following t-PA infusion compared to preinfusion values, thus demonstrating the fibrin specificity of the t-PA.

In accordance with these canine thrombolysis tests, an artificial thrombus was induced by advancing a $1 \times 3$ mm copper coil into the left anterior descending coronary artery distal to the first main diagonal branch. This procedure was carried out as described by Van de Werf et al., *Circulation* 69 (3), 605–613 (1984). An occlusive thrombus formed at the site of the coil. Presence and stability of the clot was confirmed by angiography. A 50 ml syringe pump was used to infuse t-PA solution via a midbody, intraveneous catheter over a 60-minute period. Blood samples for assay of fibrinogen, t-Pa antigen, and t-PA fibrinolytic activity were taken before t-PA infusion and at 5-minute intervals for 30 minutes following infusion.

In the second dog trial, the normal human colon t-PA was shown to be an effective thrombolytic agent in vivo without causing a systemic lytic state.

In the first dog trial, clot lysis was not observed. The reason for this is unclear, but several factors are believed to have been important. First, the nature of the test requires that a different dog and a different thrombus be used for each trial. It is known that canine thrombi are sometimes resistant to treatment with t-PA for unknown reasons. Secondly, heparin was not administered with this trial whereas it was given 25 minutes after the beginning of the t-PA infusion in the successful dog trial. Heparin is typically used in such trials to prevent reocclusion as reported by Bergmann et al., *Science* 220, 1181–1183 (1983); and Van de Werf et al., *Circulation* 69 (3), 605–610 (1984). Thirdly, the t-PA used in this trial was acid adjusted to pH 4 to improve its solubility and this may have caused the t-PA to be more susceptible to hepatic clearances. The half life of the t-PA following infusion was about 50% longer for the second dog trial than for the first dog trial.

EXAMPLE 2

Figure 1:
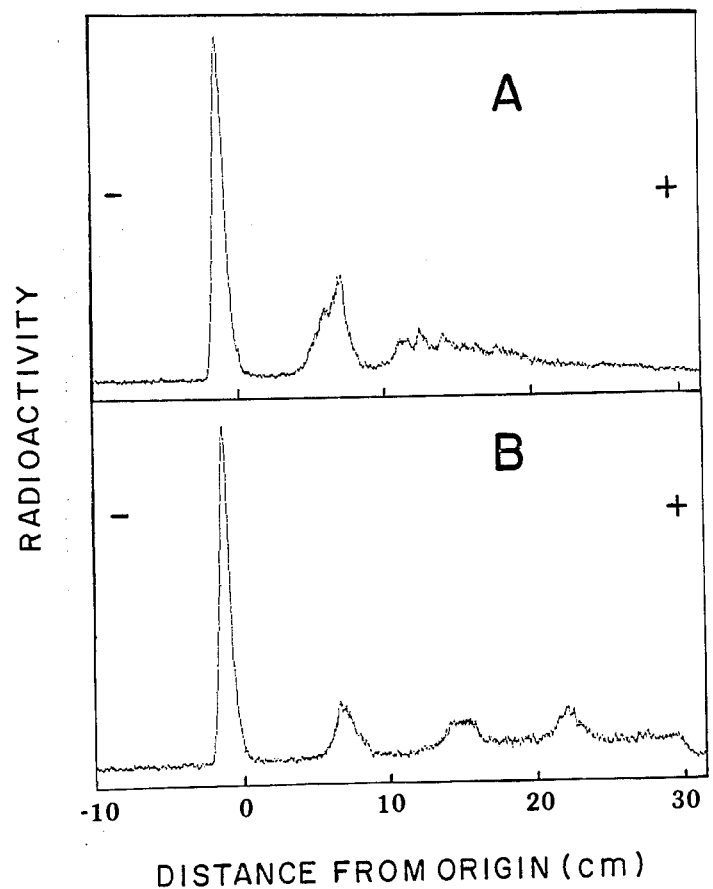
FIG. 1 is a graphical representation which shows the high-voltage paper electrophoresis of the radioactive oligosaccharides obtained by hydrazinolysis of (A) colon-derived t-PA (upper panel) and (B) melanoma-derived t-PA (lower panel).
Figure 2:
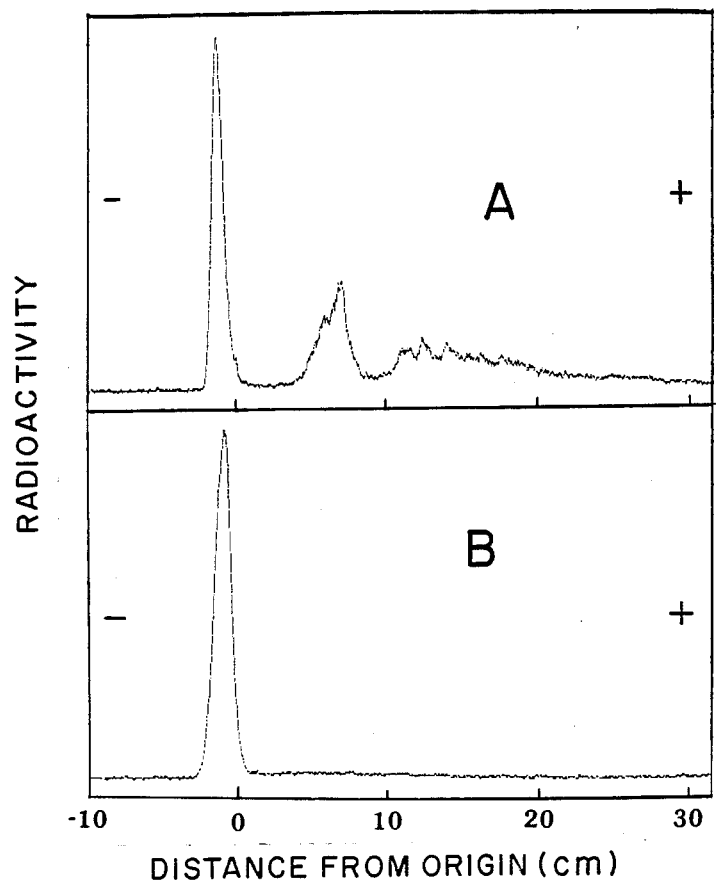
FIG. 2 is a graphical representation which shows the high-voltage paper electrophoresis of the radioactive oligosaccharides obtained by hydrazinolysis of colon-derived t-PA (A) before neuraminidase digestion (upper panel) and (B) after incubation with *Arthrobacter urefaciens* neuraminidase (lower panel).
Figure 5A:
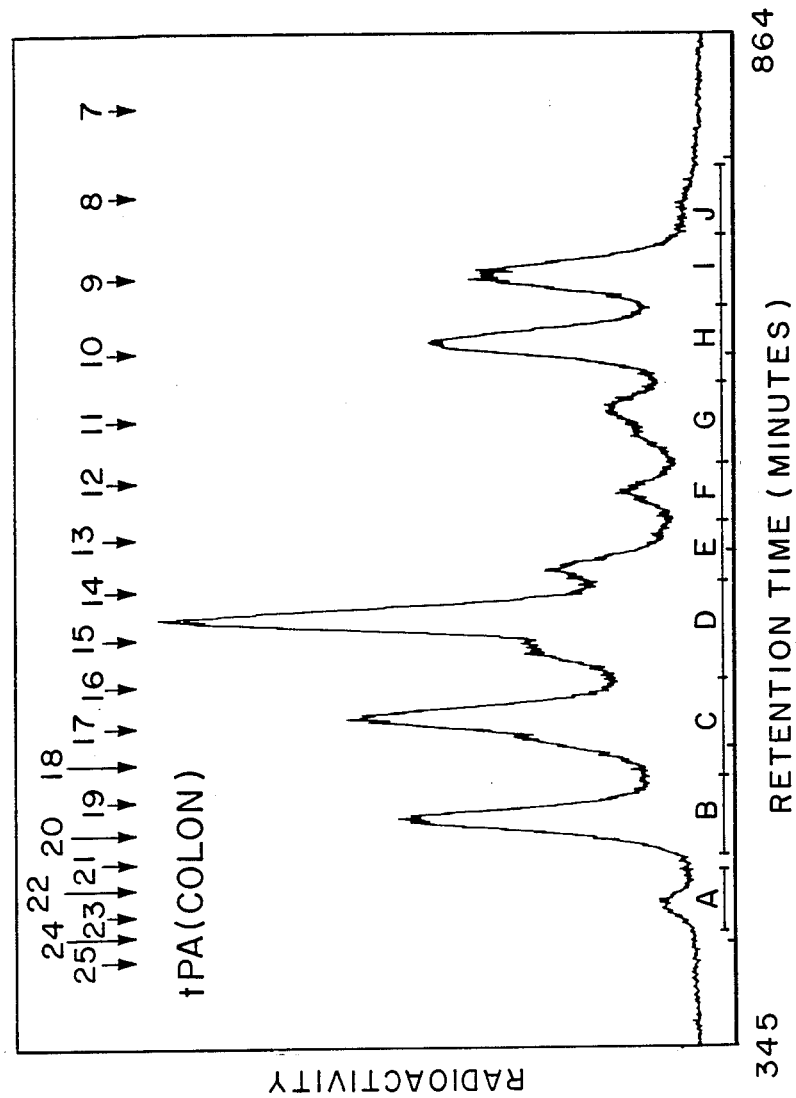
Figure 5B:
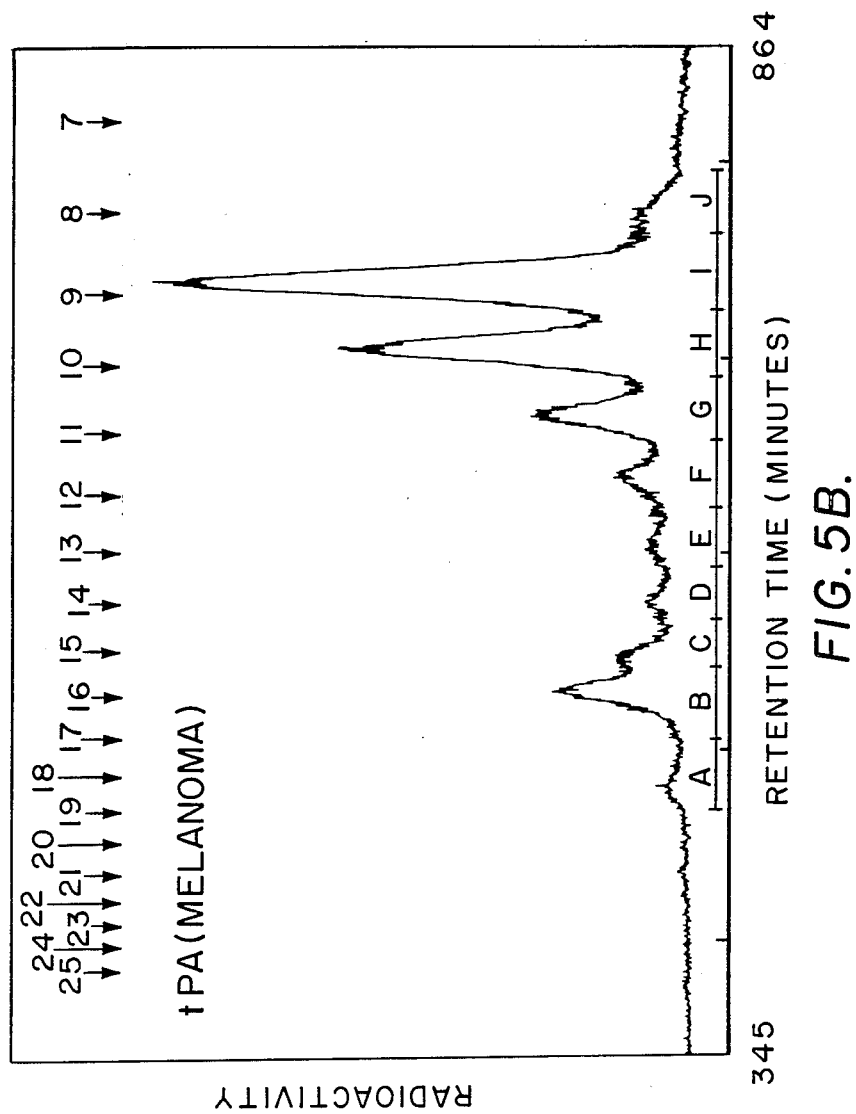
Figure 6A:
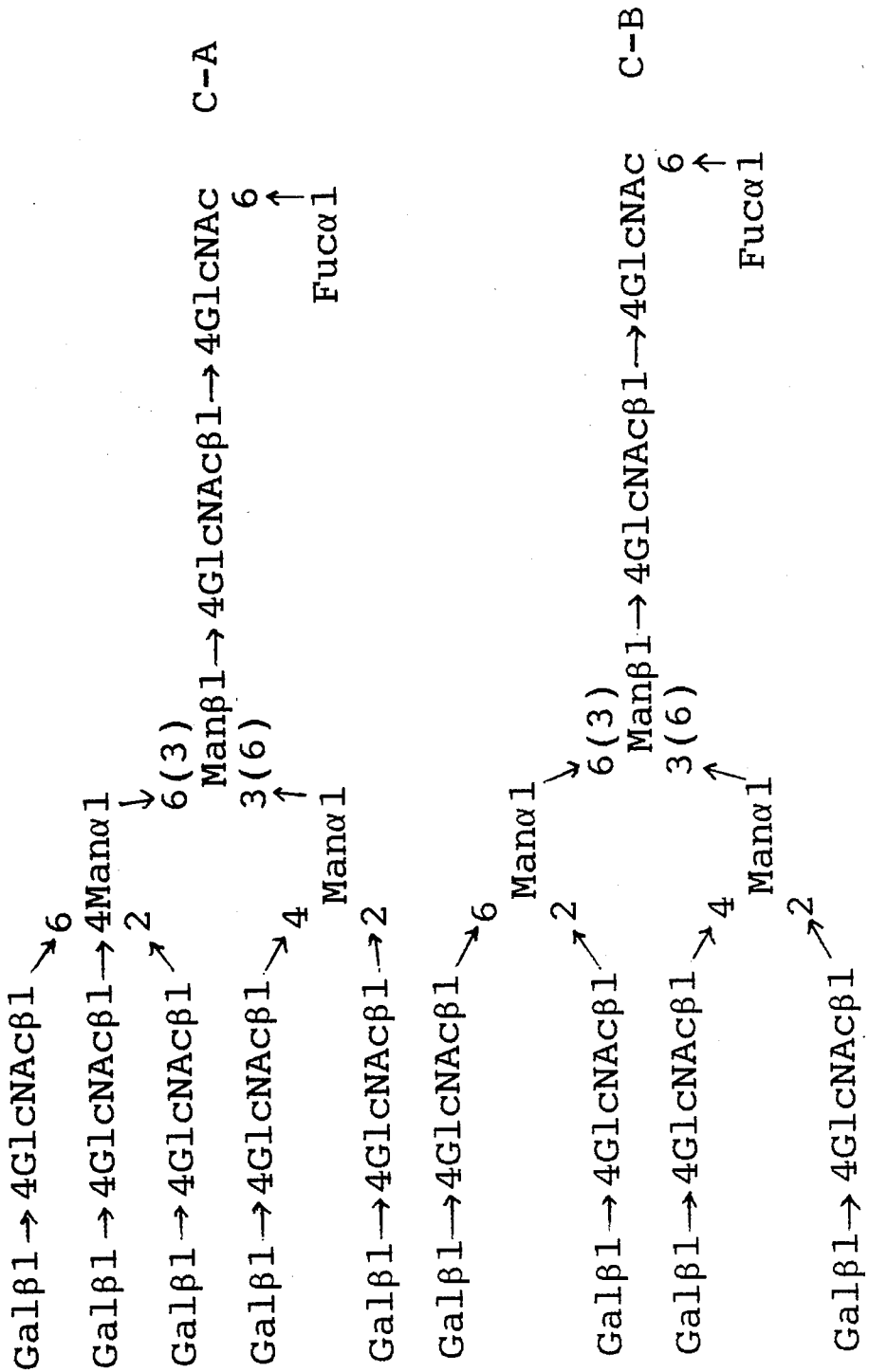
Figure 6B:
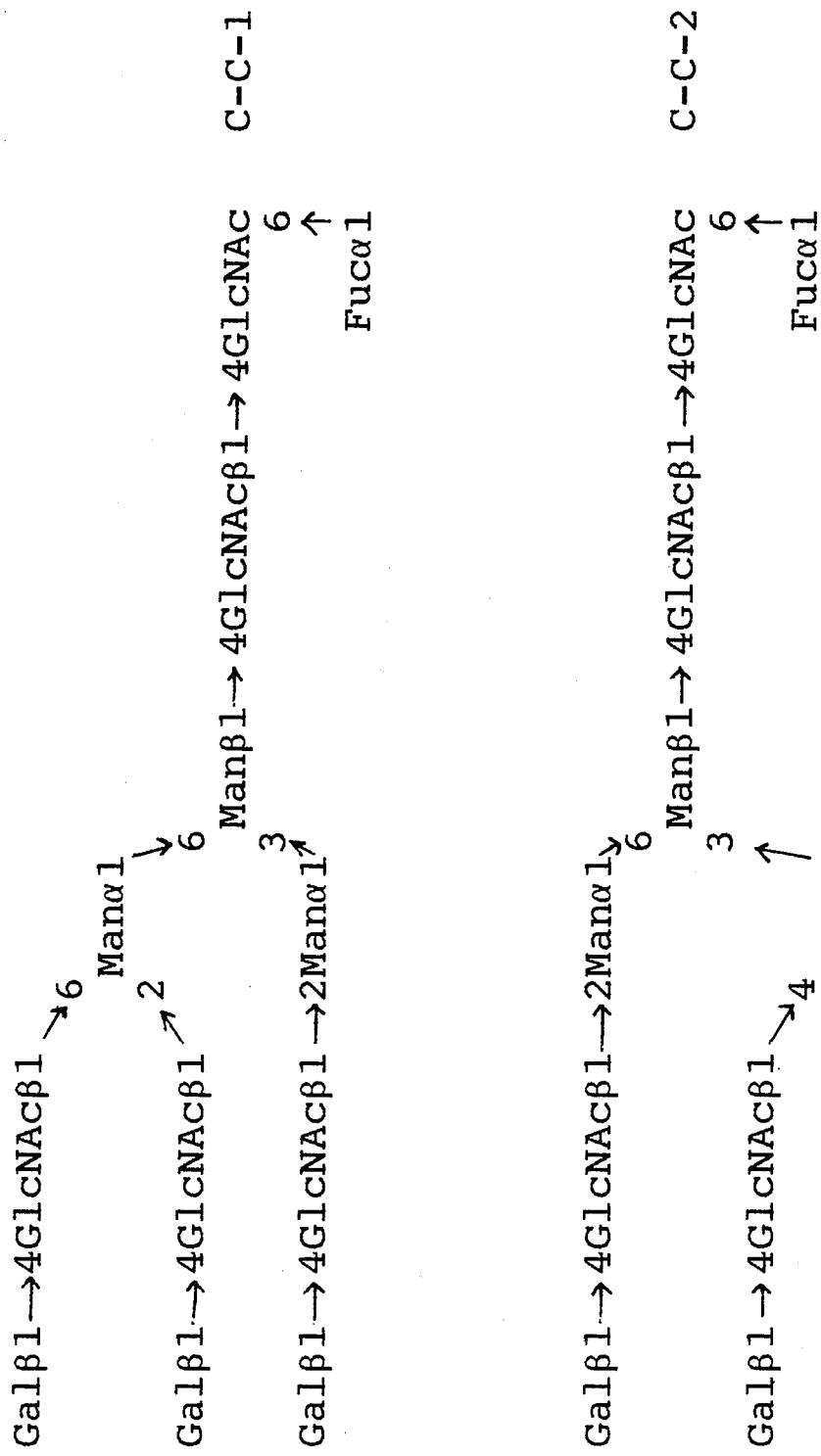
Figure 6C:
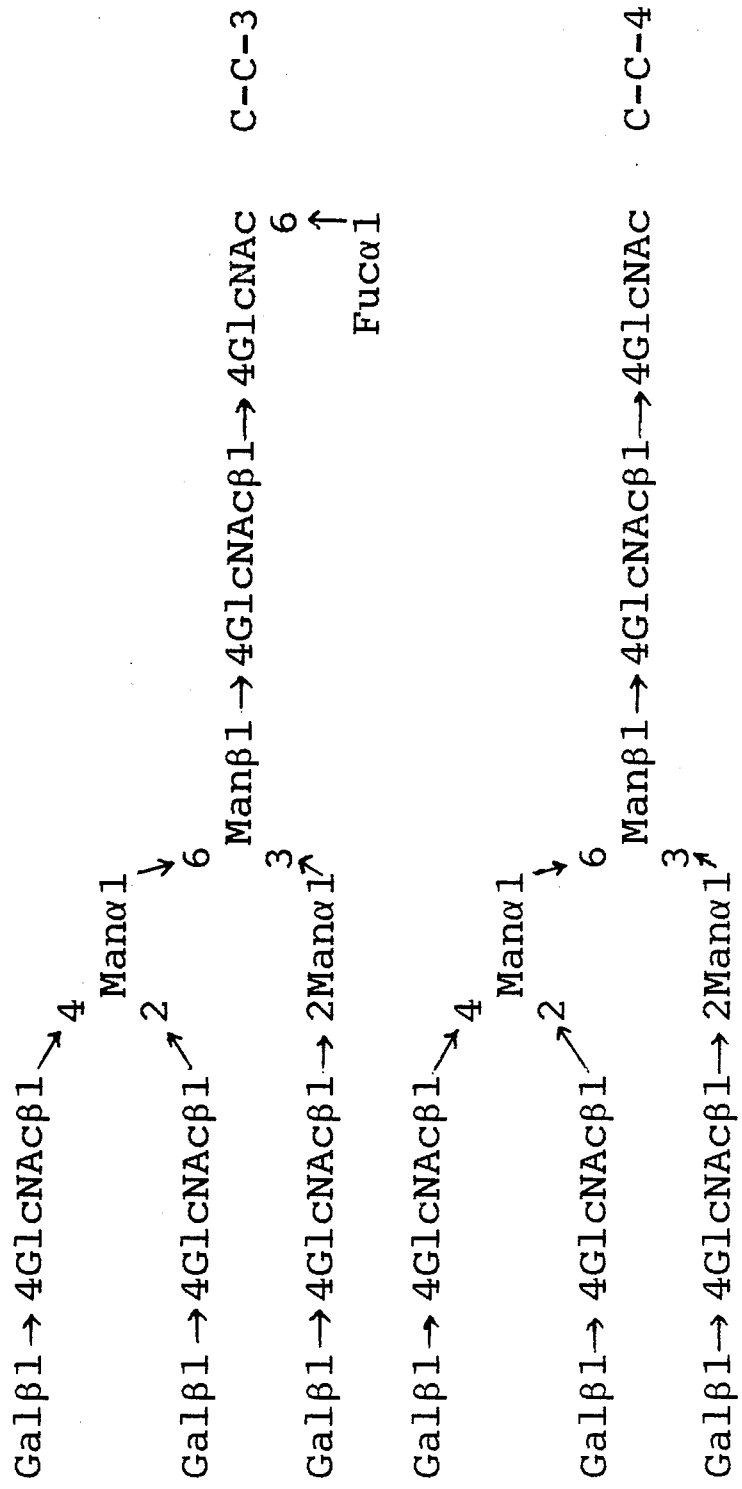
Figure 6E:
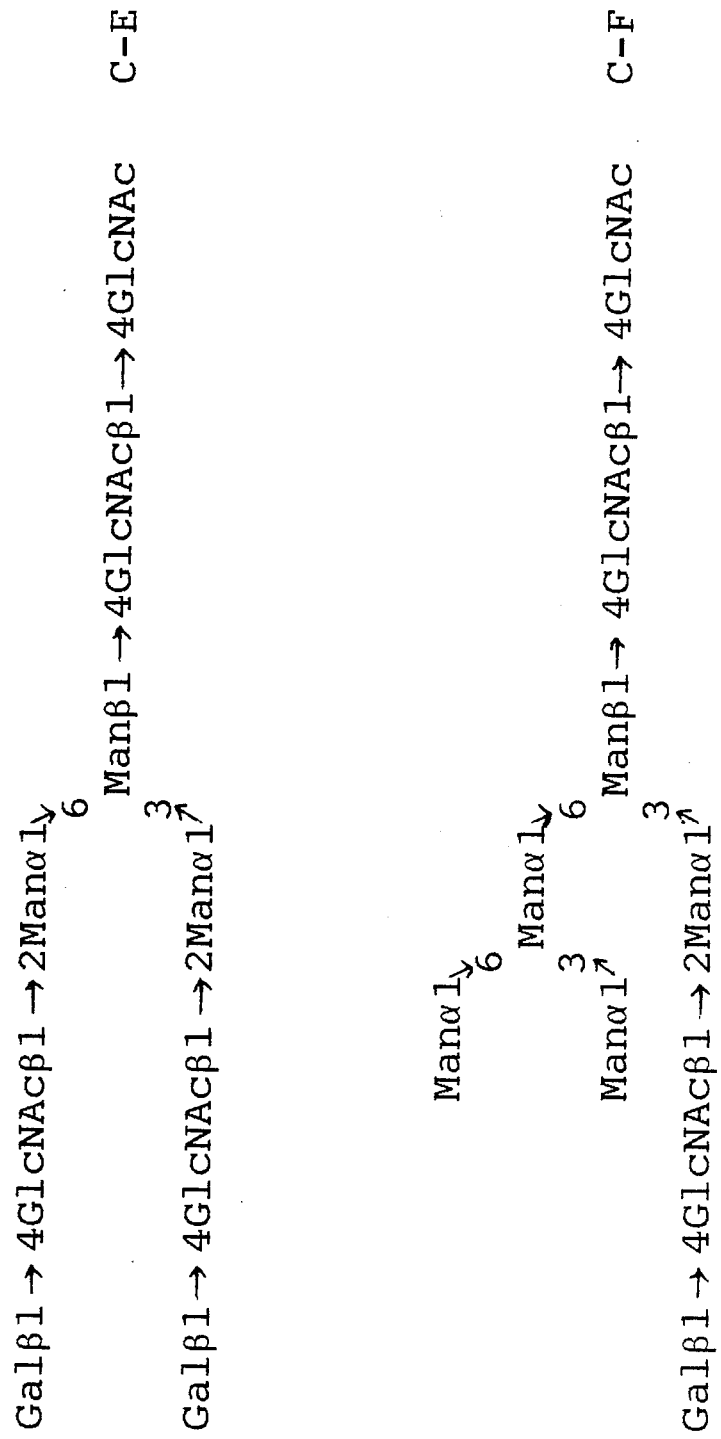
Figure 6F:
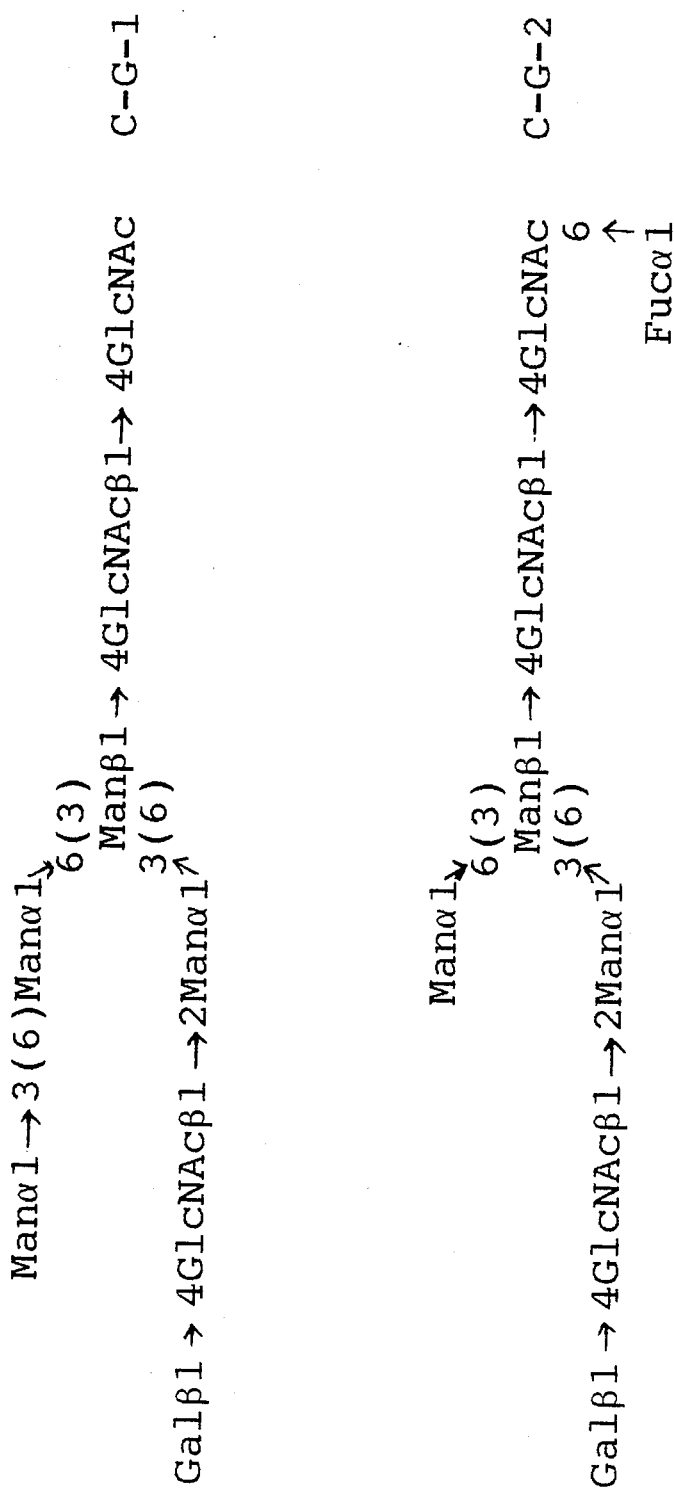
Figure 6G:
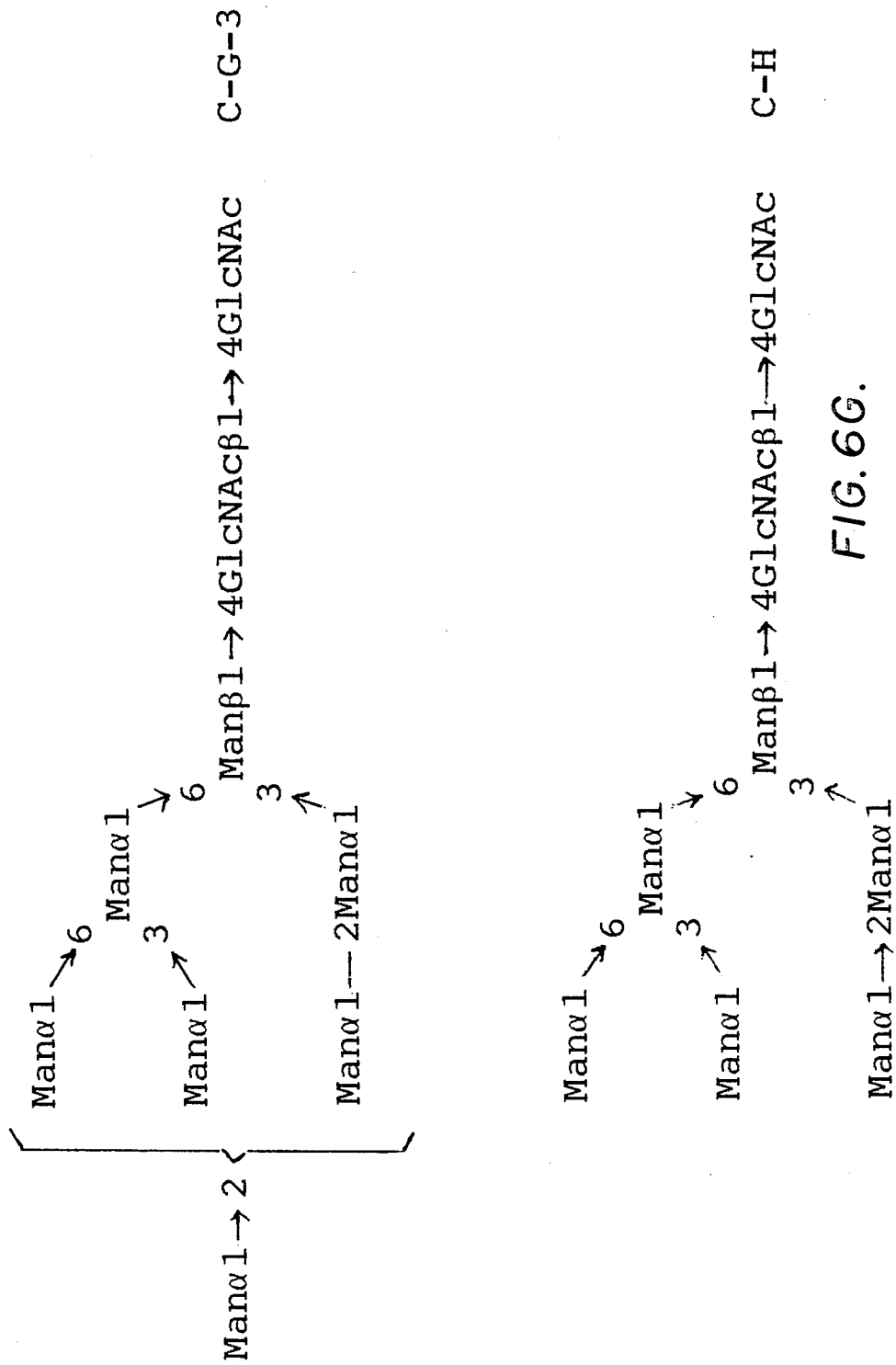
Figure 6H:
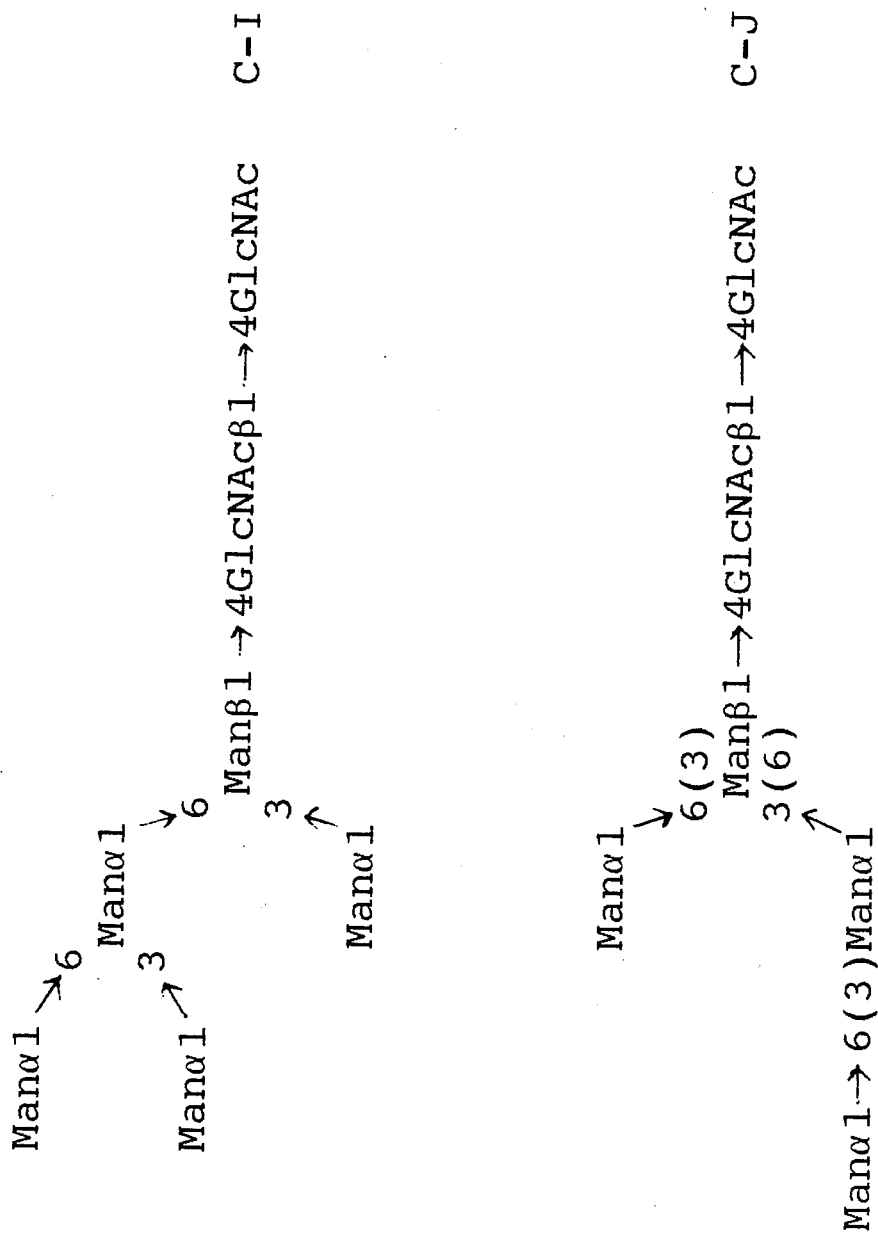

In order to demonstrate the unique glycosylation pattern of the colon t-PA as defined herein compared to the melanoma t-PA, the following determinations were made:

The asparagine-linked sugar chains of t-PA derived from human colon fibroblast CCD-18Co cells (C-tPA) and Bowes melanoma cells (B-tPA) were quantitatively released as oligosaccharides by hydrazinolysis and labeled by $NaB^3H_4$ reduction. High-voltage electrophoresis of the hydrazinolysates fractionated the oligosaccharides into four acidic components (A-1, A-2, A-3 and A-4) and a neutral component (FIG. 1). Neuraminidase digestion confirmed that the acidic components of C-tPA were exclusively sialic acid (FIG. 2). Only partial conversion of the acidic fractions to neutral species occurred after neuraminidase digestion of the B-tPA hydrazinolysate (FIG. 3). QAE-A25 Sephadex chromatography confirmed that monosialylated, disialyated, trisialylated and tetrasialylated oligosaccharides were present in the C-tPA hydrazinolysate (FIG. 4 and Table 1). After neuraminidase treatment, the Bio-Gel P-4 chromatograms indicated that the oligosaccharide structures on both C-tPA and B-tPA were heterogeneous and that the glycosylation pattern of C-tPA and B-tPA differed significantly (FIG. 5). Ten radioactive fractions were isolated from both C-tPA (C-A→C-J) (FIG. 5A and Table 2) and B-tPA (B-A→B-J) (FIG. 5B and Table 4).

The oligosaccharides from C-tPA were analyzed further in order to determine the monosaccharide sequences present. In total, sixteen oligosaccharides (FIG. 6 and Table 2) were isolated from the C-tPA fractions, with high-mannose (C-G-3, C-H, C-I and C-J), hybrid (C-B and C-C-1) and complex type including biantennary (C-D-2, C-E and C-C-2), triantennary (C-C-1, C-C-2, C-C-3 and C-C-4), tetraantennary (C-B) and pentaantennary (C-A) represented. Prominent features of these oligosaccharides include four isomeric forms of the triantennary complex type (i.e. additional outer chains at the C-4 or C-6 positions of the Man$\alpha$1→3 and the Man$\alpha$1→6 residues of the core) and the presence of a pentaantennary complex type. The oligosaccharide structures present on melanoma-derived t-PA (B-tPA) are predominantly of the high mannose type as seen from the elution positions (FIG. 5B). See also the finding of Pohl et al., that the glycopeptides of Bowes melanoma t-PA contain high mannose structure at Asn-117 and two complex sugar structures at Asn-184 and Asn-448, "EMBO Workshop on Plasminogen Activators," Amalfi, Italy, Oct. 14–18, 1985.

The Bowes melanoma 2-chain t-PA (product #110, lot 16-01) was purchased from American Diagnostica Inc., Greenwich, Conn. and further purified by p-aminobenzamidine-agarose affinity chromatography to remove low molecular weight contaminants visible on sodium dodecylsulfate polyacrylamide gel electrophoresis gels. According to the manufacturer, the Bowes melanoma t-PA is purified from serum-free conditioned medium by adsorption to and elution from PAM-2 Sepharose ™ immobilized Bowes melanoma t-PA monoclonal antibody, followed by gel filtration on Sephadex ™ G-150.

The colon t-PA was purified from serum-free conditioned medium obtained by the culture of CCD-18Co cells as described in Example 1, above. The purification steps consisted of: (1) adsorption to and elution from zinc chelate-Sepharose, (2) adsorption to and gradient elution from Con A-Sepharose, (3) TSK 3000 SW HPLC gel filtration, and (4) adsorption to and elution from p-aminobenzamidine agarose.

Prior to use, the purified t-PA sample was adjusted to pH 4 and stored sterile in the refrigerator (sample A). Another sample was stored frozen at neutral pH before use (sample B).

A third colon t-PA sample (sample C) was purified from the serum-free conditioned media obtained by the culture of CCD-18Co cells substantially as described in Example 1, above, except that the culture medium was not supplemented with the lactalbumin hydrolysate. A different purification sequence also was employed for sample C. The purification steps consisted of: (1) adsorption to and elution from zinc chelate-Sepharose, (2) adsorption to and elution from p-aminobenzamidine-agarose, (3) batch adsorption to and elution from PAM-2 Sepharose, an immobilized Bowes melanoma t-PA monoclonal antibody purchased from American Diagnostica Inc., and (4) TSK 3000 SW HPLC gel filtration.

The following parts I to VI and the structural analysis of oligosaccharides was carried out on sample A, above. The structures of the sixteen oligosaccharides C-A to C-J shown below correspond to the structures shown in FIG. 6 but with dotted lines indicating the several enzymatic cleavage points.

The purification procedure for colon t-PA sample A is described in further detail as follows:

Purification of Sample A

General

The purification followed part of the general procedure and sequence given by Rijken and Collen, *J. Biol. Chem.* 256, 7035–7041 (1981), scaled up to accomodate larger volumes. TSK 3000 SW HPLC was used in place of Sephadex G-150 size exclusion to give a dramatic improvement in speed of processing. Chromatography on p-aminobenzamidine-agarose was included as a final step to give a more highly purified product. Protein determinations were by the method of Bradford, *Anal. Biochem.* 12, 248–754 (1976) using reagents obtained from Bio-Rad. Bovine serum albumin was used as standard. SDS polyacrylamide gel electrophoresis (SDS-PAGE) was conducted according to the method of Laemmli, *Nature* 227, 660–665 (1970), using 5–15% gradient gels. The sample buffer contained 25 mM dithiothreitol for reduced samples. Molecular weight standards were obtained from Pharmacia. Gels were stained with silver nitrate using reagents from Bio-Rad. Activity of final preparations were measured using the amidolytic substrate S-2288 (H-D-Ile-Pro-Arg-paranitroanalide, Kabi) and are given in international units relative to the WHO t-PA standard. The assay mixture (200 μl) contained 50 mM Tris HCl, 0.01% sodium azide, 0.001% Tween 80, 1 mM S-2288, pH 8.7, and t-PA sample or standard as appropriate. For routine screening of column fractions for activity an amidolytic assay employing the substrate S-2322 (H-D-Val-Gly-Arg-paranitroanilide, Kabi) was used. The assay mixture (100 μl) contained 20 mM Tris HCl, pH 7.6, 100 mM NaCl, 0.01% Tween 80, 100 μg/ml bovine serum albumin, and enzyme.

In both assays, activity was measured by the increase in absorbance of the assay mixture at 410 nm. A commercially available ELISA for t-PA (Immubind, American Diagnostica) was purchased in kit form and used to measure t-PA antigen. Zinc chelate-Sepharose Chromatography One-hundred forty liters of serum-free medium containing 0.25% lactabumin hydrolysate were conditioned by CCD-18Co cells in the static maintenance reactor. Following addition of 100 units/ml penicillin and 100 μl/ml streptomycin, the conditioned medium was batch adsorbed in two portions (40 and 100 liters) by stirring for three hours with a total of 4.4 liters of Zinc-charged chelating Sepharose-6B (Pharmacia) previously equilibrated with 1M NaCl, 20 mM Tris HCl, 0.01% Tween 80, pH 7.5. For each batch, the resin was transferred to a 10 cm diameter column, washed with about 7 liters of equilibration buffer at 2.7 liters/hr flow rate and the plasminogen activator eluted by gravity flow using about 2 liters of equilibration buffer containing 50 mM imidazole. NaN₃ (0.02%) was added to the eluted fraction.

Con A-Sepharose Chromatography

The pooled plasminogen activator-containing Zinc chelate-Sepharose eluate (3.6 liters) was applied to a 4.4×12.8 cm column of Concanavalin A-Sepaharose-4B (Pharmacia) previously equilibrated with 1M NaCl, 10 mM potassium phosphate, 0.01% Tween 80, pH 7.5. After washing with equilibration buffer, the column was eluted at 160 ml/hr with a linear gradient of equilibration buffer (1000 ml) to 2M KSCN, 0.4M α-D-methylmannoside, 10 mM potassium phosphate, 0.01% Tween 80, pH 7.5 (1000 ml). Fractions of 13 ml volume were collected. The peak fractions (650 ml volume) were dialyzed against three 10 liter portions of 0.01% Tween 80 and lyophilized. TSK 3000 SW HPLC Gel Filtration The lyophilized peak fractions from Con A-Sepharose chromatography were dissolved in a minimum volume of H₂O (21 ml final volume) and applied in four portions to a 2.15×60 cm Spherogel-TSK 3000 SW HPLC column (Beckman Instruments, Inc.) at 5 ml/min flow rate and at room temperature. The column was equilibrated and eluted with 1.6M KSCN, 20 mM sodium phosphate buffer, pH 6.8, containing 0.01% Tween 80. Fractions (4 ml) were collected and the peak fractions (75 ml total volume) were pooled and dialyzed against 0.3M NaCl, 0.01% Tween 80.

p-Aminobenzamidine-Agarose Chromatography

The dialyzed TSK 3000 SW fractions were applied at room temperature and 1 ml/min flow rate to a 1.2×10 cm column of p-aminobenzamidine-agarose (Pierce Chemical Company) previously equilibrated with 0.5M NaCl, 50 mM Tris HCl, 0.01% Tween 80, pH 8.0. The column was washed with the equilibration buffer until the absorbance at 280 nm of the effluent reached baseline. The plasminogen activator was then eluted in a volume of 12 ml with equilibration buffer containing 2M KSCN.

Dialysis, Filtration and Final Preparation.

Since this preparation was originally intended for in vivo tests, it was next processed to prepare an isotonic, sterile solution. The p-amino-benzamidine-agarose eluate was dialyzed against 1000 ml 0.15 M NaCl, 0.01% Tween 80, during which time substantial amounts of precipitate formed. The preparation was then dialyzed against 1000 ml of 0.15M NaCl, 0.01% Tween 80, 0.35 mM acetic acid, pH 4.1, and then against 1000 ml of 0.15M NaCl, 0.01% Tween 80, without any acetic acid. Some precipitate still remained after these dialyses. The preparation was then diluted by addition of about 12 ml of 0.15M NaCl, 0.01% Tween 80, 0.88 mM acetic acid, to give 24 ml of slightly cloudy solution with a pH of 4.2. It was then sterile filtered and stored for about 4 months at 4° C. After this extended period, 15 ml of this preparation was adjusted to neutral pH, solid KSCN was added to give a 1.6M solution, and the sample concentrated to about 1.4 ml in an Amicon ultrafiltration cell using a YM05 membrane. The concentrate was then applied to a small column of Sephadex G-25 (PD-10 column, Pharmacia) equilibrated with 1M NH₄HCO₃ and eluted with this same buffer. Fractions of 0.5 ml were collected and the peak fractions (1.5 ml) represented the final product. One ml of this solution was lyophilized directly in the glass tube used for hydrazinolysis and submitted for oligosaccharide analysis.

Preparation of Bowes Melanoma t-PA

The Bowes melanoma t-PA was commercially supplied by the manufacturer as a frozen solution in 1M NH₄HCO₃. About 1.6 ml (1.5 mg) of melanoma t-PA was diluted with 15 ml of 0.5M NaCl, 50 mM Tris HCl, 0.01% Tween 80, pH 8.0. The t-PA was then adsorbed to and eluted from a 1×10 cm column of p-aminobenzamidine-agarose as described above for sample A, except that 1M arginine, instead of 2M KSCN, was used in the elution buffer. The active fractions were combined, concentrated, and the buffer exchanged to 1M $NH_4HCO_3$ as described for sample A. Recovery was 1.3 mg of t-PA in 2.0 ml volume. One ml of the final preparation was lyophilized in a hydrazinolysis tube and used for oligosaccharide analysis.

The specific activity of sample A expressed in terms of S-2288 amidolytic activity was 299,000 I.U./mg. The Bowes melanoma t-PA sample had a corresponding activity of 375,000 I.U./mg. The ratio of t-PA antigen (as measured by ELISA) to total protein agreed to within 2% for these two samples. Thus, these preparations were free from major contaminants and possessed similar in vitro activities.

I Fractionation and Purification of Asparagine-Linked Sugar Chains of Colon and Bowes Melanoma Derived Tissue Plasminogen Activator (t-PA) Hydrazinolysis Purified t-PA (~150 μg, colon fibroblast and Bowes melanoma) were dialysed exhaustively against distilled water (4° C.) and cryogenically dried over activated charcoal at −196° C. ($<10^{-6}$ bar). The t-PA samples were suspended in 250 μl of freshly distilled anhydrous hydrazine under an anhydrous argon atmosphere. The temperature was raised 12° C./hour from 30° C. to 85° C. and then maintained at 85° C. for a further 10 hours. The hydrazine was removed by evaporation under reduced pressure ($<10^{-5}$bar) at 25° C. followed by repeated (5X) flash evaporation from anhydrous toluene.

N-acetylation

The hydrazinolysates were N-acetylated by the addition of excess acetic anhydride in saturated $NaHCO_3$ at 4° C. for 10 min. The temperature was then raised to 25° C. and a second aliquot of acetic anhydride was added. The reaction was allowed to proceed for 50 minutes.

Purification of Oligosaccharides

Following N-acetylation the samples were applied to a column of Dowex AG 50×12 (H+), eluted with water and evaporated to dryness (27° C.). The desalted samples were dissolved in water and applied to Whatmann 3MM chromatography paper. Descending paper chromatography (27° C.) was subsequently performed using n-butanol/ethanol/water (4:1:1 v/v) (solvent I). After 48 hours the first five centimeters measured from the origin was eluted with $H_2O$.

Tritium Labelling of Oligosaccharides

The oligosaccharides so isolated were flash-evaporated to dryness (27° C.) and reduced with a five-fold molar excess of $NaB^3H_4$ (70 Ci/mmol NEN, New England Nuclear) in 50 mM NaOH adjusted to pH 11.2 with saturated boric acid (30° C., 4 hr). An equivalent volume of 1M $NaB^3H_4$ in NaOH/boric acid (Ph 11.2) was then added and incubation continued for a further 2 hr. The mixture was then acidified (pH 4-5) with 1M acetic acid and applied to a Dowex AG 50 ×12 (H+) column, eluted with water, evaporated to dryness (27° C.) and flash-evaporated (27° C.) from methanol (X5). The samples were then applied to Whatmann 3 MM paper and subjected to descending paper chromatography for 2 days using solvent I. Radiochromatogram scanning was performed with a Berthold radiochromatogram scanner LB230. The radioactivity (first 5 cm) was subsequently eluted with water and counted.

Neuraminidase Treatment of Oligosaccharides (Asialo Oligosaccharides)

An aliquot of the reduced ($^3H$) labeled oligosaccharides so isolated was subjected to exhaustive neuraminidase digestion as described in part III, below. The samples were then subjected to high-voltage paper electrophoresis at 80 V/cm in pyridine/acetic acid/water (3:1:387 v/v, pH 5.4) (FIG. 1). The radioactivity at the origin were recovered from paper by elution with water, desalted using a layered column of Chelex 100 (Na+)/Dowex Ag50×12 (H+)/AG3×4A(OH−)-/QAE-A25 Sephadex, eluted in water, evaporated to dryness and resuspended in 175 μl of a 20 mg/ml partial dextran hydrolysate.

II Exoglycosidase Purification and Specificity jack bean β-N-acetylhexosaminidase and Jack bean α-mannosidase were purchased from the Sigma Chemical Company (Poole, England) and further purified by adaptation of the method of Li and Li, *Meth. Enzym.* 28, 706 (1972). Jack bean β-N-acetylhexosaminidase cleaves all non-reducing terminal β-linked GlcNAc residues. Jack bean α-mannosidase will liberate one mannose from R-Manα1→6(Manα→3)R' but none from R-Manα1→3(Manα1''6)R' [R≠H] as described by Yamashita et al., *J. Biol. Chem.* 255, 5635 (1980). Jack bean β-galactosidase was purified from Jack bean meal and cleaves all non-reducing terminal galactose residues linked via a β1→4 glycosidic bond. β-N-acetylhexosaminidase from *Streptococcus pneumonia* was purified by adaptation of the procedure of Glasgow et al, *J. Biol. Chem.* 252, 8615 (1977). This enzyme will cleave a non-reducing terminal G1cNAc residue if this is part of the structure.

where R can be either H or GlcNAcβ1→4 as described by Yamashita, *Biochem. Biophys. Res. Commun.* 100, 226 (1981). α1→2 Mannosidase from *Aspergillus phoenicis* was purified by adaptation of the procedure of Ichishima et al, *Biochem. Biophys. Acta* 658 45 (1981). This enzyme will release non-reducing terminal mannose residues only if these are linked to the parent oligosaccharide via an α1→2 glycosidic bond as described by Yamashita et al., *Biochem. Biophys. Res. Commun.* 96, 1335 (1980). The following exoglycosidases were obtained from commercial sources in a form sufficiently pure for sequence analysis: α-fucosidase from bovine epidydimis (Sigma Chemical Company, Poole, England), β-mannosidase from snail (Seikagaku Kogyo Company, Tokyo, Japan), and neuraminidase from *Arthrobacter ureafaciens* (Calbiochem).

III Enzymatic Digestion of Oligosaccharides

Radioactive oligosaccharides [1–500×$10^4$ cpm] were incubated with one of the following enzyme solutions at 37° C. for 18 h (one unit of exoglycosidase will hydrolyse 1 μmole of the synthetic substrate per minute). (i) jack bean β-galactosidase: 6 units ml$^{-1}$ in 0.1M citrate/phosphate buffer, pH 4.0; (ii) jack bean β-N-acetylhexosaminidase: 10 units ml$^{-1}$ in 0.1M citrate buffer, pH 5.0; (iii) *Streptococcus pneumoniae* β-N-acetylhexosaminidase: 0.2 units ml$^{-1}$ in 0.1M citrate phosphate buffer, pH 6.0; (iv) jack bean α-mannosidase: 10 units ml$^{-1}$ in 0.1M acetate buffer, pH 5.0; (v) *Aspergillus phoenicis* α1→2 mannosidase: 5 μg ml$^{-1}$ in 0.1M acetate buffer, pH 5.0; (vi) bovine epidydimal α-fucosidase: 2 units ml$^{-1}$ in 0.2M citrate/phosphate buffer, pH 6.0; (vii) snail β-mannosidase: 0.5 units ml$^{-1}$ in 0.5M citrate buffer, pH 4.5; (viii) *Arthrobacter ureafaciens* neuraminidase: 10 units ml$^{-1}$ in 0.1M acetate buffer, pH 5.0. All digestions were performed at a concentration of 10$^5$ cpm/5 μl total reaction volume. Where less than 10$^5$ cpm of oligosaccharide was available, the oligosaccharide was dissolved in 5 μl of the appropriate enzyme solution and this solution was then allowed to evaporate to dryness. Toluene (1-2 μl) was added to each reaction solution prior to incubation at 37° C. so as to prevent bacterial growth during the incubation. Reactions (with the exception of neuraminidases) were terminated by heating to 100° C. for 5 minutes, desalted, and the products analysed by Bio-Gel P-4 column chromatography as described in part IV, below.

IV Gel Permeation Chromatography

Bio-Gel P-4 (<400 mesh) gel permeation chromatography was performed by using a 1.5×200 cm column. The column was maintained at 55° C. and water (200 μl/min) was used as the eluent. The eluent was monitored for radioactivity using a Berthold HPLC radioactivity monitor (model LB503) and for refractive index using a Perkin-Elmer model LC25 refractometer. Analog signals from the monitors were digitized using Nelson Analytical ADC interfaces. The digital values were collected and analysed using Hewlett Packard 9836C computers. The elution position of glucose oligomers (partial dextran hydrolysate) in glucose units (g.u.) was detected simultaneously by the refractive index detector. Radioactive sample elution positions (in glucose units) were calculated by cubic spline enterpolation between the internal standard glucose oligomer positions.

V Standard oligosaccharides

The elution positions of oligosaccharides of known sequence and used to determine elution positions are listed in Table 3.

VI Fractionation of Acidic Asparagine-Linked Oligosaccharides

The acidic oligosaccharides fraction of both samples was separated from neutral components by either paper electrophoresis with pyridine/acetate buffer, pH 5.4, and Whatman 3 MM paper (30 cm), 80 V/cm or QAE-A25 Sephadex column chromatography. In the latter procedure samples were applied in 2 mM ammonium acetate (pH 5.3) to a 6 mm × 10 cm column equilibrated in 2 mM ammonium acetate and eluted with a 2-350 mM linear gradient of ammonium acetate.

Structural Analysis of Oligosaccharide C-A

The oligosaccharide fraction eluting at 22.5 g.u. (C-A) was found to be susceptible only to Jack bean (J.B.) β-galactosidase[a] and α-fucosidase[g] digestion. After J.B. β-galactosidase[a] digestion the oligosaccharide eluted at 17.5 g.u. indicating a loss of five β1→ linked galactose residues. The oligosaccharide was then digested with *Streptococcus pneumoniae* (S.P.) β-hexosaminidase[b] with the loss of one β1→ linked GlcNAc residue. This digestion product was found to be sensitive to only J.B. β-hexosaminidase[c] and bovine epidydimis (B.E.) α-fucosidase[g]. Upon digestion with J.B. β-hexosaminidase[c] four additional residues of GlcNAc were removed. The digestion product which eluted at 8.2 g.u. was subsequently digested with J.B. α-mannosidase[d]. The digestion product eluted at 6.5 g.u., thereby indicating the loss of two residues of α-linked mannose. The oligosaccharide fragment eluting at 6.5 g.u. was susceptible to digestion only with snail β-mannosidase[e] and α-fucosidase. After digestion with snail β-mannosidase[d] the product eluted at 5.5 g.u. and was susceptible to only J.B. β-hexosaminidase[f] and α-fucosidase[g]. After J.B. β-hexosaminidase digestion[f] the oligosaccharide eluted at 3.5 g.u. and was susceptible only to α-fucosidase[g] digestion.

By comparing the initial elution positions and the exoglycosidases reactivity of oligosaccharides of known sequence (Table 3) the fragmentation which resulted from the sequential exoglycosidase digestion a→b→c→d→e→f→g is consistent with the structure C-A when the exoglycosidases anomer, bond and aglycon specificities (section II) and known biosynthetic pathway of N-linked oligosaccharides are taken into account. See Kobata in "Biology of Carbohydrates," Ginsburg and Robbins, Eds., John Wiley and Sons, pp. 87-162, 1984; Snider, Ibid., pp. 163-193.

| | | | | |
|---|---|---|---|---|
| (a) | J.B. | β-galactosidase | Δ5 | galactose residues |
| (b) | S.P. | β-hexosaminidase | Δ1 | GlcNAc residues |
| (c) | J.B. | β-hexosaminidase | Δ4 | GlcNAc residues |
| (d) | J.B. | α-mannosidase | Δ2 | mannose residues |
| (e) | snail | β-mannosidase | Δ1 | mannose residue |
| (f) | J.B. | β-hexosaminidase | Δ1 | GlcNAc residue |
| (g) | B.E. | α-fucosidase | Δ1 | fucose residue |

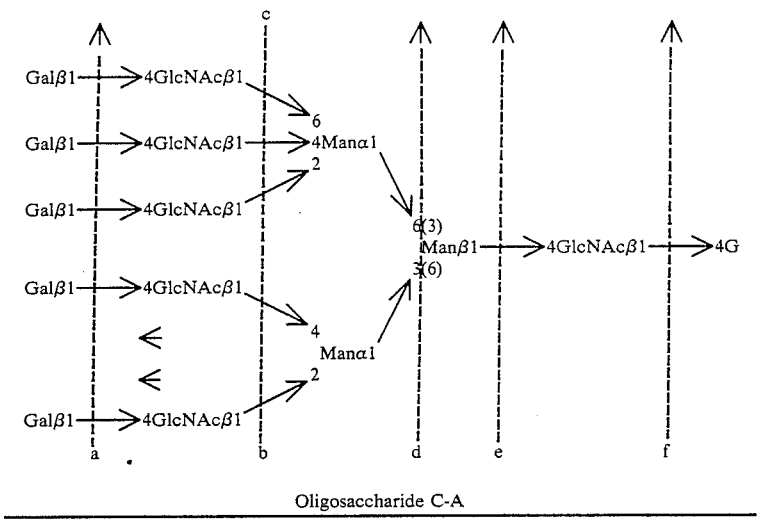

Oligosaccharide C-A

Structural Analysis of Oligosaccharide C-B

The fraction C-B eluting at 19.5 g.u. was found to be susceptible to digestion initially with only J.B. β-galactosidase[a] and α-fucosidase[g]. After treatment with J.B. β-galactosidase[a] the 19.5 g.u. fraction was converted to a fraction eluting at 15.5 g.u. The difference in elution volume indicates the release of four galβ→ groups from the original oligosaccharide. By incubation with S.P. β-hexosaminidase[b] the 15.5 g.u. fraction was converted to a radioactive peak 13.5 g.u., which by elution difference, indicated the loss of one GlcNAcβ→ group. This resultant structure was found to be susceptible only to J.B. β-hexosaminidase[c] and α-fucosidase[g] treatment. Incubation of the 13.5 g.u. fraction with J.B. β-hexosiminidase[c] resulted in the loss of three additional GlcNacβ→ residues. The resultant fraction 8.5 g.u. was found to be susceptible to only J.B. α-mannosidase[d] and α-fucosidase[g]. Upon incubation with J.B. α-mannosidase[d] two residues of Man α→ were released. The oligosaccharide fragment eluting at 6.5 g.u. was susceptible to digestion only with snail β-mannosidase[e] and β-fucosidase[g]. After digestion with snail β-mannosidase[e] the product eluted at 5.5 g.u. and was susceptible to only J.B. β-hexosminidase[g] and α-fucosidase[g] digestion.

By comparing the initial elution positions and the exoglycosidase reactivity of oligosaccharides of known sequence (Table 3) the fragmentation which resulted from the sequential exoglycosidase digestion a→b→d→e→f→g is consistent with the structure C-B when the exoglycosidase anomer, bond and aglycon specificities (section II) and known biosynthetic pathway for N-linked oligosaccharides are taken into account.

| | | | | |
|---|---|---|---|---|
| (a) | J.B. | β-galactosidase | Δ4 | galactose residues |
| (b) | S.P. | β-hexosaminidase | Δ1 | GlcNAc residue |
| (c) | J.B. | β-hexosaminidase | Δ3 | GlcNAc residues |
| (d) | J.B. | α-mannosidase | Δ2 | mannose residues |
| (e) | snail | β-mannosidase | Δ1 | mannose residue |
| (f) | J.B. | β-hexosaminidase | Δ1 | GlcNAc residue |
| (g) | B.E. | α-fucosidase | Δ1 | fucose residue |

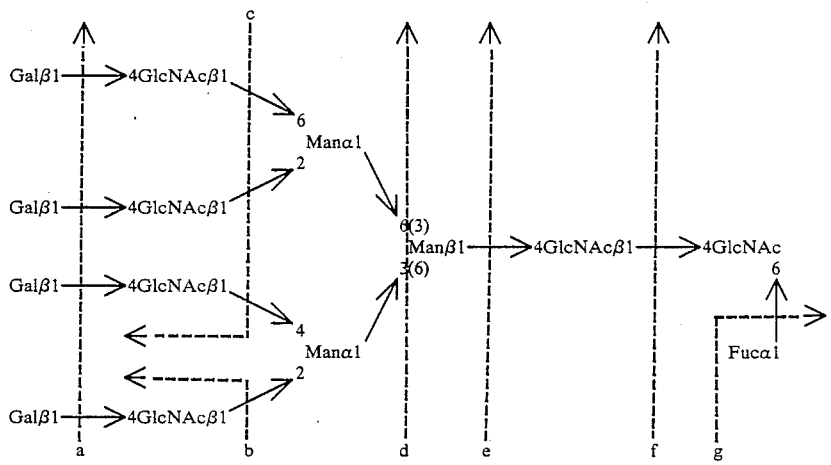

Structural Analysis of Oligosaccharide C-C-1

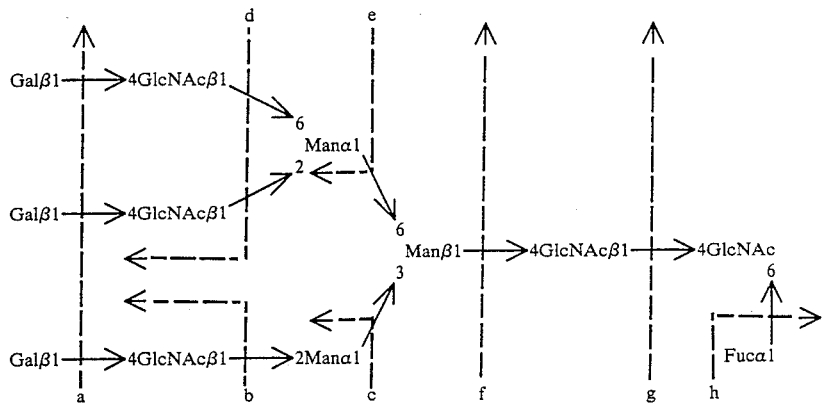

Oligosaccharide C-C-1

The oligosaccharides eluting in fraction C-C centered at 17.2 g.u. were initially susceptible to digestion only with J.B. β-galactosidase$^{(a)}$ and B.E. α-fucosidase$^{(h)}$. After digestion with β-galactosidase the oligosaccharide eluted at 13.5 g.u. indicating a loss of 3 terminal β-galactose residues. The oligosaccharide fraction was then subjected to digestion with S.P. β-hexosaminidase$^{(b)}$. Three fractions (11.5 g.u.), (10.2 g.u.) and (9.5 g.u.) were found upon subsequent Bio-Gel P-4 chromatography.

Fraction C-C-1 (11.5 g.u.) was formed by the loss of one residue of GlcNAcβ→. Fraction C-C-1 was subsequently found to be susceptible to both J.B. β-hexosaminidase$^{(d)}$ (loss of 2 GlcNAcβ residues) and to J.B. α-mannosidase $^{(c)}$ indicating the exposure of a mannose α→ residue after S.P. β-hexosaminidase digestion. After J.B. β-hexosaminidase digestion an additional α-linked mannose residue was susceptible to J.B. α-mannosidase digestion$^{(e)}$. Following the sequential digestion a→b→c→d→e the oligosaccharide C-C-1 eluted at 6.5 g.u. and was susceptible only to α-fucosidase$^{(h)}$ and snail β-mannosidase$^{(f)}$. Digestion with snail β-mannosidase$^{(f)}$ resulted in the loss of one mannonse β→ residue. The oligosaccharide which then eluted at 5.5 g.u. was then subjected to digestion with J.B. β-hexosaminidase$^{(g)}$ with the loss of one GlcNAcβ→ residue. This digestion product which eluted at 3.5 g.u. was found to be susceptible to only α-fucosidase$^{(h)}$.

By comparing the initial elution positions and the exoglycosidase reactivity of oligosaccharides of known sequence (Table 3) the fragmentation which resulted from the sequential exoglucosidase digestion of a→b→c→d→e→f→g→h is consistent with the structure C-C-1, when exoglycosidase anomer, bond and aglycon specificities (section II) and the known biosynthetic pathway for N-linked oligosaccharides are taken into account.

Structural Analysis of Oligosaccharide C-C-2

The oligosaccharides eluting in fraction C-C centered at 17.2 g.u. were initially susceptible to digestion only with J.B. β-galactosidase$^{(a)}$ and B.E. α-fucosidase$^{(g)}$. After digestion with β-galactosidase the oligosaccharide eluted at 13.5 g.u. indicating a loss of 3 terminal β-galactose residues. The oligosaccharide fraction was then subjected to digestion with S.P. β-hexosaminidase$^{(b)}$. Three fractions (11.5 g.u.), (10.2 g.u.) and (9.5 g.u.) were found upon subsequent Bio-Gel P-4 chromatography.

The 10.2 g.u. fraction was formed by the loss of two residues of GlcNAcβ→. Upon treatment with J.B. α-mannosidase the 10.2 g.u. fraction was found to split into a resistant (C-C-2) and a susceptible 9.2 g.u. (C-C-3) fraction. When C-C-2 was subjected to J.B. β-hexosaminidase$^{(d)}$ one additional β-linked GlcNAc was removed. Sequential digestion with J.B. α-mannosidase$^{(d)}$ resulted in the loss of two residues of mannose α→. Following the sequential digestion a→b→c→d the oligosaccharide was susceptible only to α-fucosidase$^{(g)}$ and snail β-mannosidase$^{(e)}$. Digestion with snail β-mannosidase$^{(e)}$ resulted in the loss of one mannose β→ residue. The oligosaccharide which then eluted at 5.5 g.u. was then subjected to digestion with J.B. β-hexosaminidase$^{(f)}$ with the loss of one GlcNAc β→ residue. This resultant digestion product which eluted at 3.5 g.u. was found to be susceptible to only α-fucosidase$^{(g)}$.

By comparing the initial elution positions and the exoglycosidase reactivity of oligosaccharides of known sequence (Table 3) the fragmentation which resulted from the sequential exoglycosidase digestion of a→b→c→d→e→f→g is consistent with structure C-C-2 when the exoglycosidase anomer, bond and aglycon specificities (section II) and the known biosynthetic pathway for N-linked oligosaccharides are taken into account.

oligosaccharide was found to be susceptible to only J.B. β-hexosaminidase[d] and B.E. α-fucosidase[h]. Digestion with J.B. β-hexosaminidase resulted in the loss of one residue of GlcNacβ→. Subsequent digestion with J.B. α-mannosidase[e] resulted in the loss of one residue of mannose α→. Following the sequential digestion a→b→c→d→e the oligosaccharide eluted at 6.5 g.u. and was susceptible only to α-fucosidase[h] and snail β-mannosidase[f]. Digestion with snail β-mannosidase[f] resulted in the loss of one mannose β→ residue. The oligosaccharide which then eluted at 5.5 g.u. was then digested with J.B. β-hexosaminidase[g] with the loss of one GlcNAc β→. The product of this reaction eluted at 3.5 g.u. and was found to be susceptible only to α-fucosidase[h].

| | | | |
|---|---|---|---|
| (a) | J.B. | β-galactosidase | Δ3 residues galactose |
| (b) | S.P. | β-hexosaminidase | Δ2 residues GlcNAc |
| (c) | J.B. | β-hexosaminidase | Δ1 residue GlcNAc |
| (d) | J.B. | β-hexosaminidase | Δ2 residues mannose |
| (e) | snail | β-mannosidase | Δ1 residue mannose |
| (f) | J.B. | β-hexosaminidase | Δ1 residue GlcNAc |
| (g) | B.E. | α-fucosidase | Δ1 residue fucose |

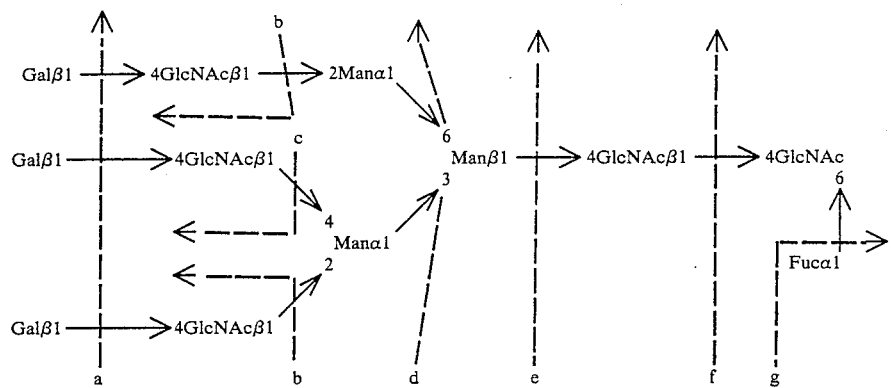

Oligosaccharide C—C—2

Structural Analysis of Olidosaccharide C-C-3

The oligosaccharides eluting in fraction C-C centered at 17.2 g.u. were initially susceptible to digestion only with J.B. β-galactosidase[a] and B.E. α-fucosidase[h]. After digestion with 62 -galactosidase the oligosaccharide eluted at 13.5 g.u. indicating a loss of 3 terminal galactose β→ residues. The oligosaccharide fraction was then subjected to digestion with S.P. β-hexosaminidase[b]. Three fractions (11.5 g.u.), (10.2 g.u.) and (9.5 g.u.) were found upon subsequent Bio-Gel P-4 chromatography.

The 10.2 g.u. fraction was formed by the loss of two residues of GlcNAc β→. Upon treatment with J.B. α-mannosidase[c] the 10.2 g.u. fraction was found to split into a resistant C-C-2 and susceptible 9.2 g.u. (C-C-3) fraction. The loss of one residue of α linked mannose indicated that the exposure of an α(1-3) linked mannose after S.P. β-hexosaminidase digestion. The resultant By comparing the initial elution positions and the exoglycosidase reactivity of oligosaccharides of known sequence (Table 3) the fragmentation which resulted from the sequential exoglycosidase digestion of a→b→c→d→e→f→g→h is consistent with the structure C-C-3 when the exoglycosidase anomer, bond and aglycon (section II) specificities and the known biosynthetic pathway for N-linked oligosaccharides are taken into account.

| | | | |
|---|---|---|---|
| (a) | J.B. | β-galactosidase | Δ3 galactose residues |
| (b) | S.P. | β-hexosaminidase | Δ2 GlcNAc residues |
| (c) | J.B. | β-mannosidase | Δ1 mannose residue |
| (d) | J.B. | β-hexosaminidase | Δ1 GlcNAc residue |
| (e) | J.B. | α-mannosidase | Δ1 mannose residue |
| (f) | snail | β-mannosidase | Δ1 mannose residue |
| (g) | J.B. | β-hexosaminidase | Δ1 GlcNAc residue |
| (h) | B.E. | α-fucosidase | Δ1 fucose residue |

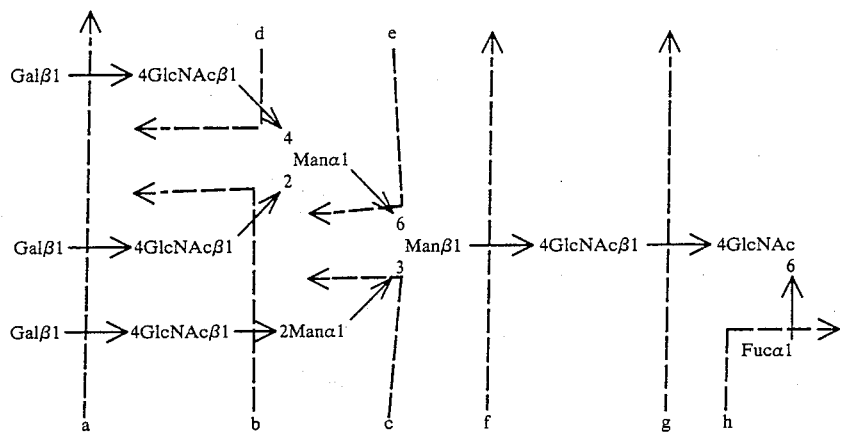

Oligosaccharide C—C—3

Structure Analysis of Oligosaccharide C-C-4

The oligosaccharides eluting in fraction C-C centered at the 17.2 g.u. were initially susceptible to digestion only with J.B. β-galactosidase[a] and B.E. α-fucosidase[h]. After digestion with β-galactosidase the oligosaccharide eluted at 13.5 g.u. indicating a loss of 3 terminal galactose β→ residues. The oligosaccharide fraction was then subjected to digestion with S.P. β-hexosaminidase[b]. Three fractions (11.5 g.u.), (10.2 g.u.) and (9.5 g.u.) were found upon subsequent Bio-Gel P-4 chromatography. Fraction 9.5 g.u. (C-C-4) was formed by the loss of two residues of GlcNAc β→. Fraction C-C-4 was subsequently found to be susceptible to both J.B. β-hexosaminidase [d] (loss of one GlcNAc β→ residue) and to J.B. α-mannosidase[c] indicating the exposure of one α(1.3) linked mannose after S.P. digestion. After J.B. β-hexosaminidase digestion[d] an additional mannose residue was susceptible to J.B. α-mannosidase[e] digestion indicating that the α1-6 mannose was substituted GlcNAc β1-4 (GlcNAcβ1-2) Manα1-6→R. Following the sequential digestion a→b→c→d→e the structure eluted at 5.5 g.u. units. The digestion product was susceptible only to β-mannosidase[f]. Digestion with snail β-mannosidase[f] resulted in the loss of one mannose β→ residue. The digestion product which eluted at 4.5 g.u. was found to be susceptible only to J.B. β-hexosaminidase[g] with the loss of one β-GlcNAc residue.

By comparing the initial elution positions and the exoglycosidase reactivity of oligosaccharides of known sequence (Table 3) the fragmentation which resulted from the sequential exoglycosidase digestion of a→b→c→d→e→f→g is consistent with structure C-C-4 when the exoglycosidase anomer, bond and aglycon specificities (section II) and the known biosynthetic pathway of N-linked oligosaccharides are taken into account.

| | | |
|---|---|---|
| (a) J.B. | β-galactosidase | Δ3 galactose residues |
| (b) S.P. | β-hexosaminidase | Δ2 GlcNAc residues |
| (c) J.B. | α-mannosidase | Δ1 mannose residue |
| (d) J.B. | β-hexosaminidase | Δ1 GlcNAc residue |
| (e) J.B. | α-mannosidase | Δ1 mannose residue |
| (f) snail | β-mannosidase | Δ1 mannose residue |
| (g) J.B. | β-hexosaminidase | Δ1 GlcNAc residue |

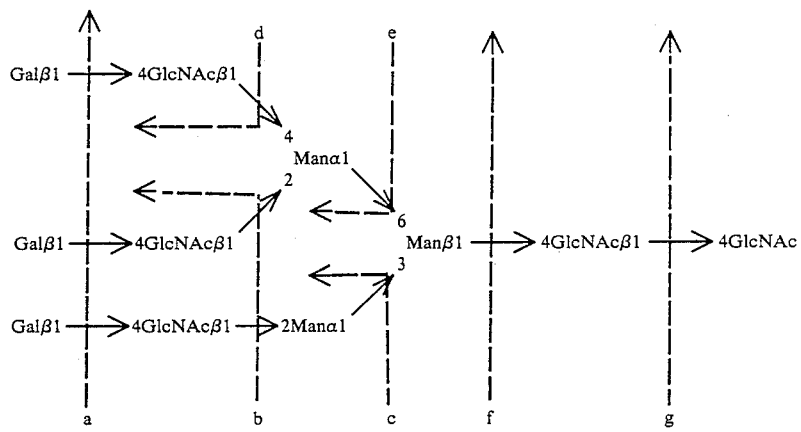

Oligosaccharide C—C—4

Structural Analysis of Oligosaccharide C-D-1

The oligosaccharide fraction eluting at 15.2 g.u. was found to be susceptible to J.B. β-galactosidase[a]. Upon digestion with J.B. β-galactosidase[a] the 15.2 fraction was converted to a fraction eluting at 13.5 g.u. The difference in elution volume indicates the release of 2 Galβ→ groups from the original oligosaccharide. Upon incubation of the 13.5 g.u. fraction with S.P. β-hexosaminidase[b] one GlcNAcβ→ group was released. This 11.5 g.u. digestion product was resistant to J.B. α-mannosidase but upon incubation with J.B. β-hexosaminidase[c] two additional GlcNAc⊖→ residues were released. The resultant fraction at 8.5 g.u. was found to be susceptible to only J.B. α-mannosidase[d] and α-fucosidase[g]. Upon incubation with J.B. α-mannosidase[d] two residues of Manα→ were released. The oligosaccharide fragment eluting at 6.5 g.u. was susceptible to digestion only with snail β-mannosidase[e] and α-fucosidase[g]. After digestion with snail β-mannosidase[e] the product eluted at 5.5 g.u. and was susceptible to only J.B. hexosaminidase[f] and α-fucosidase[g] digestion.

By comparing the initial elution positions and the exoglycosidase reactivity of oligosaccharides of known specificity (Table 3) the fragmentation which resulted from the sequential exoglycosidase digestion a→b→c→d→e→f→g is consistent with the structure C-D-1 when the exoglycosidase anomer, bond and aglycon specificities (section II) and known biosynthetic pathway of N-linked oligosaccharides are taken into account.

Structural Analysis of Oligosaccharide C-D-2

The oligosaccharide fraction eluting at 14.5 g.u. was found to be initially susceptible to J.B. β-galactosidase[a] and B.E. α-fucosidase[f]. Upon incubation with J.B. β-galactosidase[a] the 14.5 g.u. fraction was converted to a fraction eluting at 12.3 g.u. The difference in elution volume indicates the release of 2 gal→ groups from the original oligosaccharide. Upon incubation with either J.B. β-hexosaminidase or S.P. β-hexosaminidase[b] the 12.3 g.u. fraction was converted to a fraction eluting at 8.2 g.u. The difference in elution volume indicates the release of 2 GlcNAc β→ groups. The digestion product which eluted at 8.2 g.u. was subsequently incubated with J.B. α-mannosidase[c]. The digestion product eluted at 6.5 g.u. indicating the loss of two residues of α-linked mannose. The oligosaccharide fragment eluting at 6.5 g.u. was susceptible to digestion only with snail β-mannosidase[d] and α-fucosidase[f]. After digestion with snail β-mannosidase[d] the product eluted at 5.5 g.u. and was susceptible to only J.B. β-hexosaminidase[e] and α-fucosidase[f]. After J.B. β-hexosaminidase digestion[e] the oligosaccharide eluted at 3.5 g.u. and was susceptible only to α-fucosidase[f] digestion.

By comparing the initial elution positions and the exoglycosidase reactivity of oligosaccharides of known sequence (Table 3) the fragmentation which resulted from the sequential exoglycosidase digestion a→b→c→d→e→f is consistent with the structure C-D-2 when exoglycosidase anomer, bond and aglycon specificities

| (a) J.B. | β-galactosidase | Δ2 residues | galactose |
| (b) S.P. | β-hexosaminidase | Δ1 residue | GlcNAc |
| (c) J.B. | β-hexosaminidase | Δ2 residues | GlcNAc |
| (d) J.B. | α-mannosidase | Δ2 residues | mannose |
| (e) snail | β-mannosidase | Δ1 residue | mannose |
| (f) J.B. | β-hexosaminidase | Δ1 residue | GlcNAc |
| (g) B.E. | α-fucosidase | Δ1 residue | fucose |

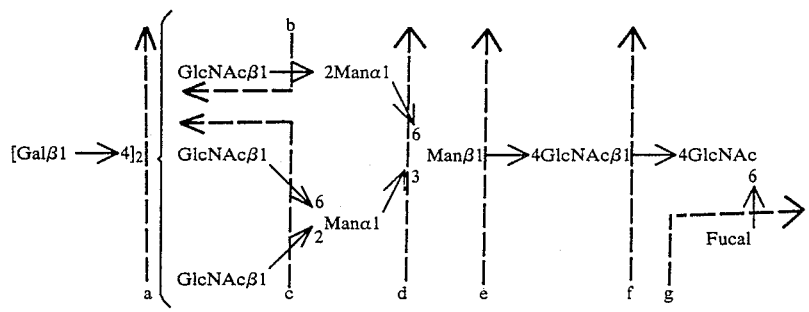

Oligosaccharide C-D-1

(section II) and the known biosynthetic pathway of N-linked oligosaccharides are taken into account.

| (a) J.B. | β-galactosidase | Δ2 galactose residues |
| (b) S.P. | β-hexosaminidase | Δ2 GlcNAc residues |
| (c) J.B. | α-mannosidase | Δ2 mannose residues |
| (d) snail | β-mannosidase | Δ1 mannose residue |
| (e) J.B. | β-hexosaminidase | Δ1 GlcNAc residue |
| (f) B.E. | α-fucosidase | Δ1 fucose residue |

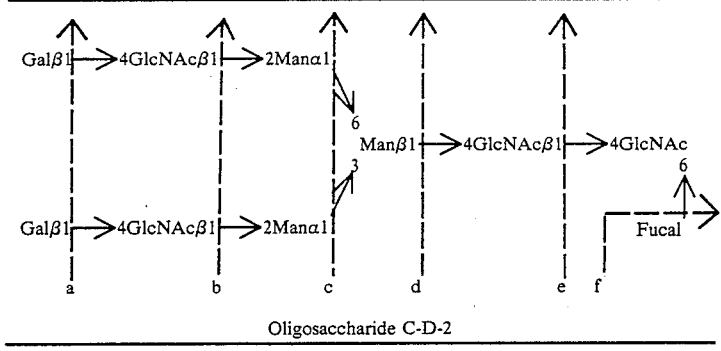

Oligosaccharide C-D-2

Structural Analysis of Oligosaccharide C-E

| | | | |
|---|---|---|---|
| (a) J.B. | β-galactosidase | Δ2 galactose residues |
| (b) S.P. | β-hexosaminidase | Δ2 GlcNAc residues |
| (c) J.B. | α-mannosidase | Δ2 mannose residues |
| (d) snail β-mannosidase | Δ1 mannose residue |
| (e) J.B. | β-hexosaminidase | Δ1 GlcNAc residue |

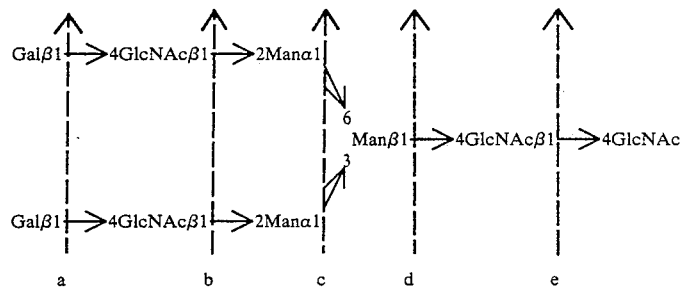

Oligosaccharide C-E

The oligosaccharide fraction eluting at 13.5 g.u. was found to be initially susceptible to only β-galactosidase[a]. Upon incubation with J.B. β-galactosidase[a] the 13.5 g.u. fraction was converted to a fraction eluting at 11.5 g.u. The difference in elution volume indicates the release of 2 gal β→ groups from the original oligosaccharide. Upon incubation with either J.B. β-hexosaminidase or S.P. β-hexosaminidase[b] the 11.5 g.u. fraction was converted to a fraction eluting at 8.2 g.u. The difference in elution volume indicates the release of 2 GlcNAcβ→ groups. The digestion product which eluted at 7.2 g.u. was subsequently incubated with J.B. α-mannosidase[c]. The digestion product eluted at 5.5 g.u. indicating the loss of two residues of α-linked mannose. The oligosaccharide fragment eluting at 5.5 g.u. was susceptible to digestion with only snail β-mannosidase[d]. After digestion with snail β-mannosidase[d] the product eluted at 4.5 g.u. and was susceptible to digestion only with J.B. β-hexosaminidase[e]. After incubation with J.B. β-hexosaminidase[e] the radioactivity was found at 2.5 g.u. indicating the loss of one GlcNAcβ→ residue.

By comparing the initial elution positions and the exoglycosidase reactivity of oligosaccharides of known sequence (Table 3) the fragmentation which resulted from the sequential exoglycosidase digestion a→b→c→d→e is consistent with the structure C-E when exoglycosidase anomer, bond and aglycon specificities (section II) and the known biosynthetic pathway of N-linked oligosaccharides are taken into account.

Structural Analysis of Oligosaccharide C-F

The 12.2 fraction when incubated with J.B. β-galactosidase[a] was converted to a fraction 11.2 g.u. indicating the loss of one Galβ1→ residue. Upon subsequent incubation with J.B. α-mannosidase[b] the 11.2 g.u. fraction was converted to a fraction eluting a 9.2 g.u. From the difference in elution volume two Manα→ residues were removed. The 9.2 g.u. fraction was found to convert upon incubation with S.P. β-hexosamindase[c] to a fraction eluting at 7.2 g.u. indicating the loss of one GlcNAcβ1→ residue. The 7.2 g.u. fraction when subsequently incubated with J.B. α-mannosidase[d] converted to a fraction eluting at 5.5 g.u. indicating the loss of two Man1α→ residues. The 5.5 g.u. fraction was resistant to all exoglycosidase except snail β-mannosidase[e]. The 5.5 g.u. fraction was converted to a fraction eluting at 4.5 g.u. indicating the loss of one Manβ→ residue. The 4.5 g.u. fraction was subsequently converted to 2.5 g.u. upon incubation with J.B. β-hexosaminidase[f].

By comparing the initial elution positions and the exoglycosidase reactivity of oligosaccharides of known sequence (Table 3) the fragmentation found on the sequential exoglycosidase digestion a→b→c→d→e→f is consistent with structure C-F when exoglycosidase anomer, bond and aglycon specificities (section II) and the known biosynthetic pathway for N-linked oligosaccharides are taken into account.

|   |   |   |   |
|---|---|---|---|
| (a) | J.B. | β-galactosidase | Δ1 galactose residue |
| (b) | J.B. | α-mannosidase | Δ2 mannose residues |
| (c) | S.P. | β-hexosaminidase | Δ1 GlcNAc residue |
| (d) | J.B. | α-mannosidase | Δ2 mannose residues |
| (e) | snail | β-mannosidase | Δ1 mannose residue |
| (f) | J.B. | β-hexosaminidase | Δ1 GlcNAc residue |

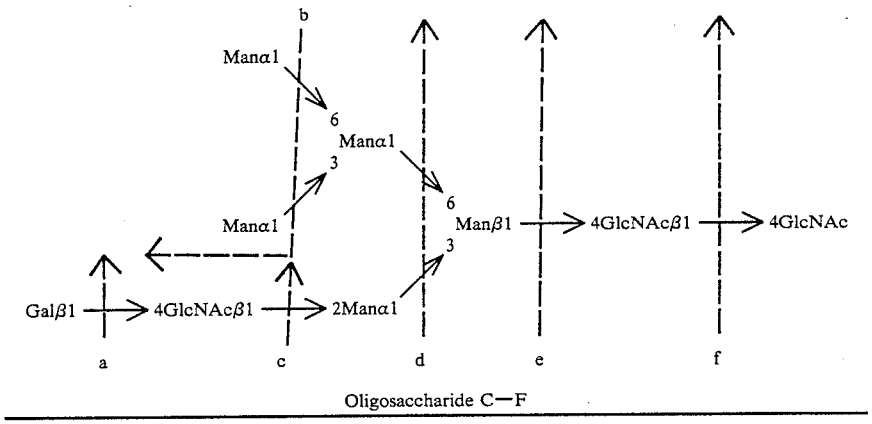

Oligosaccharide C—F

Structural Analysis of Oligosaccharide C-G-1

The 11.2 g.u. fraction when incubated with *Aspergillus phoenicius* remained intact. Upon subsequent incubation with J.B. α-mannosidase[a] the 11.2 g.u. fraction was converted to two fractions, one eluting at 9.5 g.u. (C-G-1) indicating a loss of two Manα units from the parent structure, and one eluting at 10.5 g.u. (C-G-2) indicating a loss of one Manα unit from the parent structure. Upon subsequent incubation with J.B. β-galactosidase[b] the 9.5 g.u. fraction was converted to a fraction eluting at 8.5 g.u. indicating the loss of one Gal β1→4 residue. The 8.5 g.u. fraction when subsequently incubated with S.P. β-hexosaminidase[c] was converted to a fraction eluting at 6.5 g.u. indicating the loss of one GlcNAc β1→ residue. The 6.5 g.u. fraction was then incubated with J.B. α-mannosidase[d] and converted to a fraction eluting at 5.5 g.u. indicating a loss of one manα residue. This 5.5 g.u. fraction was resistant to all exoglycosidases except snail β-mannosidase[e]. When incubated with snail β-mannosidase[e] the 5.5 g.u. fraction was converted to a fraction eluting at 4.5 g.u. indicating the loss of one manβ1→ residue. The 4.5 g.u. fraction was subsequently converted to a 2.5 g.u. fraction upon incubation with J.B. β-hexosaminidase[f].

By comparing the initial elution positions and the exoglycosidase reactivity of oligosaccharides of known sequences (Table 3) the fragmentation found on the sequential exoglycosidase digestion a→b→c→d→e→f is consistant with structure C-G-1 when exoglycosidase anomer, bond and aglycon specificities (section II) and the known biosynthetic pathway for N-linked oligosaccharides are taken into account.

|   |   |   |   |
|---|---|---|---|
| (a) | J.B. | α-mannosidase | Δ2 mannose residues |
| (b) | J.B. | β-galactosidase | Δ1 galactose residue |
| (c) | S.P. | β-hexosaminidase | Δ1 GlcNAc residue |
| (d) | J.B. | α-mannosidase | Δ1 mannose residue |
| (e) | snail | β-mannosidase | Δ1 mannosidase residue |
| (f) | J.B. | β-hexosaminidase | Δ1 GlcNAc residue |

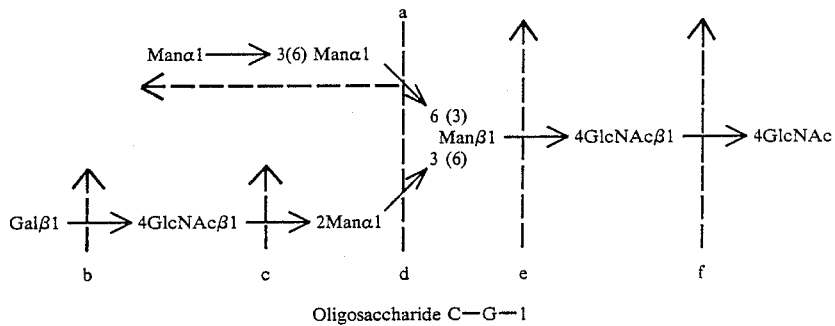

Oligosaccharide C—G—1

Structural Analysis of Oligosaccharide C-G-2

The 10.5 g.u. fraction obtained from the 11.2 g.u. fraction by J.B. α-mannosidase[a] digestion was incubated with J.B. β-galactosidase[b] and converted to a 9.5 g.u. fraction, indicating the loss of one galβ1→4 residue. When this 9.5 g.u. fraction was incubated with S.P. β-hexosaminidase[c] it was converted to a fraction eluting at 7.5 g.u. indicating the loss of one GlcNAcβ1→. The 7.5 g.u. fraction when subsequently incubated with J.B. α-mannosidase$^{(d)}$ converted to a fraction eluting at 6.5 g.u. indicating the loss of one Manα residue. The 6.5 g.u. fraction was resistant to all exoglycosidases except snail β-mannosidase$^{(e)}$ and B.E. α-fucosidase$^{(g)}$. When incubated with snail β-mannosidase the 6.5 g.u. fraction was converted to a fraction eluting at 5.5 g.u. indicating the loss of one mannose β1→ resude. The 5.5 g.u. fraction was subsequently converted to a 3.5 g.u. fraction after incubation with J.B. β-hexosaminidase$^{(f)}$ indicating the loss of one GlcNAcβ1→ residue. Upon incubation with B.E. α-fucosidase$^{(g)}$ the 3.5 g.u. fraction was converted to a 2.5 g.u. fraction indicating the loss of one α-fucose residue.

By comparing the initial elution positions and the exoglycosidase reactivity of oligosaccharides of known sequence (Table 3) the fragmentation found on the sequential exoglycosidase digestion a→b→c→d→e→f→g is consistent with structure C-G-2 when exoglycosidase anomer, bond and aglycon specificities (section II) and the known biosynthetic pathway for N-linked oligosaccharides are taken into account.

Structural Analysis of Oligosaccharide C-G-3

A 10.5 g.u. fraction when incubated with Aspergillus phoenicis (A.P.) α-mannosidase$^{(a)}$ was converted to a fraction eluting at 8.9 g.u. units indicating the loss of two Manα residues. Upon subsequent incubation with J.B. α-mannosidase$^{(b)}$ the 8.9 g.u. fraction was converted to a fraction eluting at 5.5 g.u. indicating the loss of four Manα residues. The 5.5 g.u. fraction was resistant to all exoglycosidase except small snail β-mannosidase$^{(c)}$. When incubated with snail β-mannosidase$^{(c)}$ the 5.5 g.u. fraction was converted to a fraction eluting at 4.5 g.u. indicating the loss of one manβ→ residue. The 4.5 g.u. fraction was subsequently converted to a 2.5 g.u. fraction upon incubation with J.B. β-hexosaminidase$^{(d)}$.

By comparing the initial elution positions and the exoglycosidase reactivity of oligosaccharides of known sequence (Table 3) the fragmentation found on the sequential exoglycosidase digestion a→b→c→d is consistent with structure C-G-3 when exoglycosidase anomer, bond and aglycon specificities (section II) and the known biosynthetic pathway of N-linked oligosaccha-

| | | | |
|---|---|---|---|
| (a) | J.B. | α-mannosidase | Δ1 mannose residue |
| (b) | J.B. | β-galactosidase | Δ1 galactose residue |
| (c) | S.P. | β-hexosaminidase | Δ1 GlcNAc residue |
| (d) | J.B. | α-mannosidase | Δ1 mannose residue |
| (e) | snail | β-mannosidase | Δ1 mannose residue |
| (f) | J.B. | β-hexosaminidase | Δ1 GlcNAc residue |
| (g) | B.E. | α-fucosidase | Δ1 fucose residue |

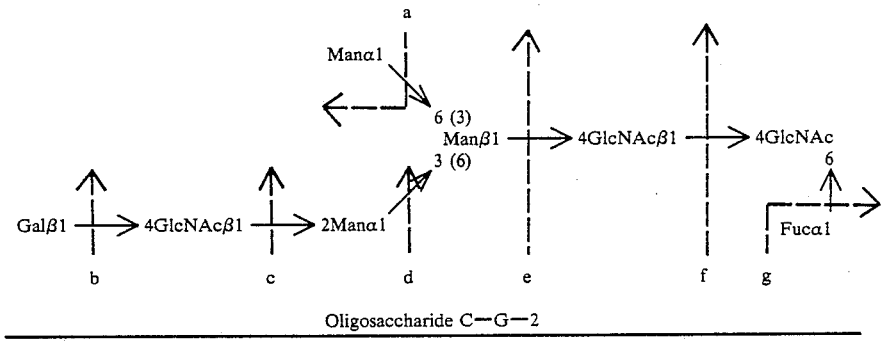

Oligosaccharide C—G—2 rides are taken into account.

| | | | |
|---|---|---|---|
| (a) | A.P. | α-mannosidase | Δ2 mannose residues |
| (b) | J.B. | α-mannosidase | Δ4 mannose residues |
| (c) | snail | β-mannosidase | Δ1 mannose residue |
| (d) | J.B. | β-hexosaminidase | Δ1 GlcNAc residue |

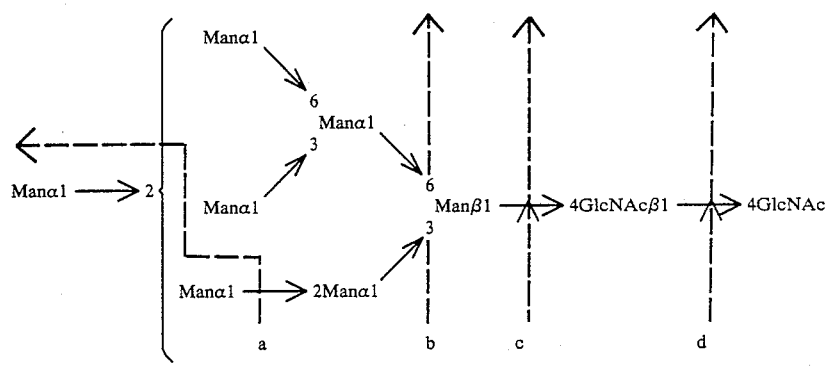

Oligosaccharide C—G—3

Structural Analysis of Oligosaccharide C-H known biosynthetic pathway for N-linked oligosaccharides are taken into account.

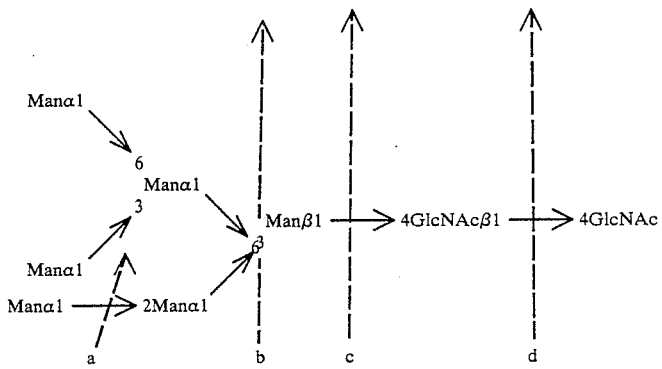

| | | | |
|---|---|---|---|
| (a) | A.P. | α-mannosidase | Δ1 mannose residue |
| (b) | J.B. | α-Mannosidase | Δ4 mannose residues |
| (c) | snail | β-mannosidase | Δ1 mannose residue |
| (d) | J.B. | β-hexosaminidase | Δ1 GlcNAc residue |

Oligosaccharide C—H

A 9.8 g.u. fraction when incubated with *Aspergillus phoenicis* α-mannosidase[a] was converted to a fraction which eluted at 8.9 g.u. indicating the loss of one Manα residue. Upon subsequent incubation with J.B. α-mannosidase[b] the 8.9 g.u. fraction was converted to a fraction eluting at 5.5 g.u. indicating the loss of 4 Manα residues. The 5.5 g.u. fraction was resistant to all exoglycosidases except snail β-mannosidase[c]. Then incubated with snail β-mannosidase[c] the 5.5 g.u. fraction was converted to a fraction eluting at 4.5 g.u. indicating the loss of one Manβ residue. The 4.5 g.u. fraction was subsequently converted to a 2.5 g.u. fraction upon incubation with J.B. β-hexosaminidase[d].

By comparing the initial elution positions and the exoglycosidase reactivity of oligosaccharides of known sequence (Table 3) the fragmentation found on the sequential exoglycosidase digestion a→b→c→d is consistent with structure C-H when exoglyosidase anomer, bond and aglycon specificities (section II) and the

Structural Analysis of Oligosaccharide C-I

The fraction eluting at 8.9 g.u. was resistant to digestion with *Aspergillus phoenicis* α-mannosidase but upon incubation with J.B. α-mannosidase[a] was converted to a fraction eluting at 5.5 g.u. The 5.5 g.u. fraction was resistant to all exoglycosidases except snail β-mannosidase[b]. When incubated with snail β-mannosidase[b] the 5.5 g.u. fraction was converted to a fraction eluting at 4.5 g.u. indicating the loss of one Manβ residue. The 4.5 g.u. fraction was subsequently converted to a 2.5 g.u. fraction upon incubation with J.B. β-hexosaminidase[c].

By comparing the initial elution positions and the exoglycosidase reactivity of the oligosaccharides of known sequence (Table 3) the fragmentation found on the sequential exoglycosidase digestion a→b→c is consistant with structure C-I when exoglycosidase anomer, bond and aglycon specificities (section II) and the known biosynthesis of N-linked oligosaccharides is taken into account.

| | | | |
|---|---|---|---|
| (a) | J.B. | α-mannosidase | Δ4 mannose residues |
| (b) | snail | β-mannosidase | Δ1 mannose residue |
| (c) | J.B. | β-hexosaminidase | Δ1 GlcNAc residue |

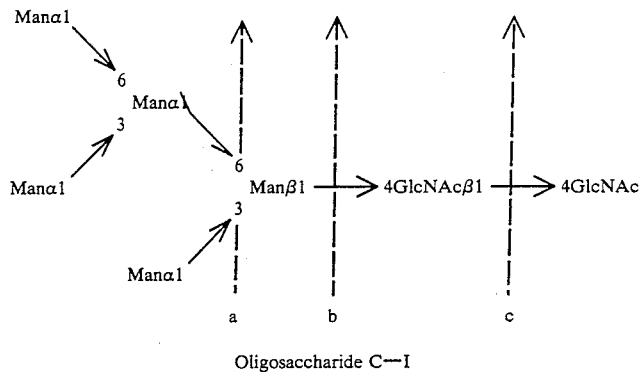

Oligosaccharide C—I

Structural Analysis of Oligosaccharide C-J

The fraction eluting at 7.9 g.u. was resistant to digestion with *Aspergillus phoenicis* α-mannosidase but upon digestion with J.B. α-mannosidase[a] was converted to a fraction eluting a 5.5 g.u. The 5.5 g.u. fraction was resistant to all exoglycosidases except small β-mannosidase[b]. When incubated with snail β-mannosidase the 5.5 g.u. fraction was converted to a fraction eluting at 4.5 g.u. indicating the loss of one Manβ residue. The 4.5 g.u. fraction was subsequently converted to a 2.5 g.u. fraction upon incubation with J.B. β-hexosaminidase[c].

By comparing the initial elution positions and the exoglycosidase reactivity of oligosaccharides of known sequence (Table 3) the fragmentation found on the sequential exoglycosidase digestion a→b→c is consistent with structure C-J when exoglycosidase anomer, bond and aglycon specificities (section II) and the known biosynthetic pathway for N-linked oligosaccharides are taken into account.

| (a) | J.B. | α-mannosidase | Δ3 mannose residues |
| (b) | snail | β-mannosidase | Δ1 mannose residue |
| (c) | J.B. | β-hexosaminidase | Δ1 GlcNAc residue |

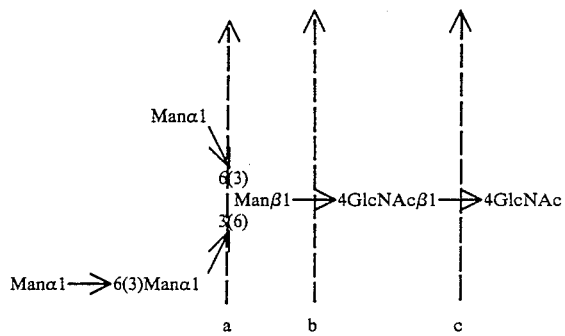

Oligosaccharide C-J

TABLE 1

| sample | N % | A-1% | A-2% | A-3% | A-4% |
|---|---|---|---|---|---|
| t-PA (colon) | 52.3 | 23.7 | 14.6 | 6.2 | 3.2 |
| t-PA (melanoma) | 49.5 | 8.6 | 21.1 | 12.1 | 8.7 |

TABLE 2

Colon t-PA*

| Fraction P-4 | Glucose Oligomer Position (g.u.) | Oligosaccharide | Percentage** |
|---|---|---|---|
| C-A | 24.2→21.5 | C-A | 1.5 |
| C-B | 21.5→18.4 | C-B | 11.8 |
| C-C | 18.4→15.8 | C-C-1 | 11.6 |
|  |  | C-C-2 | 3.0 |
|  |  | C-C-3 | 1.7 |
|  |  | C-C-4 | 1.3 |
| C-D | 15.8→13.8 | C-D-1 | 6.0 |
|  |  | C-D-2 | 21.0 |
| C-E | 13.8→12.7 | C-E | 7.3 |
| C-F | 12.7→11.7 | C-F | 3.9 |
| C-G | 11.7→10.4 | C-G-1 | 2.3 |
|  |  | C-G-2 | 1.9 |
|  |  | C-G-3 | 2.8 |
| C-H | 10.4→9.4 | C-H | 12.4 |
| C-I | 9.4→8.4 | C-I | 10.9 |
| C-J | 8.4→7.3 | C-J | 1.6 |

*See FIG. 5, Part A
**The percentages determined for each oligosaccharide are estimated to be subject to variation of less than about ±5% of the values shown.

TABLE 3

| | Standard Oligosaccharides* | Glucose Oligomer Position | Source |
|---|---|---|---|
| i | Galβ1→4GlcNAcβ1→2Manα1→6(Galβ1→4GlcNAβ1→4 (Galβ1→4GlcNAcβ1→2)Manα1→3)Manβ1→4GlcNAcβ1→4 GlcNAc | 16.2 g.u. | Bovine Fetuin |
| ii | GlcNAcβ1→2Manα1→6(GlcNAcβ1→4(GlcNAcβ1→2) Manα1→3)Manβ1→4GlcNAcβ1→4GlcNAc | 12.5 g.u. | β-Galactosidase treatment of i |
| iii | Manα1→6(Manα1→3)Manα1→6(Manα1→3)Manβ1→4 GlcNAcβ1→4GlcNAc | 8.9 g.u. | Bovine Ribonuclease B |
| iv | Galβ1→4GlcNAcβ1→2Manα1→6(Galβ1→4GlcNAcβ1→2 Manα1→3)Manβ1→4GcNAcβ1→4GlcNAc | 13.5 g.u. | Human serum transferrin |

TABLE 3-continued

| | Standard Oligosaccharides* | Glucose Oligomer Position | Source |
|---|---|---|---|
| v | Galβ1→4GlcNAcβ1→2Manα1→6(Galβ1→4GlcNAcβ1→2 Manα1→3)Manβ1→4GlcNAcβ1→4(Fucα1→6)GlcNac | 14.5 g.u. | Human serum IgG |
| vi | GlcNAcβ1→2Manα1→6(GlcNAcβ1→2Manα1→3)Manβ1→4 GlcNAcβ1→4GlcNAc | 11.2 g.u. | β-Galactosidase treatment of iv |
| vii | GlcNAcβ1→2Manα1→6(GlcNAcβ1→2Manα1→3)Manβ1→4 GlcNAcβ1→4(Fucα1→6)GlcNAc | 12.2 g.u. | Human serum IgG |
| viii | Manα1→6(GlcNAcβ1→2Manα1→3)Manβ1→4GlcNAcβ1→4 (Fucα1→6)GlcNAc | 10.5 g.u. | Exoglycosidase digestion of monosialyated v from IgG |
| ix | GlcNAcβ1→2Manα1→6(Manα1→3)Manβ1→4GlcNAcβ1→4 (Fucα1→6)GlcNAc | 10.5 g.u. | Exoglycosidase digestion of monosialyated v from IgG |
| x | Manα1→6(Manα1→3)Manβ1→4GlcNAcβ1→4(Fucα1→6)GlcNAc | 7.2 g.u. | β-Galactosidase and J.B. β-hexosaminidase digestion of vii |
| xi | Manβ1=4GlcNAcβ1→4(Fucα1→6)GlcNAc | 6.5 g.u. | J.B. α-mannosidase digestion of x |
| xii | GlcNAcβ1→4(Fucα1→6)GlcNAc | 5.5 g.u. | Snail β-mannosidase digestion of xi |
| xiii | Fucα1→6GlcNAc | 3.5 g.u. | J.B. β-hexosaminidase digestion of xii |
| xiv | GlcNAc | 2.5 g.u. | Reduction of N—acetyl-glucosamine with NaB$^3$H$_4$ |
| xv | GlcNAcβ1→4GlcNAc | 4.5 g.u. | α-Fucosidase treatment of xii |

*All structures have been reduced with NaB$^3$H$_4$ t-PA samples B and C as prepared above were similarly subjected to the treatment of sample A, above, up to and including the step of obtaining the Bio-Gel P-4 chromatograms following neuraminidase digestion. The Bio-Gel column chromatography profiles of the oligosaccharides from colon t-PA samples B and C were substantially similar to the profile of colon t-PA sample A in FIG. 5A.

In a manner similar to that for C-tPA, the oligosaccharides from B-tPA were analyzed further in order to determine the monosaccharide sequences present. In total, thirteen oligosaccharides (Table 4) were isolated from the B-tPA fractions, with high-mannose, hybrid and complex type represented. For convenience, the oligosaccharides isolated from B-tPA are designated by shorthand notation B-A to B-J.

Structural Analysis of Oligosaccharide B-A

The oligosaccharide eluting at 18.6 g.u. was found to be resistant to J.B. β-galactosidase and S.P. β-hexosaminidase. Upon subsequent digestion with J.B. β-hexosaminidase[a] the fraction was converted to a fraction eluting at 8.2 g.u. indicating the loss of 5-6 GlcNAcβ→ residues. The digestion product, which eluted at 8.2 g.u., was subsequently digested with J.B. α-mannosidase[b]. The digestion product eluted at 6.5 g.u., indicating the loss of two residues of α-linked mannose. The oligosaccharide fragment eluting at 6.5 g.u. was susceptible to digestion only with snail β-mannosidase[c] and α-fucosidase[e]. After digestion with snail β-mannosidase[c] the product eluted at 5.5 g.u. and was susceptible only to J.B. β-hexosaminidase[d] and α-fucosidase[e]. After J.B. β-hexosaminidase digestion[d] the oligosaccharide eluted at 3.5 g.u. and was susceptible only to α-fucosidase[e] digestion.

By comparing the initial elution positions and the exoglycosidase reactivity of oligosaccharides of known sequence (Table 3) the fragmentation which resulted from the sequential exoglycosidase digestion a→b→c→d→e is consistent with the structures B-A, when the exoglycosidase anomer, bond and aglycon specificities (section II, above) and known biosynthetic pathway of N-linked oligosaccharides are taken into account.

| (a) | J.B. | β-hexosaminidase | Δ5–6 GlcNAc residues |
| (b) | J.B. | α-mannosidase | Δ2 mannose residues |
| (c) | snail | β-mannosidase | Δ1 mannose residue |
| (d) | J.B. | β-hexosaminidase | Δ1 GlcNAc residue |
| (e) | B.E. | α-fucosidase | Δ1 fucose residue |

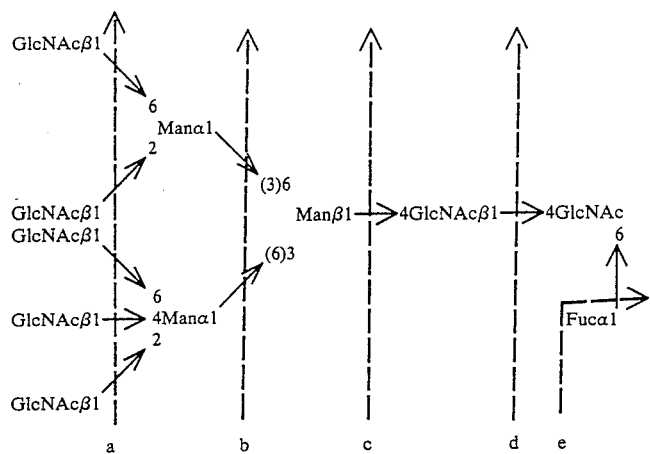

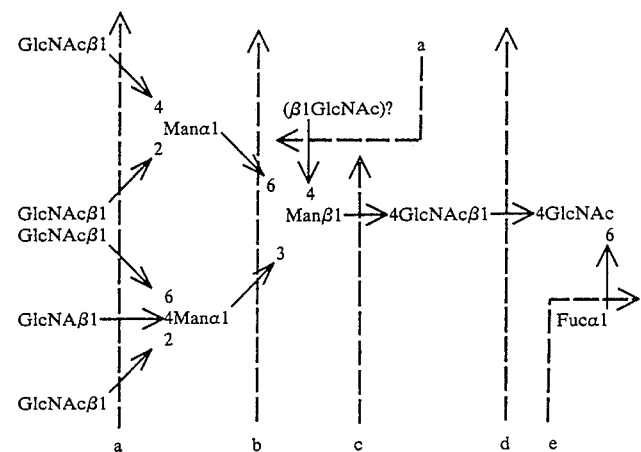

Oligosaccharide B-A

Structural Analysis of Oligosaccharide B-B

The oligosaccharide fraction eluting at 15.98 g.u. (B-B) was found to be resistant to S.P. β-hexosaminidase and J.B. β-galactosidase and susceptible only to J.B. β-hexosaminidase[a] and α-fucosidase[e]. After J.B. β-hexosaminidase[a] digestion the oligosaccharide eluted at 8.2 g.u. indicating the loss of five β→ linked GlcNAc residues. The digestion product which eluted at 8.2 g.u. was subsequently digested with J.B. α-mannosidase[b]. The digestion product eluted at 6.5 g.u., indicating the loss of two residues of α-linked mannose. The oligosaccharide fragment eluting at 6.5 g.u. was susceptible to digestion only with snail β-mannosidase[c] and α-fucosidase[e]. After digestion with snail α-mannosidase[c] the product eluted at 5.5 g.u. and was susceptible only to J.B. β-hexosaminidase[d] and α-fucosidase[e]. After J.B. β-hexosaminidase digestion[d] the oligosaccharide eluted at 3.5 g.u. and was susceptible only to α-fucosidase[e] digestion.

By comparing the initial elution positions and the exoglycosidase reactivity of oligosaccharides of known sequence (Table 3) the fragmentation which resulted from the sequential exoglycosidase digestion a→b→c→d→e is consistent with the structure B-B when the exoglycosidase anomer, bond and aglycon specificities (section II) and known biosynthetic pathway of N-linked oligosaccharides are taken into account.

| | | | |
|---|---|---|---|
| (a) | J.B. | β-hexosaminidase | Δ5 GlcNAc residues |
| (b) | J.B. | α-mannosidase | Δ2 mannose residues |
| (c) | snail | β-mannosidase | Δ1 mannose residue |
| (d) | J.B. | β-hexosaminidase | Δ1 GlcNAc residue |
| (e) | B.E. | α-fucosidase | Δ1 fucose residue |

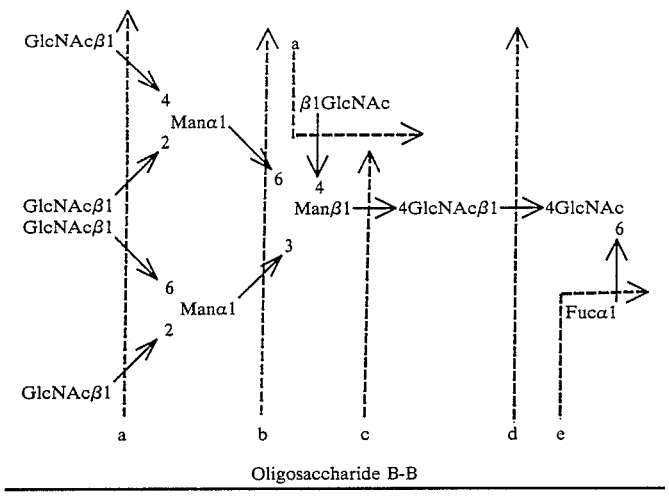

Oligosaccharide B-B

Structural Analysis of Oligosaccharide B-C-1

(section II) and the known biosynthetic pathway of N-linked oligosaccharides are taken into account.

| | | |
|---|---|---|
| (a) J.B. β-hexosaminidase | Δ5 | GlcNAc residues |
| (b) J.B. α-mannosidase | Δ2 | mannose residues |
| (c) snail β-mannosidase | Δ1 | mannose residue |
| (d) J.B. β-hexosaminidase | Δ1 | GlcNAc residue |

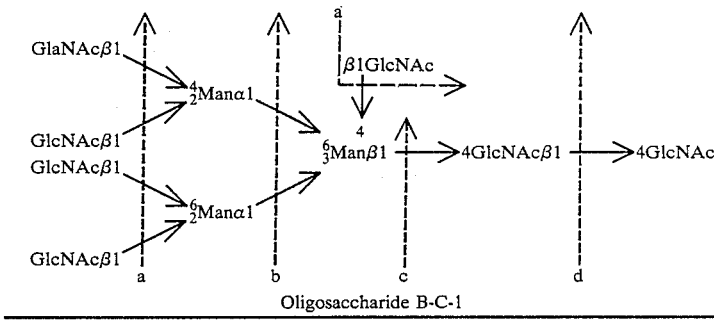

Oligosaccharide B-C-1

The oligosaccharides eluting at 15.24 g.u. were resistant to S.P. β-hexosaminidase. After digestion with J.B. β-galactosidase two fractions were found (15.2 g.u. and 14.2 g.u.). Fraction B-C-1 (15.2 g.u.) was subsequently found to be susceptible to digestion with J.B. β-hexosaminidase[(a)]. After J.B. β-hexosaminidase[(a)] digestion the oligosaccharide eluted at 7.2 g.u., indicating the loss of five β→ linked GlcNAc residues. The digestion product, which eluted at 7.2 g.u., was subsequently incubated with J.B. α-mannosidase[(b)]. The digestion product eluted at 5.5 g.u., indicating the loss of two residues of α-linked mannose. The oligosaccharide fragment eluting at 5.5 g.u. was susceptible to digestion only with snail β-mannosidase[(c)]. After digestion with snail β-mannosidase[(c)] the product eluted at 4.5 g.u. and was susceptible to digestion only with J.B. β-hexosaminidase[(d)]. After incubation with J.B. β-hexosaminidase[(d)] the radioactivity was found at 2.5 g.u. indicating the loss of one GlcNAcβ→ residue.

By comparing the initial elution positions and the exoglycosidase reactivity of oligosaccharides of known sequence (Table 3) the fragmentation which resulted from the sequential exoglycosidase digestion a→b→c→d is consistent with the structure B-C-1 when exoglycosidase anomer, bond and aglycon specificities

Structural Analysis of Oligosaccharide B-C-2

The oligosaccharides eluting at 15.24 g.u. were resistant to S.P. β-hexosaminidase. After digestion with J.B. β-galactosidase[(a)] two fractions were found (15.2 g.u. and 14.2 g.u.). The 14.2 g.u. fraction (B-C-2) was formed by the loss of one residue of Galβ→. Upon treatment with S.P. β-hexosamindase[(b)] one β→linked GlcNAc was removed. Digestion with α-mannosidase had no effect on elution volume. Digestion with J.B. β-hexosaminidase[(c)] resulted in the loss of two additional β→linked GlcNAc residues. The digestion product which eluted at 8.2 g.u. was subsequently digested with J.B. α-mannosidase[(d)]. The digestion product eluted at 6.5 g.u., indicating the loss of two residues of α-linked mannose. The oligosaccharide fragment eluting at 6.5 g.u. was susceptible to digestion only with snail β-mannosidase[(e)] and α-fucosidase[(g)]. After digestion with snail β-mannosidase[(e)] the product eluted at 5.5 g.u. and was susceptible only to J.B. β-hexosaminidase[(f)] and α-fucosidase[(g)]. After J.B. β-hexosaminidase digestion[(f)] the oligosaccharide eluted at 3.5 g.u. and was susceptible only to α-fucosidase[(f)] digestion.

By comparing the initial elution positions and the exoglycosidase reactivity of oligosaccharides of known sequence (Table 3) the fragmentation which resulted from the sequential exoglycosidase digestion a→b→c→d→e→f→g is consistent with the structure B-C-2 when the exoglycosidase anomer, bond and aglycon specificities (section II) and known biosynthetic pathway of N-linked oligosaccharides are taken into account.

eluted at 5.5 g.u. indicating the loss of two residues of α-linked mannose. The oligosaccharide fragment eluting at 5.5 g.u. was susceptible to digestion only with snail β-mannosidase(e). After digestion with snail β-mannosidase(f) the product eluted at 4.5 g.u. and was susceptible to digestion only with J.B. β-hexosaminidase(f). After incubation with J.B. β-hexosaminidase(f) the radioactivity was found at 2.5 g.u.,

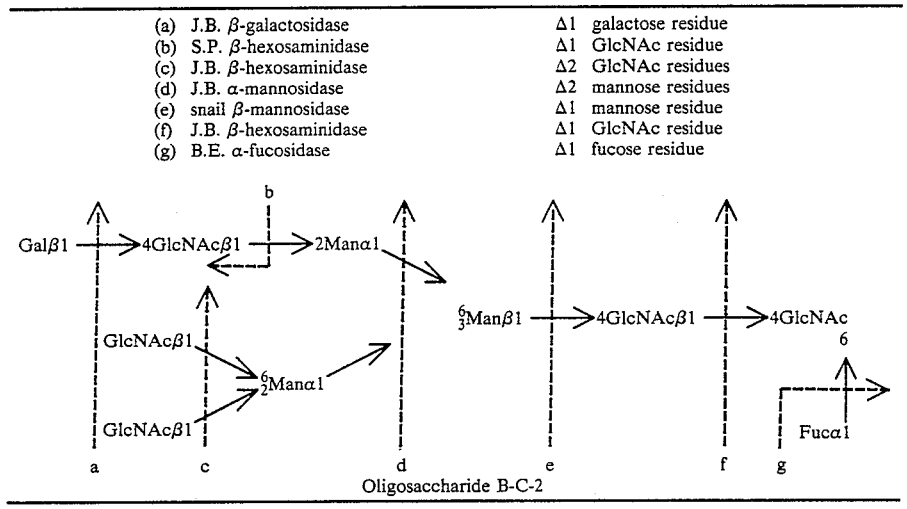

Oligosaccharide B-C-2

| (a) J.B. β-galactosidase | Δ1 galactose residue |
| (b) S.P. β-hexosaminidase | Δ1 GlcNAc residue |
| (c) J.B. β-hexosaminidase | Δ2 GlcNAc residues |
| (d) J.B. α-mannosidase | Δ2 mannose residues |
| (e) snail β-mannosidase | Δ1 mannose residue |
| (f) J.B. β-hexosaminidase | Δ1 GlcNAc residue |
| (g) B.E. α-fucosidase | Δ1 fucose residue |

Structural Analysis of oligosaccharide B-D-1

The oligosaccharides eluting at 14.02 g.u. were treated with S.P. β-hexosaminidase(b). Two fractions were found (14.04 g.u. and 12.2 g.u.). Fraction B-D-1 (14.04 g.u.) was found to be susceptible to digestion with J.B. β-galactosidase(a). The digestion product eluted at 13.1 g.u., indicating the loss of one terminal Gal β1→ residue. The 13.1 g.u. digestion product was now susceptible to S.P. β-hexosaminidase(b). The product eluted at 11.2 g.u., indicating the loss of one GlcNAc β1→ residue. Subsequent digestion with J.B. α-mannosidase has no effect on the elution volume. The 11.2 g.u. product was susceptible to J.B. β-hexosaminidase(c) and now eluted at 7.2 g.u., indicating the loss of two GlcNAc β1→ residues. The digestion product which eluted at 7.2 g.u. was subsequently incubated with J.B. α-mannosidase(d). The digestion product indicating the loss of one GlcNAcβ→ residue.

By comparing the initial elution positions and the exoglycosidase reactivity of oligosaccharides of known sequence (Table 3) the fragmentation which resulted from the sequential exoglycosidase digestion a→b→c→d→e→f is consistent with the structure B-D-1 when exoglycosidase anomer, bond and aglycon specificities (section II) and the known biosynthetic pathway of N-linked oligosaccharides are taken into account.

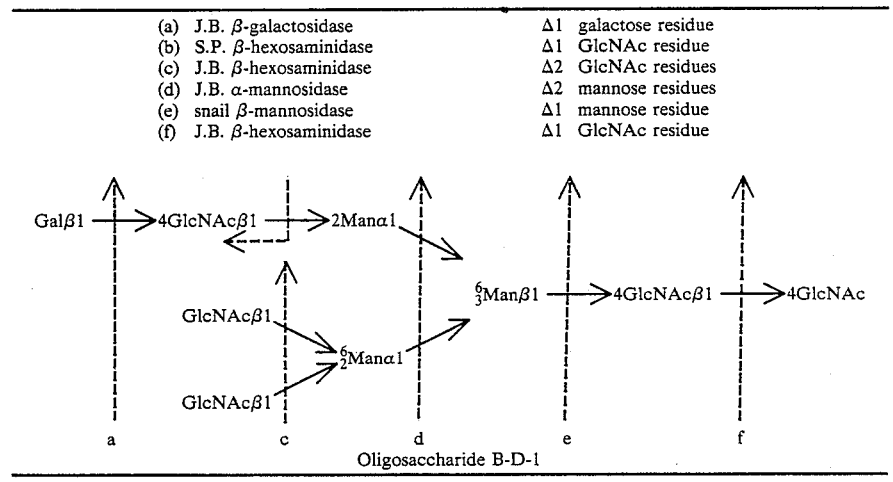

Oligosaccharide B-D-1

| (a) J.B. β-galactosidase | Δ1 galactose residue |
| (b) S.P. β-hexosaminidase | Δ1 GlcNAc residue |
| (c) J.B. β-hexosaminidase | Δ2 GlcNAc residues |
| (d) J.B. α-mannosidase | Δ2 mannose residues |
| (e) snail β-mannosidase | Δ1 mannose residue |
| (f) J.B. β-hexosaminidase | Δ1 GlcNAc residue |

Structural Analysis of Oligosaccharide B-D-2

The oligosaccharides eluting in fraction B-D (centered at 14.02 g.u.) were treated with S.P. β-hexosaminidase(a). Two fractions were found (14.04 g.u. and 12.2 g.u.).

Fraction B-D-2 (12.2 g.u.) lost one GlcNAcβ→ after treatment with S.P. β-hexosaminidase(a). Subsequent digestion with J.B. α-mannosidase had no effect on elution volume. The 12.2 g.u. product was susceptible to J.B. β-hexosaminidase[b] and eluted at 8.2 g.u. indicating the loss of two additional β1→linked GlcNAc residues. The digestion product which eluted at 8.2 g.u. was subsequently digested with J.B. α-mannosidase[c]. The digestion produced eluted at 6.5 g.u., indicating the loss of two residues of α-linked mannose. The oligosaccharide fragment eluting at 6.5 g.u. was susceptible to digestion only with snail β-mannosidase[d] and α-fucosidase[f]. After digestion with snail β-mannosidase[d] the product eluted at 5.5 g.u. and was susceptible to only J.B. β-hexosaminidase[e] and α-fucosidase[f]. After J.B. β-hexosaminidase digestion[e] the oligosaccharide eluted at 3.5 g.u. and was susceptible to only α-fucosidase[f] digestion.

By comparing the initial elution positions and the exoglycosidase reactivity of oligosaccharides of known sequence (Table 3) the fragmentation which resulted from the sequential exoglycosidase digestion a→b→c→d→e→f is consistent with the structure B-D-2 when the exoglycosidase anomer, bond and aglycon specificities (section II) and known biosynthetic pathway of N-linked oligosaccharides are taken into account.

Structural Analysis of Oligosaccharide B-E

The 13.0 g.u. fraction was resistant to J.B. β-galactosidase and S.P. β-hexosaminidase. Upon incubation with J.B. β-hexosaminidase[a] the 13.0 g.u. fraction was converted to a fraction eluting at 8.8 g.u. From this difference in elution volume three GlcNAc→ residues must have been removed. The 8.8 g.u. fraction was subsequently incubated with J.B. α-mannosidase[b] and converted to a fraction eluting at 5.5 g.u., indicating the loss of 4 Manα→ residues. The 5.5 g.u. fraction was resistant to all exoglycosidases except snail β-mannosidase[c]. The 5.5 g.u. fraction was converted to a fraction eluting at 4.5 g.u. indicating the loss of one Manβ→ residue. The 4.5 g.u. fraction was subsequently converted to 2.5 g.u. upon incubation with J.B. β-hexosaminidase[d].

By comparing the initial elution positions and the exoglycosidase reactivity of oligosaccharides of known sequence (Table 3) the fragmentation found on the sequential exoglycosidase digestion a→b→c→d is consistent with structure B-E when exoglycosidase anomer, bond and aglycon specificities (section II), and the known biosynthetic pathway for N-linked oligosaccha-

| (a) | S.P. β-hexosaminidase | Δ1 GlcNAc residue |
| (b) | J.B. β-hexosaminidase | Δ2 GlcNAc residues |
| (c) | J.B. α-mannosidase | Δ2 mannose residues |
| (d) | snail β-mannosidase | Δ1 mannose residue |
| (e) | J.B. β-hexosaminidase | Δ1 GlcNAc residue |
| (f) | B.E. α-fucosidase | Δ1 fucose residue |

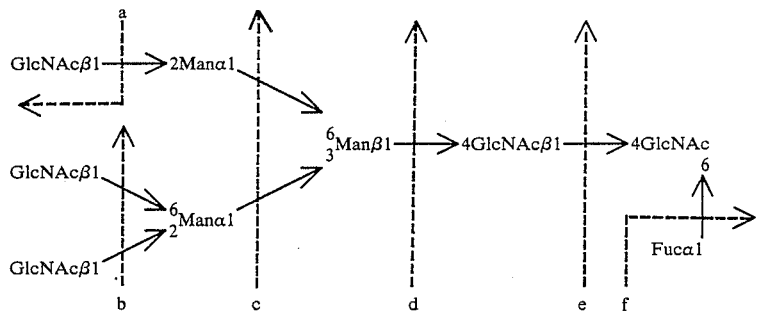

Oligosaccharide B-D-2 rides are taken into account.

| (a) | J.B. β-hexosaminidase | Δ3 GlcNAc residues |
| (b) | J.B. α-mannosidase | Δ4 mannose residues |
| (c) | snail β-mannosidase | Δ1 mannose residue |
| (d) | J.B. β-hexosaminidase | Δ1 GlcNAc residue |

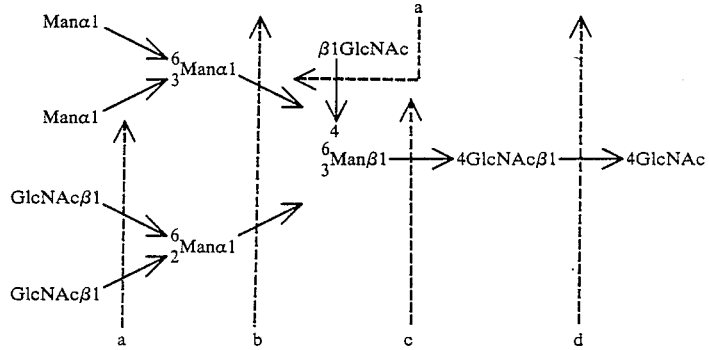

-continued
Oligosaccaride B-E

Structural Analysis of Oligosaccharide B-F-1

The oligosaccharides eluting in Fraction B-F (centered at 11.75 g.u.) were resistant to J.B. β-galactosidase. After digestion with *Asperigillus phoenicis* (A.P.) α-mannosidase two fractions (11.75 g.u. and 8.9 g.u.) were found. The fraction eluting at 11.75 g.u. (B-F-1) was susceptible to treatment with S.P. β-hexosaminidase$^{(a)}$ and converted to a fraction eluting at 8.2 g.u. This difference in elution volume indicates the release of 2 GlcNAcβ→ residues. The digestion product which eluted at 8.2 g.u. was subsequently incubated with J.B. α-mannosidase$^{(b)}$. The digestion product eluted at 6.5 g.u. indicating the loss of two residues of α-linked mannose. The oligosaccharide fragment eluting at 6.5 g.u. was susceptible to digestion only with snail β-mannosidase$^{(c)}$ and α-fucosidase$^{(e)}$. After digestion with snail β-mannosidase$^{(c)}$ the product eluted at 5.5 g.u. and was susceptible to digestion only with J.B. β-hexosaminidase$^{(d)}$ and α-fucosidase$^{(e)}$. After incubation with J.B. β-hexosaminidase$^{(d)}$ the radioactivity was found at 3.5 g.u. indicating the loss of one GlcNAcβ→ residue, and this product was susceptible only to α-fucosidase$^{(e)}$ digestion.

By comparing the initial elution positions and the exoglycosidase reactivity of oligosaccharides of known sequence (Table 3) the fragmentation which resulted from the sequential exoglycosidase digestion a→b→c→d→e is consistent with the structure B-F-1 when exoglycosidase anomer, bond and aglycon specificities (section II) and the known biosynthetic pathway of N-linked oligosaccharides are taken into account.

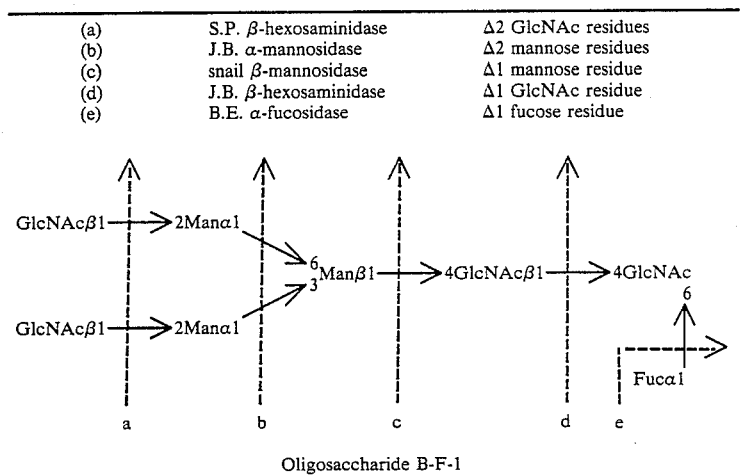

Oligosaccharide B-F-1

Structural Analysis of Oligosaccharide B-F-2

The oligosaccharides eluting in fraction B-F (centered at 11.75 g.u.) were resistant to J.B. β-galactosidase. After digestion with A.P. α-mannosidase$^{(a)}$ two fractions (11.75 g.u. and 8.9 g.u.) (B-F-2) were found. This difference in elution position indicates the loss of three Manα (1→2) residues from B-F-2. Upon subsequent incubation with J.B. α-mannosidase$^{(b)}$ the 8.9 g.u. fraction was converted to a fraction eluting at 5.5 g.u. indicating further loss of 4 Manα residues. The 5.5 g.u. fraction was resistant to all exoglycosidases except snail β-mannosidase$^{(c)}$. When incubated with snail β-mannosidase$^{(c)}$ the 5.5 g.u. fraction was converted to a fraction elugint at 4.5 g.u. indicating the loss of one Manβ1→ residue. The 4.5 g.u. fraction was subsequently converted to a 2.5 g.u. fraction upon incubation with J.B. β-hexosaminidase$^{(d)}$.

By comparing the initial elution positions and the exoglycosidase reactivity of oligosaccharides of known sequence (Table 3) the fragmentation found on the sequential exoglycosidase digestion a→b→c→d is consistent with structure B-F-2 when exoglycosidase anomer, bond and aglycon specificities (section II) and the known biosynthetic pathway of N-linked oligosaccharides are taken into account.

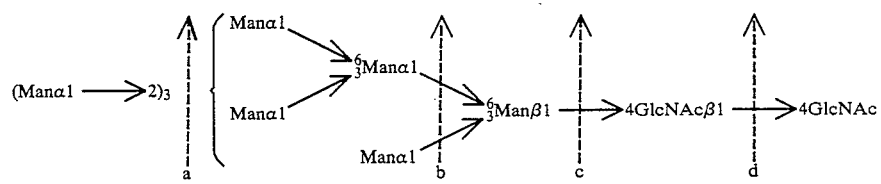

Oligosaccharide B-F-2

Structural Analysis of Oligosaccharide B-G

The 10.5 g.u. fraction when incubated with A.P. α-mannosidase[a] was converted to a fraction eluting at 8.9 g.u. indicating the loss of two Manα 1→2 residues. Upon subsequent incubation with J.B. α-mannosidase[b] the 8.9 g.u. fraction was converted to a fraction eluting at 5.5 g.u. indicating the further loss of 4 Manα residues. The 5.5 g.u. fraction was resistant to all exoglycosidases except snail β-mannosidase[c]. When incubated with snail β-mannosidase[c] the 5.5 g.u. fraction was converted to a fraction eluting at 4.5 g.u. indicating the loss of one Manβ1→ residue. The 4.5 g.u. fraction was subsequently converted to a 2.5 g.u. fraction upon incubation with J.B. β-hexosaminidase[d].

Structural Analysis of Oligosaccharide B-H

The 9.8 g.u. fraction, when incubated with A.P. α-mannosidase[a], was converted to a fraction which eluted at 8.9 g.u. indicating the loss of one Manα 1→2 residue. Upon subsequent incubation with J.B. α-mannosidase[b] the 8.9 g.u. fraction was converted to a fraction eluting at 5.5 g.u. indicating the further loss of 4 Manα residues. The 5.5 g.u. fraction was resistant to all exoglycosidases except snail β-mannosidase[c]. When incubated with snail β-mannosidase[c] the 5.5 g.u. fraction was converted to a fraction eluting at 4.5 g.u. indicating the loss of one Manβ residue. The 4.5 g.u. fraction was subsequently converted to a 2.5 g.u. fraction upon incubation with J.B. β-hexosaminidase[d].

By comparing the initial elution positions and the exoglycosidase reactivity of oligosaccharides of known sequence (Table 3) the fragmentation found on the sequential exoglycosidase digestion a→b→c→d is consistent with structure B-H when exoglycosidase anomer, bond and aglycon specificities (section II) and the known biosynthetic pathway for N-linked oligosaccharides are taken into account.

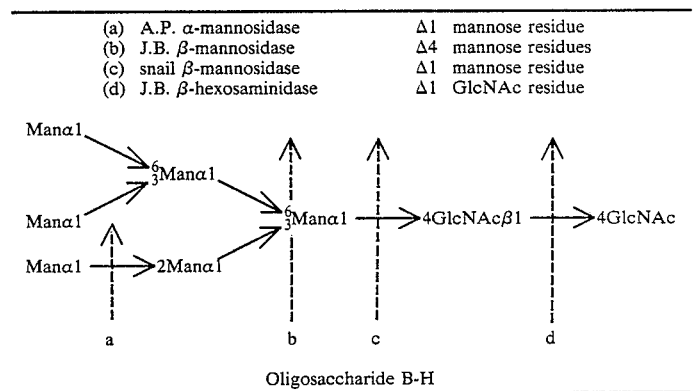

Oligosaccharide B-H

Structural Analysis of Oligosaccharide B-I

The fraction eluting at 8.9 g.u. was resistant to digestion with A.P. α-mannosidase but upon incubation with J.B. α-mannosidase[a] was converted to a fraction eluting at 5.5 g.u., indicating the loss of four Manα residues. The 5.5 g.u. fraction was resistant to all exoglycosidases except snail β-mannosidase[b]. When incubated with By comparing the initial elution positions and the exoglycosidase reactivity of oligosaccharides of known sequence (Table 3) the fragmentation found on the sequential exoglycosidase digestion a→b→c→d is consistent with structure B-G when exoglycosidase anomer, bond and aglycon specificities (section II) and the known biosynthetic pathway of N-linked oligosaccharides are taken into account.

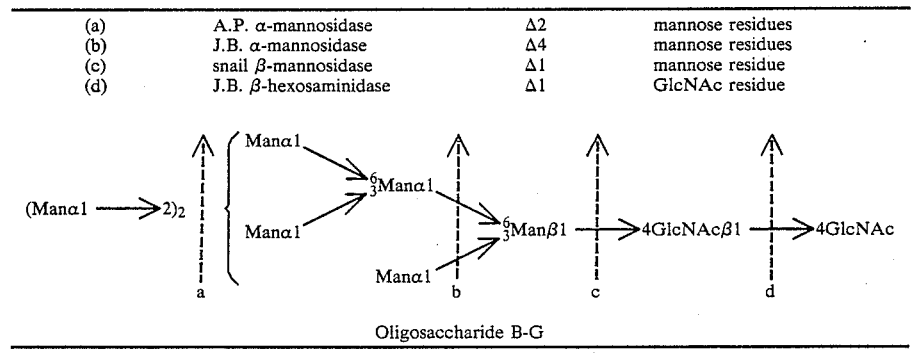

Oligosaccharide B-G

By comparing the initial elution positions and the exoglycosidase reactivity of the oligosaccharides of known sequence (Table 3) the fragmentation found on the sequential exoglycosidase digestion a→b→c is consistent with structure B-I when exoglycosidase anomer, bond and aglycon specificities (section II) and the known biosynthesis of N-linked oligosaccharides is taken into account.

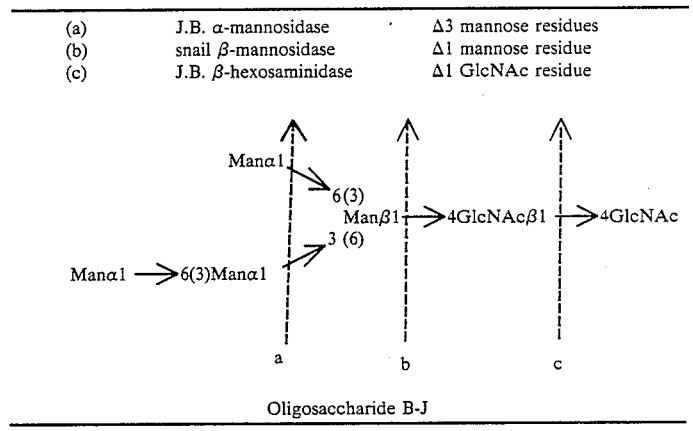

| | | |
|---|---|---|
| (a) | J.B. α-mannosidase | Δ3 mannose residues |
| (b) | snail β-mannosidase | Δ1 mannose residue |
| (c) | J.B. β-hexosaminidase | Δ1 GlcNAc residue |

Oligosaccharide B-J

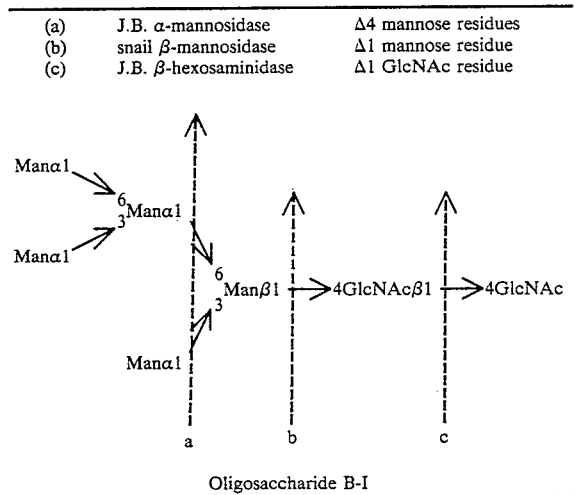

| | | |
|---|---|---|
| (a) | J.B. α-mannosidase | Δ4 mannose residues |
| (b) | snail β-mannosidase | Δ1 mannose residue |
| (c) | J.B. β-hexosaminidase | Δ1 GlcNAc residue |

Oligosaccharide B-I

Structural Analysis of Oligosaccharide B-J

The fraction eluting at 7.9 g.u. was resistant to digestion with A.P. α-mannosidase but upon digestion with J.B. α-mannosidase[(a)] was converted to a fraction eluting at 5.5 g.u., indicating the loss of three Manα residues. The 5.5 g.u. fraction was resistant to all exoglycosidases except snail β-mannosidase[(b)]. When incubated with snail β-mannosidase the 5.5 g.u. fraction was converted to a fraction eluting at 4.5 g.u. indicating the loss of one Manβ residue. The 4.5 g.u. fraction was subsequently converted to a 2.5 g.u. fraction upon incubation with J.B. β-hexosaminidase[(c)].

By comparing the initial elution positions and the exoglycosidase reactivity of oligosaccharides of known sequence (Table 3) the fragmentation found on the sequential exoglycosidase digestion a→b→c is consistent with structure B-J when exoglycosidase anomer, bond and aglycon specificities (section II) and the known biosynthetic pathway for N-linked oligosaccharides are taken into account.

TABLE 4

| | Bowes Melanoma t-PA* | | |
|---|---|---|---|
| Fraction P-4 | Glucose Oligomer Position (g.u.) | Oligosaccharide | Percentage** |
| B-A | 19.5→17.4 | B-A | 1.5 |
| B-B | 17.4→15.5 | B-B | 7.9 |
| B-C | 15.5→14.5 | B-C-1 | 0.9 |
| | | B-C-2 | 2.2 |
| B-D | 14.5→13.5 | B-D-1 | 1.7 |
| | | B-D-2 | 2.6 |
| B-E | 13.5→12.4 | B-E | 4.7 |
| B-F | 12.4→11.4 | B-F-1 | 2.2 |
| | | B-F-2 | 3.9 |
| B-G | 11.4→10.4 | B-G | 11.13 |
| B-H | 10.4→9.5 | B-H | 21.5 |
| B-I | 9.5→8.4 | B-I | 31.1 |
| B-J | 8.4→7.5 | B-J | 6.7 |

*See FIG. 5, Part B
**The percentages determined for each oligosaccharide are estimated to be subject to variation of less than about ±5% of the values shown.

As can be seen from the foregoing Example 2, the three colon t-PA oligosaccharides C-H, C-I and C-J are similar to the melanoma t-PA oligosaccharides B-H, B-I and B-J, whereas the other 13 oligosaccharides of the colon t-PA are not found on the melanoma t-PA.

EXAMPLE 3

In order to further demonstrate the unique glycosylation pattern of the colon t-PA as defined herein compared to the melanoma t-PA, the location on the protein backbone was determined for the individual oligosaccharides described in Example 2. In order to make this determination, tryptic peptides containing the glycosylation sites of the t-PA glycoprotein were prepared and analyzed. These glycosylation sites on the 527 amino acid polypeptide molecule are Asn-117, Asn-184 and Asn-448. The tryptic peptides were obtained by digestion of the t-PA glycoprotein with trypsin and fractionating the resulting mixture by reverse phase HPLC by conventional methods similar to those as described, for example, by Pohl et al., Biochem. 23, 3701–3707 (1984) and Vehar, Biotechnol., December 1984, pp. 1051–1057.

The detailed procedure for isolation of the tryptic peptides was as follows:

Isolation of t-PA. The t-PA glycoprotein fraction was isolated from serum-free conditioned medium by affinity chromatography on $Zn^{2+}$-charged Chelating Sepharose and Concanavalin-A Sepharose essentially as described by Rijken and Collen, *J. Biol. Chem.* 256, 7035-7041 (1981), and as disclosed in Example 2, Table 2, of copending application Ser. No. 849,933, filed Apr. 9, 1986, assigned to the common assigned and incorporated herein by reference. The t-PA fraction eluted from the Concanavalin-A resin as a broad peak (FIG. 10 of said application). Assay of t-PA activity indicated that about 60% of the t-PA eluted between fractions 118 and 230, comprising the mid-section at this peak, with about 12% eluting after fraction 230 at higher α-methylmannoside concentrations (FIG. 10 of said application). This latter material, eluting after fraction 230, was used in this Example.

The Concanvalin-A column eluate was dialyzed against 0.15M arginine-HCl, pH 7.4, containing 0.01% Tween 80, and the t-PA was purified by batch adsorption to an immobilized anti-colon-t-PA monoclonal antibody (clone 63-4). Preparation and use of this antibody for t-PA purification is disclosed in co-pending application, Ser. No. 896,362, filed Aug. 13, 1986, assigned to the common assignee and incorporated herein by reference. The dialyzed Concanavalin-A column eluate was batch adsorbed in several 400-800 ml portions (1600 ml total volume) with about 5 ml of Sepharose-4B to which had been coupled about 2 mg of antibody. The adsorbed t-PA was washed with 0.25M KSCN in phosphate-buffered saline (PBS) containing 0.01% Tween 80 and then eluted with 4M KSCN in this same buffer. The t-PA fraction was then concentrated to a volume of 1.5 ml by ultra-filtration using an Amicon YM05 membrane and subjected to HPLC gel filtration using a TSK-3000 SW column (2.15×30 cm). The column was equilibrated with 1.6M KSCN, 20 mM sodium phosphate, pH 6.8, 0.01% Tween 80, and was eluted at 1 ml/min at room temperature. The peak fractions were combined and the buffer changed to 1M $NH_4HCO_3$ by gel filtration on Sephadex G-25.

This preparation of colon-t-PA was homogeneous by SDS polyacrylamide gel electrophoresis and contained about 50% single-chain and 50% two-chain t-PA species.

Preparation of tryptic peptides. A portion of the above preparation of colon-t-PA (C-tPA) (4.5 ml volume, about 0.64 mg protein) was lyophilized. A similar amount of Bowes melanoma t-PA (B-tPA) (0.645 ml of a 0.93 mg/ml solution in 1M $NH_4HCO_3$, purchased from American Diagnostica, Inc., product number 110, lot 16-01), was diluted to 4.0 ml with 1M $NH_4HCO_3$ and lyophilized. The lyophilized C-tPA and B-tPA samples were then dissolved in 1 ml of 0.1M Tris-HCl, pH 8.15, 6M guanidine-HCl, 2 mM EDTA, degassed under argon, and reduced by adding 10 μl of 0.5M dithiothreitol and incubating 60 min at 37° C. The samples were then carboxymethylated by adding 100 μl of 0.5M iodoacetate in the above tris-quanidine-EDTA buffer and incubating an additional hour. The samples were then desalted by gel filtration over small columns of Sephadex G-25 equilibrated with 1M $NH_4HCO_3$ and lyophilized.

The carboxymethylated, lyophilized samples were then each dissolved in 2 ml of 0.1M $NH_4HCO_3$ and digested for 10 hr at room temperature by the addition of 17.8 μg (C-tPA sample) or 15.7 μg (B-tPA sample) of TPCK-treated trypsin (Sigma Chemical Co.). The trypsinized samples were then lyophilized. The lyophilized glycopeptides were dissolved in 1 ml of 0.1% trifluoroacetic acid (TFA) and subjected to reversed-phase HPLC. HPLC conditions were as follows: Nucleosil ™ C-18, 5 micron, 200 Å, 4.6×250 mm column (Macherey-Nagel, Inc.); room temperature; 1 ml/min flowrate; gradient elution from 0% to 55% acetonitrile from 0 to 165 min. All HPLC elution solvents contained 0.1% TFA.

Amino acid composition, glucosamine and amino acid sequence analyses of similar HPLC separations of C-tPA and B-tPA peptides established: (1) that the tryptic glycopeptide containing glycosylation site Asn-117 eluted in the 74–76 min region; (2) that the peptide containing the glycosylated (or type I) version of site Asn-184 eluted in the 68–72 min region; (3) that the glycopeptide containing site Asn-448 eluted in the 40–46 min region; and (4) that the peptide containing potential site Asn-218 was not glycosylated.

The above mentioned fractions which contained the glycopeptides derived from each of sites 117, 184, 448, were stored at 4° C. for a period of about 4 months. Following this, they were dried by centrifugal vacuum evaporation in a Savant Speed-Vac ® evaporator and then subjected to oligosaccharide analysis as follows:

The tryptic peptides as prepared above were subjected to procedure for isolation of the individual oligosaccharide fractions similar to that described for the intact t-PA glycoprotein in Example 2. The resulting Bio-Gel P-4 chromatograms are shown in FIGS. 7, 8 and 9. The results for the C-tPA tryptic peptides are further summarized in Tables 5, 6 and 7; whereas, the results for the B-tPA tryptic peptides are further summarized in Tables 8, 9 and 10. Thus, Tables 5 and 8 show the percentages of the various oligosaccharide fractions (A to J) attached to each of the glycosylation sites Asn-117, Asn-184 and Asn-448. Tables 6 and 9 show for each of the glycosylation sites the percentages of the oligosaccharides which are complex, hybrid or oligomannose (high mannose). The data is Tables 6 and 9 are also shown graphically in the form of bar charts in FIG. 10. Tables 7 and 10 show for each of the oligosaccharides the percentages of the oligosaccharides which are neutral or sialylated.

TABLE 5

| Glyco-peptide | Colon t-PA Oligosaccharide Fractions (%)* | | | | | | | | | |
|---|---|---|---|---|---|---|---|---|---|---|
| | A | B | C | D | E | F | G | H | I | J |
| Site 117 (A chain-type I & II) | — | — | — | — | — | 5.6 | 8.8 | 24.5 | 44.1 | 17.0 |
| Site 184 (A chain-type I) | — | 4.0 | 12.8 | 39.0 | 13.8 | 4.9 | 7.5 | 8.5 | 6.6 | 2.9 |
| Site 448 (B chain-type I & II) | 3.5 | 25.5 | 30.6 | 29.3 | 11.1 | — | — | — | — | — |

*See FIG. 5, Part A, and Table 2, P-4 Fractions

TABLE 6

| | Colon t-PA | | |
|---|---|---|---|
| Glycopeptide | % Complex | % Hybrid | % Oligomannose |
| Site 117 (A chain-type I & II) | 0 | 9 | 91 |
| Site 184 (A chain-type I) | 72 | 7 | 21 |
| Site 448 (B chain-type | 100 | 0 | 0 |

TABLE 6-continued

| | Colon t-PA | | |
|---|---|---|---|
| Glycopeptide | % Complex | % Hybrid | % Oligomannose |
| I & II) | | | |

TABLE 7

| | Colon t-PA | |
|---|---|---|
| Glycopeptide | % Neutral | % Sialylated |
| Site 117 (A chain-type I & II) | >95 | <5 |
| Site 184 (A chain-type I) | >95 | <5 |
| Site 448 (B chain-type I & II) | 40 | 60 |

TABLE 8

| | Bowes Melanoma t-PA | | | | | | | | |
|---|---|---|---|---|---|---|---|---|---|
| Glyco-peptide | Oligosaccharide Fractions (%)* | | | | | | | | |
| | A | B & C | D | E | F | G | H | I | J |
| Site 117 (A chain-type I & II) | — | — | — | — | 4.8 | 12.5 | 25.8 | 44.3 | 12.6 |
| Site 184 (A chain-type I) | — | 38.2 | 11.1 | 6.0 | 8.2 | 8.0 | 9.3 | 14.6 | 4.6 |
| Site 448 (B chain-type I & II) | 6.2 | 37.0 | 10.1 | 5.6 | 7.1 | 6.0 | 8.2 | 13.9 | 5.9 |

*See FIG. 5, Part B; and Table 4, P-4 Fractions

TABLE 9

| | Bowes Melanoma t-PA | | |
|---|---|---|---|
| Glycopeptide | % Complex (C) | % Hybrid (H) | % Oligomannose (M) |
| Site 117 | 0 | 0 | 100 |
| Site 184 | 52 | 6 | 42 |
| Site 448 | 56 | 6 | 38 |

TABLE 10

| | Bowes Melanoma t-PA | |
|---|---|---|
| Glycopeptide | % Neutral | % Sialylated |
| Site 117 | 100 | 0 |
| Site 184 | ~85 | ~15 |
| Site 448 | ~70 | ~30 |

The foregoing results have been analyzed to characterize the apparent composite glycoforms present. In Table 11, M, C, H, represent the class of oligosaccharides present, i.e., oligomannose, complex or hybrid. The order represents their position on the polypeptide, i.e., 117, 184, 448. In type II the order is 117, 448. Glycoforms indicated with an asterisk are found on both Bowes melanoma t-PA and colon t-PA. Since all of these common forms contain at least one site or more which is of the complex type oligosaccharide class, and there are no complex structures in common between the two t-PA's, no two identical t-PA molecules can occur between Bowes melanoma t-PA and colon produced t-PA.

TABLE 11

| | Colon t-PA | | Bowes t-PA | |
|---|---|---|---|---|
| | Glycoform | Percent Incidence | Glycoform | Percent Incidence |
| Type I | M C C* | 66 | M C C* | 24 |
| | M M C* | 19 | M M C* | 29 |
| | M H C* | 6 | M H C* | 4 |
| | H C C | 6 | — | |
| | H M C | 2 | — | |
| | H H C | <1 | — | |
| | — | | M M M | 19 |
| | — | | M C M | 16 |
| | — | | M M H | 3 |
| | — | | M H M | 3 |
| | — | | M C H | 3 |
| | — | | M H H | <1 |
| Type II | M-C | 91 | M-C | 56 |
| | H-C | 9 | | |
| | — | | M-M | 38 |
| | — | | M-H | 6 |

EXAMPLE 4

In order to demonstrate the effect of the unique glycosylation pattern on the properties of the colon t-PA, the following tests were carried out and/or comparisons made with Bowes melanoma t-PA.

Thermal Stability

The comparative stabilities of colon t-PA and melanoma t-PA were examined under a variety of temperature conditions and buffer compositions at about normal physiological pH. In all such cases tested, the colon t-PA was found to be substantially more stable than the melanoma t-PA; that is, the colon t-PA ranged from about 1.2 times to about 2.6 times more stable than the melanoma t-PA, depending upon the conditions used. Since the amino acid sequences of the two t-PA products are alike, the differences in stability were deemed to be due to the carbohydrate structure. In another test run under selected assay conditions at a relatively low pH of about 2.8, the colon t-PA was found to be only about 5–10% more stable than the melanoma t-PA.

In these stability tests the various temperature and buffer conditions used were: (1) 60° C. for 10 hours in phosphate buffered saline containing 0.01% Tween 80 and 0.01% sodium azide, pH 7.4, supplemented with either one or ten mg/ml of human serum albumin; (2) 98° C. for 60 seconds in the same buffer without the albumin, above, but with or without an equal volume of 0.1M glycine-HCl, pH 2.5, containing 0.01% Tween 80; and (3) 70°–73° C. for 40–90 minutes in 20 mM Tris-HCl, pH 7.6, containing 0.1M NaCl, 0.01% Tween 80 and 100 μg/ml bovine serum albumin.

The stability test results were obtained by several assay methods: amidolytic, parabolic and fibrin plate assays. In the amidolytic assay, hydrolysis of the chromogenic peptide substrate S-2322 (H-D-Val-Gly-Arg-p-nitroanilide, KabiVitrum) by t-PA is measured by monitoring the change in absorbance at 410 nm with time. In the parabolic assay, plasminogen activation is measured by hydrolysis of the chromogenic plasmin substrate, S-2251 (H-D-Val-Leu-Lys-p-nitroanilide, KabiVitrum), in a reaction mixture containing t-PA, excess plasminogen, and excess S-2251. The general procedure for the parabolic assay is described by Ranby, *Biochim. Biophys. Acta* 704, 461–469 (1982) and Verheijen et al., *Thromb. Haemostas.* 48, 266–269 (1982). In the fibrin plate assay, the clearing of an opaque plasminogen-containing fibrin-agar plate by t-PA samples is measured. The general procedure of Haverkate and Brakman, *Prog. Chem. Fibrinolysis and Thrombolysis* 1, 151–159 (1975) was employed.

To further determine the effect of the glycosylation in the colon t-PA of this invention, t-PA was isolated from the colon cells and the conditioned culture medium that was either supplemented or unsupplemented with $B_2$- tunicamycin (Boehringer-Mannheim) in about microgram amounts per ml. $B_2$-tunicamycin is known to inhibit the N-glycosylation of cell-synthesized proteins. A t-PA fraction containing 16% or less of the normal amount of mannose found on the colon t-PA (as a result of the above tunicamycin supplement) was thus compared with the normally (fully) glycosylated t-PA. After heating at 60° C. for 2 hours and then assaying by the parabolic assay method, in the presence or absence of a fibrin-like stimulator (CNBr-generated fragments of human fibrinogen, viz. t-PA stimulator, KabriVitrum), the untreated normal colon t-PA retained from 69–86% of its activity whereas the tunicamycin-treated t-PA with only partial glycosylation retained only 38–42% of its activity. In this test, the t-PA stimulator mimics the stimulatory effects of fibrin. See Zamarron et al., *J. Biol. Chem.* 259, 2080–2083 (1984). Fibrin Stimulatory Properties To directly determine the effect of oligosaccharide chains on colon t-PA activity, t-PA fractions were isolated from colon cells and the conditioned culture media supplemented with $B_2$-tunicamycin, as above, and compared with colon t-PA isolated from the colon cells and conditioned culture media unsupplemented with $B_2$-tunicamycin (control sample). Measurement of [$^3$H]-mannose incorporation and t-PA antigen by ELISA methodology indicated that the t-PA from the tunicamycin-supplemented cells contained 16% or less of the mannose found in the t-PA from the non-supplemented cells (control sample). Samples of the t-PA were assayed by the parabolic assay both with and without the presence of the above fibrin-like stimulator (t-PA stimulator, KabiVirum). In the absence of the t-PA stimulator, significant increases (5 to 6 fold) in the activity of the tunicamycin-treated (less glycosylated) fraction were noted. Since the less glycosylated t-PA was significantly more active in the absence of the t-PA stimulator than the normal (fully) glycosylated t-PA, the net effect of the deglycosylation was to impair somewhat the ability of the t-PA to be regulated by the t-PA stimulator. The therapeutic advantage of t-PA over other plasminogen activators rests in its fibrin-specific action. The foregoing results indicate that the presence of the oligosaccharides on the colon t-PA assist in maintaining a low activity in the absence of fibrin stimulation, thus preventing the non-specific activation of plasminogen. In the presence of the fibrin-like stimulator, the tunicamycin-treated (less glycosylated) sample was somewhat less active than the control sample. However, the less glycosylated t-PA also was less stable in the presence of the fibrin-like stimulator than the normal (fully) glycosylated t-PA.

The colon t-PA of the invention can be used for the treatment of thrombolytic conditions by suitable administration to a patient in need of such treatment. The amount of the t-PA which would normally be administered is primarily dependent upon the physical characteristics of the recipient and the severity of the thrombolytic condition. The amount to be administered must be an effective amount, that is, an amount which is medically beneficial but does not present toxic effects which overweight the advantages which accompany its use. The preferable route of administration is parenteral, especially intravenous. Intravenous administration of the t-PA in solution with normal physiologic saline is illustrative. Other suitable formulations of the active t-PA in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention and it is intended that all such other examples be included within the scope of the appended claims.

What is claimed is:

1. An oligosaccharide selected from the group of complex oligosaccharides C-A, C-B, C-C-1, C-C-2, C-C-3 and C-C-4 as shown in FIG. 6 of the drawings.

* * * * *